US012274517B2

(12) United States Patent
Farritor et al.

(10) Patent No.: US 12,274,517 B2
(45) Date of Patent: Apr. 15, 2025

(54) ROBOTIC DEVICE WITH COMPACT JOINT DESIGN AND AN ADDITIONAL DEGREE OF FREEDOM AND RELATED SYSTEMS AND METHODS

(71) Applicant: Board of Regents of the University of Nebraska, Lincoln, NE (US)

(72) Inventors: Shane Farritor, Lincoln, NE (US); Thomas Frederick, Gretna, NE (US); Lou Cubrich, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 884 days.

(21) Appl. No.: 16/921,073

(22) Filed: Jul. 6, 2020

(65) Prior Publication Data

US 2020/0330171 A1    Oct. 22, 2020

Related U.S. Application Data

(63) Continuation of application No. 15/691,087, filed on Aug. 30, 2017, now Pat. No. 10,702,347.

(60) Provisional application No. 62/381,299, filed on Aug. 30, 2016.

(51) Int. Cl.
| | |
|---|---|
| *A61B 34/30* | (2016.01) |
| *A61B 34/37* | (2016.01) |
| *B25J 9/00* | (2006.01) |
| *B25J 9/10* | (2006.01) |

(52) U.S. Cl.
CPC .............. *A61B 34/30* (2016.02); *A61B 34/37* (2016.02); *B25J 9/0024* (2013.01); *B25J 9/102* (2013.01)

(58) Field of Classification Search
CPC ... A61B 34/30; A61B 34/37; A61B 2218/002; A61B 2218/007; B25J 9/0024; B25J 9/102
See application file for complete search history.

(56) References Cited

U.S. PATENT DOCUMENTS

| | | |
|---|---|---|
| 2,858,947 A | 11/1958 | Chapman, Jr. |
| 3,817,403 A | 6/1974 | Glachet et al. |
| 3,870,264 A | 3/1975 | Robinson |
| 3,922,930 A | 12/1975 | Fletcher et al. |

(Continued)

FOREIGN PATENT DOCUMENTS

| | | |
|---|---|---|
| CA | 2918531 A1 | 1/2015 |
| CN | 101120888 A | 2/2008 |

(Continued)

OTHER PUBLICATIONS

Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.

(Continued)

*Primary Examiner* — Zakaria Elahmadi
(74) *Attorney, Agent, or Firm* — Fredrikson & Byron, P.A.

(57) ABSTRACT

The embodiments disclosed herein relate to various robotic and/or in vivo medical devices having compact joint configurations and at least three degrees of freedom. Other embodiments relate to various medical device components, including forearms having grasper or cautery end effectors, that can be incorporated into certain robotic and/or in vivo medical devices.

5 Claims, 20 Drawing Sheets

(56) References Cited

U.S. PATENT DOCUMENTS

| | | |
|---|---|---|
| 3,971,266 A | 7/1976 | Inakura et al. |
| 3,989,952 A | 11/1976 | Timberlake et al. |
| 4,246,661 A | 1/1981 | Pinson |
| 4,258,716 A | 3/1981 | Sutherland |
| 4,278,077 A | 7/1981 | Mizumoto |
| 4,353,677 A | 10/1982 | Susnjara et al. |
| 4,538,594 A | 9/1985 | Boebel et al. |
| 4,568,311 A | 2/1986 | Miyaki |
| 4,623,183 A | 11/1986 | Aomori |
| 4,636,138 A | 1/1987 | Gorman |
| 4,645,409 A | 2/1987 | Gorman |
| 4,684,313 A | 8/1987 | Minematsu et al. |
| 4,736,645 A | 4/1988 | Zimmer |
| 4,762,455 A | 8/1988 | Coughlan et al. |
| 4,771,652 A | 9/1988 | Zimmer |
| 4,852,391 A | 8/1989 | Ruch et al. |
| 4,854,808 A | 8/1989 | Bisiach |
| 4,896,015 A | 1/1990 | Taboada et al. |
| 4,897,014 A | 1/1990 | Tietze |
| 4,922,755 A | 5/1990 | Oshiro et al. |
| 4,922,782 A * | 5/1990 | Kawai .................. B25J 9/0084 310/71 |
| 4,984,959 A | 1/1991 | Kato |
| 4,990,050 A | 2/1991 | Tsuge et al. |
| 5,019,968 A | 5/1991 | Wang et al. |
| 5,036,724 A | 8/1991 | Rosheim |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,032 A | 2/1993 | Sasaki et al. |
| 5,187,796 A | 2/1993 | Wang et al. |
| 5,195,388 A | 3/1993 | Zona et al. |
| 5,201,325 A | 4/1993 | McEwen et al. |
| 5,217,003 A | 6/1993 | Wilk |
| 5,263,382 A | 11/1993 | Brooks et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,305,653 A | 4/1994 | Ohtani et al. |
| 5,307,447 A | 4/1994 | Asano et al. |
| 5,353,807 A | 10/1994 | DeMarco |
| 5,363,935 A | 11/1994 | Schempf et al. |
| 5,372,147 A | 12/1994 | Lathrop, Jr. et al. |
| 5,382,885 A | 1/1995 | Salcudean et al. |
| 5,388,528 A | 2/1995 | Pelrine et al. |
| 5,397,323 A | 3/1995 | Taylor et al. |
| 5,436,542 A | 7/1995 | Petelin et al. |
| 5,441,494 A | 8/1995 | Oritz |
| 5,456,673 A | 10/1995 | Ziegler et al. |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Takayama et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,667,354 A | 9/1997 | Nakazawa |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyama et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,833,656 A | 11/1998 | Smith et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,377 A | 4/1999 | Smith et al. |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,954,692 A | 9/1999 | Smith et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,086,529 A | 7/2000 | Arndt |
| 6,102,850 A | 8/2000 | Wang et al. |
| 6,106,521 A | 8/2000 | Blewett et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minor et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tiemey et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,450,992 B1 | 9/2002 | Cassidy |
| 6,451,027 B1 | 9/2002 | Cooper et al. |

(56) References Cited

U.S. PATENT DOCUMENTS

| | | |
|---|---|---|
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Nemeyer et al. |
| 6,493,608 B1 | 12/2002 | Niemeyer et al. |
| 6,496,099 B2 | 12/2002 | Wang et al. |
| 6,497,651 B1 | 12/2002 | Kan et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byrne et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,826,977 B2 | 12/2004 | Grover et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,793 B2 | 1/2005 | Brock et al. |
| 6,852,107 B2 | 2/2005 | Wang et al. |
| 6,853,879 B2 | 2/2005 | Sunaoshi |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tiemey et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,963,792 B1 | 11/2005 | Green |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 6,999,852 B2 | 2/2006 | Green |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,155,316 B2 | 12/2006 | Sutherland et al. |
| 7,163,525 B2 | 1/2007 | Franer |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |

(56) References Cited

U.S. PATENT DOCUMENTS

| | | |
|---|---|---|
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,403,836 B2 | 7/2008 | Aoyama |
| 7,438,702 B2 | 10/2008 | Hart et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,678,043 B2 | 3/2010 | Gilad |
| 7,731,727 B2 | 6/2010 | Sauer |
| 7,734,375 B2 | 6/2010 | Buehler et al. |
| 7,762,825 B2 | 7/2010 | Burbank et al. |
| 7,772,796 B2 | 8/2010 | Farritor et al. |
| 7,785,251 B2 | 8/2010 | Wilk |
| 7,785,294 B2 | 8/2010 | Hueil et al. |
| 7,785,333 B2 | 8/2010 | Miyamoto et al. |
| 7,789,825 B2 | 9/2010 | Nobis et al. |
| 7,789,861 B2 | 9/2010 | Franer |
| 7,794,494 B2 | 9/2010 | Sahatjian et al. |
| 7,865,266 B2 | 1/2011 | Moll et al. |
| 7,960,935 B2 | 6/2011 | Farritor et al. |
| 7,979,157 B2 | 7/2011 | Anvari |
| 8,021,358 B2 | 9/2011 | Doyle et al. |
| 8,179,073 B2 | 5/2012 | Farritor et al. |
| 8,231,610 B2 | 7/2012 | Jo et al. |
| 8,343,171 B2 * | 1/2013 | Farritor ............... A61B 34/73 600/564 |
| 8,353,897 B2 | 1/2013 | Doyle et al. |
| 8,377,045 B2 | 2/2013 | Schena |
| 8,430,851 B2 | 4/2013 | Mcginley et al. |
| 8,604,742 B2 | 12/2013 | Farritor et al. |
| 8,636,686 B2 | 1/2014 | Minnelli et al. |
| 8,679,096 B2 | 3/2014 | Farritor et al. |
| 8,827,337 B2 | 9/2014 | Murata et al. |
| 8,828,024 B2 * | 9/2014 | Farritor ............ A61B 17/00234 606/130 |
| 8,834,488 B2 | 9/2014 | Farritor et al. |
| 8,864,652 B2 | 10/2014 | Diolaiti et al. |
| 8,888,687 B2 | 11/2014 | Ostrovsky et al. |
| 8,968,332 B2 | 3/2015 | Farritor et al. |
| 8,974,440 B2 | 3/2015 | Farritor et al. |
| 8,986,196 B2 | 3/2015 | Larkin et al. |
| 9,010,214 B2 | 4/2015 | Markvicka et al. |
| 9,060,781 B2 | 6/2015 | Farritor et al. |
| 9,089,256 B2 | 7/2015 | Tognaccini et al. |
| 9,089,353 B2 | 7/2015 | Farritor et al. |
| 9,138,129 B2 | 9/2015 | Diolaiti |
| 9,198,728 B2 | 12/2015 | Wang et al. |
| 9,516,996 B2 | 12/2016 | Diolaiti et al. |
| 9,579,088 B2 | 2/2017 | Farritor et al. |
| 9,649,020 B2 | 5/2017 | Finlay |
| 9,717,563 B2 | 8/2017 | Tognaccini et al. |
| 9,743,987 B2 | 8/2017 | Farritor et al. |
| 9,757,187 B2 * | 9/2017 | Farritor ............. A61B 18/1445 |
| 9,770,305 B2 | 9/2017 | Farritor et al. |
| 9,789,608 B2 | 10/2017 | Itkowitz et al. |
| 9,814,640 B1 | 11/2017 | Khaligh |
| 9,816,641 B2 | 11/2017 | Bock-Aronson et al. |
| 9,849,586 B2 | 12/2017 | Rosheim |
| 9,857,786 B2 | 1/2018 | Cristiano |
| 9,888,966 B2 | 2/2018 | Farritor et al. |
| 9,956,043 B2 | 5/2018 | Farritor et al. |
| 10,008,017 B2 | 6/2018 | Itkowitz et al. |
| 10,111,711 B2 | 10/2018 | Farritor et al. |
| 10,137,575 B2 | 11/2018 | Itkowitz et al. |
| 10,159,533 B2 | 12/2018 | Moll et al. |
| 10,220,522 B2 | 3/2019 | Rockrohr |
| 10,258,425 B2 | 4/2019 | Mustufa et al. |
| 10,307,199 B2 | 6/2019 | Farritor et al. |
| 10,342,561 B2 | 7/2019 | Farritor et al. |
| 10,368,952 B2 | 8/2019 | Tognaccini et al. |
| 10,398,516 B2 | 9/2019 | Jackson et al. |
| 10,470,828 B2 | 11/2019 | Markvicka et al. |
| 10,507,066 B2 | 12/2019 | Dimaio et al. |
| 10,555,775 B2 | 2/2020 | Hoffman et al. |
| 10,582,973 B2 | 3/2020 | Wilson et al. |
| 10,695,137 B2 | 6/2020 | Farritor et al. |
| 10,729,503 B2 | 8/2020 | Cameron |
| 10,737,394 B2 | 8/2020 | Itkowitz et al. |
| 10,751,136 B2 | 8/2020 | Farritor et al. |
| 10,751,883 B2 | 8/2020 | Nahum |
| 10,806,538 B2 | 10/2020 | Farritor et al. |
| 10,966,700 B2 | 4/2021 | Farritor et al. |
| 11,032,125 B2 | 6/2021 | Farritor et al. |
| 11,298,195 B2 | 4/2022 | Ye et al. |
| 11,382,702 B2 | 7/2022 | Tognaccini et al. |
| 11,529,201 B2 | 12/2022 | Mondry et al. |
| 11,595,242 B2 | 2/2023 | Farritor et al. |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszko et al. |
| 2002/0038077 A1 | 3/2002 | de la Torre et al. |
| 2002/0065507 A1 | 5/2002 | Zando-Azizi |
| 2002/0091374 A1 | 6/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julian et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0109780 A1 | 6/2003 | Coste-Maniere et al. |
| 2003/0114731 A1 | 6/2003 | Cadeddu et al. |
| 2003/0135203 A1 | 6/2003 | Wang et al. |
| 2003/0139742 A1 | 7/2003 | Wampler et al. |
| 2003/0144656 A1 | 7/2003 | Ocel et al. |
| 2003/0159535 A1 | 8/2003 | Grover et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0225479 A1 | 12/2003 | Waled |
| 2003/0229268 A1 | 12/2003 | Uchiyama et al. |
| 2003/0229338 A1 | 12/2003 | Irion et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0117032 A1 | 6/2004 | Roth |
| 2004/0138525 A1 | 7/2004 | Saadat et al. |
| 2004/0138552 A1 | 7/2004 | Harel et al. |
| 2004/0140786 A1 | 7/2004 | Borenstein |
| 2004/0153057 A1 | 8/2004 | Davison |

(56) References Cited

U.S. PATENT DOCUMENTS

| | | |
|---|---|---|
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0070850 A1 | 3/2005 | Albrecht |
| 2005/0083460 A1 | 4/2005 | Hattori et al. |
| 2005/0095650 A1 | 5/2005 | Julius et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0177026 A1 | 8/2005 | Hoeg et al. |
| 2005/0234294 A1 | 10/2005 | Saadat et al. |
| 2005/0234435 A1 | 10/2005 | Layer |
| 2005/0272977 A1 | 12/2005 | Saadat et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0079889 A1 | 4/2006 | Scott |
| 2006/0100501 A1 | 5/2006 | Berkelman et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0189845 A1 | 8/2006 | Maahs et al. |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker |
| 2006/0253109 A1 | 11/2006 | Chu |
| 2006/0258938 A1 | 11/2006 | Hoffman et al. |
| 2006/0258954 A1 | 11/2006 | Timberlake et al. |
| 2006/0261770 A1 | 11/2006 | Kishi et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0088277 A1 | 4/2007 | Mcginley et al. |
| 2007/0088340 A1 | 4/2007 | Brock et al. |
| 2007/0106113 A1 | 5/2007 | Ravo |
| 2007/0106317 A1 | 5/2007 | Shelton et al. |
| 2007/0123748 A1 | 5/2007 | Meglan |
| 2007/0135803 A1 | 6/2007 | Belson |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De et al. |
| 2007/0225633 A1 | 9/2007 | Ferren et al. |
| 2007/0225634 A1 | 9/2007 | Ferren et al. |
| 2007/0241714 A1 | 10/2007 | Oleynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2007/0287884 A1 | 12/2007 | Schena |
| 2008/0004634 A1 | 1/2008 | Farritor et al. |
| 2008/0015565 A1 | 1/2008 | Davison |
| 2008/0015566 A1 | 1/2008 | Livneh |
| 2008/0021440 A1 | 1/2008 | Solomon |
| 2008/0033569 A1 | 2/2008 | Ferren et al. |
| 2008/0045803 A1 | 2/2008 | Williams et al. |
| 2008/0058835 A1 | 3/2008 | Farritor et al. |
| 2008/0058989 A1 | 3/2008 | Oleynikov et al. |
| 2008/0071289 A1 | 3/2008 | Cooper et al. |
| 2008/0071290 A1 | 3/2008 | Larkin et al. |
| 2008/0103440 A1 | 5/2008 | Ferren et al. |
| 2008/0109014 A1 | 5/2008 | de la Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 6/2008 | Rioux et al. |
| 2008/0164079 A1 | 7/2008 | Ferren et al. |
| 2008/0168639 A1 | 7/2008 | Otake et al. |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0002414 A1 | 1/2009 | Shibata et al. |
| 2009/0012532 A1 | 1/2009 | Quaid et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0192524 A1 | 7/2009 | Itkowitz et al. |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0299143 A1 | 12/2009 | Conlon et al. |
| 2009/0305210 A1 | 12/2009 | Guru et al. |
| 2009/0326322 A1 | 12/2009 | Diolaiti |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0026347 A1 | 2/2010 | Iizuka |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0101346 A1 | 4/2010 | Johnson et al. |
| 2010/0130986 A1 | 5/2010 | Mailloux et al. |
| 2010/0139436 A1 | 6/2010 | Kawashima et al. |
| 2010/0185212 A1 | 7/2010 | Sholev |
| 2010/0198231 A1 | 8/2010 | Manzo et al. |
| 2010/0204713 A1 | 8/2010 | Ruiz Morales |
| 2010/0245549 A1 | 9/2010 | Allen et al. |
| 2010/0250000 A1 | 9/2010 | Blumenkranz et al. |
| 2010/0262162 A1 | 10/2010 | Omori |
| 2010/0263470 A1 | 10/2010 | Bannasch et al. |
| 2010/0274079 A1 | 10/2010 | Kim et al. |
| 2010/0292691 A1 | 11/2010 | Brogna |
| 2010/0301095 A1 | 12/2010 | Shelton, IV et al. |
| 2010/0318059 A1 | 12/2010 | Farritor et al. |
| 2010/0331856 A1 | 12/2010 | Carlson et al. |
| 2011/0015569 A1 | 1/2011 | Kirschenman et al. |
| 2011/0020779 A1 | 1/2011 | Hannaford et al. |
| 2011/0071347 A1 | 3/2011 | Rogers et al. |
| 2011/0071544 A1 | 3/2011 | Steger et al. |
| 2011/0075693 A1 | 3/2011 | Kuramochi et al. |
| 2011/0077478 A1 | 3/2011 | Freeman et al. |
| 2011/0082365 A1 | 4/2011 | Mcgrogan et al. |
| 2011/0098529 A1 | 4/2011 | Ostrovsky et al. |
| 2011/0107866 A1 | 5/2011 | Oka et al. |
| 2011/0152615 A1 | 6/2011 | Schostek et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238079 A1 | 9/2011 | Hannaford et al. |
| 2011/0238080 A1 | 9/2011 | Ranjit et al. |
| 2011/0264078 A1 | 10/2011 | Lipow et al. |
| 2011/0270443 A1 | 11/2011 | Kamiya et al. |
| 2011/0276046 A1 | 11/2011 | Heimbecker et al. |

(56) References Cited

U.S. PATENT DOCUMENTS

| | | | |
|---|---|---|---|
| 2012/0016175 A1 | 1/2012 | Roberts et al. |
| 2012/0029727 A1 | 2/2012 | Sholev |
| 2012/0035582 A1 | 2/2012 | Nelson et al. |
| 2012/0059392 A1 | 3/2012 | Diolaiti |
| 2012/0078053 A1 | 3/2012 | Phee et al. |
| 2012/0109150 A1 | 5/2012 | Quaid et al. |
| 2012/0116362 A1 | 5/2012 | Kieturakis |
| 2012/0179168 A1 | 7/2012 | Farritor et al. |
| 2012/0221147 A1 | 8/2012 | Goldberg et al. |
| 2012/0253515 A1 | 10/2012 | Coste-Maniere et al. |
| 2013/0001970 A1 | 1/2013 | Suyama et al. |
| 2013/0041360 A1 | 2/2013 | Farritor et al. |
| 2013/0055560 A1 | 3/2013 | Nakasugi et al. |
| 2013/0125696 A1 | 5/2013 | Long |
| 2013/0131695 A1 | 5/2013 | Scarfogliero et al. |
| 2013/0178867 A1 | 7/2013 | Farritor et al. |
| 2013/0282023 A1 | 10/2013 | Burbank et al. |
| 2013/0304084 A1 | 11/2013 | Beira et al. |
| 2013/0325030 A1 | 12/2013 | Hourtash et al. |
| 2013/0325181 A1 | 12/2013 | Moore |
| 2013/0345717 A1 | 12/2013 | Markvicka et al. |
| 2013/0345718 A1 | 12/2013 | Crawford et al. |
| 2014/0039515 A1 | 2/2014 | Mondry et al. |
| 2014/0046340 A1 | 2/2014 | Wilson et al. |
| 2014/0055489 A1 | 2/2014 | Itkowitz et al. |
| 2014/0058205 A1 | 2/2014 | Frederick et al. |
| 2014/0100587 A1 | 4/2014 | Farritor et al. |
| 2014/0137687 A1 | 5/2014 | Nogami et al. |
| 2014/0221749 A1 | 8/2014 | Grant et al. |
| 2014/0232824 A1 | 8/2014 | Dimaio et al. |
| 2014/0276944 A1 | 9/2014 | Farritor et al. |
| 2014/0303434 A1* | 10/2014 | Farritor | A61B 1/00149 600/102 |
| 2014/0371762 A1* | 12/2014 | Farritor | B25J 9/1602 901/46 |
| 2015/0051446 A1* | 2/2015 | Farritor | A61B 1/0057 600/102 |
| 2015/0057537 A1 | 2/2015 | Dillon et al. |
| 2015/0157191 A1 | 6/2015 | Phee et al. |
| 2015/0223896 A1 | 8/2015 | Farritor et al. |
| 2015/0297299 A1 | 10/2015 | Yeung et al. |
| 2016/0066999 A1 | 3/2016 | Forgione et al. |
| 2016/0135898 A1 | 5/2016 | Frederick et al. |
| 2016/0291571 A1 | 10/2016 | Cristiano |
| 2016/0303745 A1* | 10/2016 | Rockrohr | B25J 17/0258 |
| 2017/0014197 A1 | 1/2017 | Mccrea et al. |
| 2017/0035526 A1 | 2/2017 | Farritor et al. |
| 2017/0078583 A1 | 3/2017 | Haggerty et al. |
| 2017/0252096 A1* | 9/2017 | Felder | A61B 18/1445 |
| 2017/0354470 A1 | 12/2017 | Farritor et al. |
| 2018/0132956 A1 | 5/2018 | Cameron |
| 2018/0153578 A1 | 6/2018 | Cooper et al. |
| 2018/0338777 A1 | 11/2018 | Bonadio et al. |
| 2019/0059983 A1 | 2/2019 | Germain et al. |
| 2019/0090965 A1 | 3/2019 | Farritor et al. |
| 2019/0209262 A1 | 7/2019 | Mustufa et al. |
| 2019/0327394 A1 | 10/2019 | Ramirez Luna et al. |
| 2020/0138534 A1 | 5/2020 | Garcia Kilroy et al. |
| 2020/0214775 A1 | 7/2020 | Farritor et al. |
| 2020/0330175 A1 | 10/2020 | Cameron |
| 2020/0368915 A1 | 11/2020 | Itkowitz et al. |

FOREIGN PATENT DOCUMENTS

| | | |
|---|---|---|
| CN | 102499759 A | 6/2012 |
| CN | 102821918 | 12/2012 |
| CN | 104523309 A | 4/2015 |
| CN | 104582600 A | 4/2015 |
| CN | 104622528 A | 5/2015 |
| CN | 204337044 U | 5/2015 |
| CN | 104786233 A | 7/2015 |
| CN | 105025826 A | 11/2015 |
| DE | 102010040405 | 3/2012 |
| EP | 0105656 A2 | 4/1984 |
| EP | 0279591 A1 | 8/1988 |
| EP | 1354670 | 10/2003 |
| EP | 2286756 | 2/2011 |
| EP | 2286756 A1 | 2/2011 |
| EP | 2329787 | 6/2011 |
| EP | 2563261 | 3/2013 |
| EP | 2684528 A1 | 1/2014 |
| EP | 2123225 B1 | 12/2014 |
| EP | 2815705 A1 | 12/2014 |
| EP | 2881046 A2 | 10/2015 |
| EP | 2937047 A1 | 10/2015 |
| JP | S59059371 A | 4/1984 |
| JP | 60001456 A | 1/1985 |
| JP | S601456 A | 1/1985 |
| JP | S61165061 A | 7/1986 |
| JP | S62068293 A | 3/1987 |
| JP | 01109094 A | 4/1989 |
| JP | H04144533 A | 5/1992 |
| JP | 05-115425 | 5/1993 |
| JP | 2006508049 | 9/1994 |
| JP | H06507809 A | 9/1994 |
| JP | H06508049 A | 9/1994 |
| JP | 07-016235 | 1/1995 |
| JP | 07-136173 | 5/1995 |
| JP | 7306155 | 11/1995 |
| JP | 08-224248 | 9/1996 |
| JP | 2001500510 | 1/2001 |
| JP | 2001505810 | 5/2001 |
| JP | 2002000524 A | 1/2002 |
| JP | 2003220065 | 8/2003 |
| JP | 2004144533 | 5/2004 |
| JP | 2004-180781 | 7/2004 |
| JP | 2004283940 A | 10/2004 |
| JP | 2004322310 | 11/2004 |
| JP | 2004329292 | 11/2004 |
| JP | 2006507809 | 3/2006 |
| JP | 2009106606 | 5/2009 |
| JP | 2009297809 A | 12/2009 |
| JP | 2010533045 | 10/2010 |
| JP | 2010536436 | 12/2010 |
| JP | 2011504794 | 2/2011 |
| JP | 2011045500 | 3/2011 |
| JP | 2011115591 | 6/2011 |
| JP | 2012504017 A | 2/2012 |
| JP | 2012176489 A | 9/2012 |
| JP | 5418704 B1 | 2/2014 |
| JP | 2015526171 A | 9/2015 |
| JP | 2016213937 A | 12/2016 |
| JP | 2017113837 A | 6/2017 |
| WO | 199221291 | 5/1991 |
| WO | 2001089405 | 11/2001 |
| WO | 2002082979 | 10/2002 |
| WO | 2002100256 | 12/2002 |
| WO | 2005009211 | 7/2004 |
| WO | 2005044095 | 5/2005 |
| WO | 2006052927 | 8/2005 |
| WO | 2006005075 | 1/2006 |
| WO | 2006079108 | 1/2006 |
| WO | 2007011654 | 1/2007 |
| WO | 2007111571 | 10/2007 |
| WO | 2007149559 | 12/2007 |
| WO | 2009014917 A2 | 1/2009 |
| WO | 2009023851 | 2/2009 |
| WO | 2009144729 | 12/2009 |
| WO | 2009158164 A1 | 12/2009 |
| WO | 2010039394 A1 | 4/2010 |
| WO | 2010042611 A1 | 4/2010 |
| WO | 2010046823 A1 | 4/2010 |
| WO | 2010050771 | 5/2010 |
| WO | 2010083480 A2 | 7/2010 |
| WO | 2011075693 | 6/2011 |
| WO | 2011118646 | 9/2011 |
| WO | 2011135503 | 11/2011 |
| WO | 2011163520 A2 | 12/2011 |
| WO | 2013009887 | 1/2013 |
| WO | 2013052137 A2 | 4/2013 |
| WO | 2013106569 A2 | 7/2013 |
| WO | 2014011238 | 1/2014 |
| WO | 2014025399 A1 | 2/2014 |

(56) References Cited

FOREIGN PATENT DOCUMENTS

| WO | 2014144220 A1 | 9/2014 |
|---|---|---|
| WO | 2014146090 A1 | 9/2014 |
| WO | 2015009949 A2 | 1/2015 |
| WO | 2015031777 A1 | 3/2015 |
| WO | 2015088655 A1 | 6/2015 |
| WO | 2016077478 A1 | 5/2016 |
| WO | 2017024081 A1 | 2/2017 |
| WO | 2017064303 A1 | 4/2017 |
| WO | 2017201310 A1 | 11/2017 |
| WO | 2018045036 A1 | 3/2018 |

OTHER PUBLICATIONS

Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.
Atmel 80C5X2 Core, http://www.atmel.com, 2006, 186pp.
Bailey et al., "Complications of Laparoscopic Surgery," Quality Medical Publishers, Inc., 1995, 25pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.
Cavusoglu et al., "Telesurgery and Surgical Simulation: Haptic Interfaces to Real and Virtual Surgical Environments," In Mclaughlin, M.L., Hespanha, J.P., and Sukhatme, G., editors. Touch in virtual environments, IMSC Series in Multimedia 2001, 28pp.
Dumpert et al., "Stereoscopic In Vivo Surgical Robots," IEEE Sensors Special Issue on In Vivo Sensors for Medicine, Jan. 2007, 10 pp.
Green, "Telepresence Surgery", Jan. 1, 1995, Publisher: IEEE Engineering in Medicine and Biology.
Cleary et al., "State of the Art in Surgical Rootics: Clinical Applications and Technology Challenges", "Computer Aided Surgery", Jan. 1, 2002, pp. 312-328, vol. 6.
Stoianovici et al., "Robotic Tools for Minimally Invasive Urologic Surgery", Jan. 1, 2002, pp. 1-17.
Franzino, "The Laprotek Surgical System and the Next Generation of Robotics," Surg Clin North Am, 2003 83(6): 1317-1320.
Franklin et al., "Prospective Comparison of Open vs. Laparoscopic Colon Surgery for Carcinoma: Five-Year Results," Dis Colon Rectum, 1996; 39: S35-S46.
Flynn et al, "Tomorrow's surgery: micromotors and microrobots for minimally invasive procedures," Minimally Invasive Surgery & Allied Technologies, 1998; 7(4): 343-352.
Fireman et al., "Diagnosing small bowel Crohn's desease with wireless capsule endoscopy," Gut 2003; 52: 390-392.

Fearing et al., "Wing Transmission for a Micromechanical Flying Insect," Proceedings of the 2000 IEEE International Conference to Robotics & Automation, Apr. 2000; 1509-1516.
Faraz et al., "Engineering Approaches to Mechanical and Robotic Design for Minimaly Invasive Surgery (MIS)," Kluwer Academic Publishers (Boston), 2000, 13pp.
Falcone et al., "Robotic Surgery," Clin. Obstet. Gynecol. 2003, 46(1): 37-43.
Fraulob et al., "Miniature assistance module for robot-assisted heart surgery," Biomed. Tech. 2002, 47 Suppl. 1, Pt. 1: 12-15.
Fukuda et al., "Mechanism and Swimming Experiment of Micro Mobile Robot in Water," Proceedings of the 1994 IEEE International Conference on Robotics and Automation, 1994: 814-819.
Fukuda et al., "Micro Active Catheter System with Multi Degrees of Freedom," Proceedings of the IEEE International Conference on Robotics and Automation, May 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Dumpert et al., "Improving in Vivo Robot Visioin Quality," from the Proceedings of Medicine Meets Virtual Realtiy, Long Beach, CA, Jan. 26-29, 2005. 1 pg.
Dakin et al., "Comparison of laparoscopic skills performance between standard instruments and two surgical robotic systems," Surg Endosc., 2003; 17: 574-579.
Cuschieri, "Technology for Minimal Access Surgery," BMJ, 1999, 319: 1-6.
Grady, "Doctors Try New Surgery for Gallbladder Removal," The New York Times, Apr. 20, 2007, 3 pp.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Chanthasopeephan et al., (2003), "Measuring Forces in Liver Cutting: New Equipment and Experimenal Results," Annals of Biomedical Engineering 31: 1372-1382.
Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.
Guber et al., "Miniaturized Instrument Systems for Minimally Invasive Diagnosis and Therapy," Biomedizinische Technic. 2002, Band 47, Erganmngsband 1: 198-201.
Lehman et al., Dexterous miniature in vivo robot for NOTES, 2009, IEEE, p. 244-249.
Mihelj et al., ARMin II—7 DoF rehabilitation robot: mechanics and kinematics, 2007, IEEE, p. 4120-4125.
Zhang et al., Cooperative robotic assistant for laparoscopic surgery: CoBRASurge, 2009, IEEE, p. 5540-5545.
Park et al., "Experimental studies of transgastric gallbladder surgery: cholecystectomy and cholecystogastric anastomosis (videos)," Gastrointestinal Endoscopy, 2005; 61 (4): 601-606.
Phee et al., "Development of Microrobotic Devices for Locomotion in the Human Gastrointestinal Tract," International Conference on Computational Intelligence, Robotics and Autonomous Systems (CI RAS 2001), Nov. 28-30, (2001), Singapore, 6 pages.
Phee et al., "Analysis and Development of Locomotion Devices for the Gastrointestinal Tract," IEEE Transactions on Biomedical Engineering, vol. 49, No. 6, Jun. 2002: 613-616.
Platt et al., "In Vivo Robotic Cameras can Enhance Imaging Capability During Laparoscopic Surgery," from the Proceedings of the Society of American Gastrointestinal Endoscopic Surgeons (SAGES) Scientific Conference, Ft. Lauderdale, FL, Apr. 13-16, 2005; 1 pg.
Qian Huan et al., "Multi-joint Single-wound Minimally Invasive Abdominal Surgery Robot Design," Mechanical Design and Manufacturing, May 8, 2014, pp. 134-137.
Rentschler et al., "In vivo Mobile Surgical Robotic Task Assistance," 1 pg.

(56) References Cited

OTHER PUBLICATIONS

Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004; pp. 1-9.
Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, April 13-16, 2005b.
Rentschler et al., "Modeling, Analysis, and Experimental Study of In Vivo Wheeled Robotic Mobility," IEEE Transactions on Robotics, 22 (2): 308-321, 2005c.
Rentschler et al., "Miniature in vivo robots for remote and harsh environments," IEEE Transaction on Information Technology in Biomedicine, Jan. 2006; 12(1): pp. 66-75.
Rentschler et al., "Mobile In Vivo Camera Robots Provide Sole Visual Feedback for Abdominal Exploration and Cholecystectomy," Journal of Surgical Endoscopy, 20-1: 135-138, 2006b.
Rentschler et al., "Natural Orifice Surgery with an Endoluminal Mobile Robot," The Society of American Gastrointestinal Endoscopic Surgeons, Dallas, TX, April 2006d.
Riviere et al., "Toward Active Tremor Canceling in Handheld Microsurgical Instruments," IEEE Transactions on Robotics and Automation, Oct. 2003, 19(5): 793-800.
Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.
Rosen et al., "Spherical Mechanism Analysis of a Surgical Robot for Minimally Invasive Surgery—Analytical and Experimental Approaches," Studies in Health Technology and Infonnatics-Medicine Meets Virtual Reality, pp. 442-448, Jan. 2005.
Ruurda et al., "Feasibility of Robot-Assisted Laparoscopic Surgery," Surgical Laparoscopy, Endoscopy & Percutaneous Techniques, 2002; 12(1):41-45.
Schippers et al. (1996), "Requirements and Possibilities of Computer-Assisted Endoscopic Surgery," In: Computer Integrated Surgery: Technology and Clinical Applications, pp. 561-565.
Slatkin et al., "The Development of a Robotic Endoscope," Proceedings of the 1995 IEEE International Conference on Robotics and Automation, pp. 162-171, 1995.
Sodeyama et al., A shoulder structure of muscle-driven humanoid with shoulder blades, 2005, IEEE, p. 1-6 (Year: 2005).
Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.
Abbou et al., "Laparoscopic Radical Prostatectomy with a Remote Controlled Robot," The Journal of Urology, Jun. 2001; 165: 1964-1966.
Albers et al., Design and development process of a humanoid robot upper body through experimentation, 2004, IEEE, p. 77-92 (Year: 2004).
Crystal Eyes, http://www.reald.com, 2007 (Stereo 3D visualization for CAVEs, theaters and immersive environments), 1 pg.
Definition of Individually. Dictionary.com, retrieved on Aug. 9, 2016; Retrieved from the Internet: <http://www.dictionary.com/browse/individually>, 1 page.
Glukhovsky et al., "The development and application of wireless capsule endoscopy," Int. J. Med. Robot. Comput. Assist. Surgery, 2004; 1(1): 114-123.
Gong et al., "Wireless endoscopy," Gastrointestinal Endoscopy 2000; 51 (6): 725-729.
Gopura et al., Mechanical designs of active upper-limb exoskeleton robots: State-of-the-art and design difficulties, 2009, IEEE, p. 178-187 (Year: 2009).
Gopura et al., A brief review on upper extremity robotic exoskeleton systems, 2011, IEEE, p. 346-351 (Year: 2011).
Guo et al., "Micro Active Guide Wire Catheter System- Characteristic Evaluation, Electrical Model* and Operability Evaluation of Micro Active Catheter," Proceedings of the 1996 IEEE International Conference on Robotics and Automation, Apr. 1996; 2226-2231.
Guo et al., "Fish-like Underwater Microrobot with 3 DOF," Proceedings of the 2002 IEEE International Conference on Robotics & Automation, May 2002; 738-743.
Hanly et al., "Robotic Abdominal Surgery," The American Journal of Surgery, 2004; 188 (Suppl. to Oct. 1994); 19S-26S.
Hanly et al., "Value of the SAGES Learning Center in introducing new technology," Surgical Endoscopy, 2004; 19(4): 477-483.
Heikkinen et al., "Comparison of laparoscopic and open Nissen fundoplication two years after operation: A prospective randomized trial," Surgical Endoscopy, 2000; 14:1019-1023.
Hissink, "Olympus Medical develops capsule camera technology," Dec. 2004, accessed Aug. 29, 2007, http://www.letsgodigital.org, 3 pp.
Horgan et al., "Technical Report: Robots in Laparoscopic Surgery," Journal of Laparoendoscopic & Advanced Surgical Techniques, 2001; 11(6): 415-419.
Ishiyama et al., "Spiral-type Micro-machine for Medical Applications," 2000 International Symposium on Micromechatronics and Human Science, 2000; 65-69.
Jagannath et al., "Peroral transgastric endoscopic ligation of fallopian tubes with long-term survival in a porcine model," Gastrointestinal Endoscopy, 2005; 61 (3): 449-453.
Kalloo et al., "Flexible transgastric peritoneoscopy: a novel approach to diagnostic and therapeutic interventions in the peritoneal cavity," Gastrointestinal Endoscopy, 2004; 60(1): 114-117.
Kang et al., "Robotic Assistants Aid Surgeons During Minimally Invasive Procedures," IEEE Engineering in Medicine and Biology, Jan.-Feb. 2001: 94-104.
Kantsevoy et al., "Transgastric endoscopic splenectomy," Surgical Endoscopy, 2006; 20: 522-525.
Kantsevoy et al., "Endoscopic gastrojejunostomy with survival in a porcine model," Gastrointestinal Endoscopy, 2005; 62(2): 287-292.
Kazemier et al. (1998), "Vascular Injuries During Laparoscopy," J. Am. Coli. Surg. 186(5): 604-5.
Keller et al., Design of the pediatric arm rehabilitation robot ChARMin, 2014, IEEE, p. 530-535 (Year: 2014).
Kim, "Early Experience with Telemanipulative Robot-Assisted Laparoscopic Cholecystectomy Using da Vinci," Surgical Laparoscopy, Endoscopy & Percutaneous Techniques, 2002; 12(1): 33-40.
Ko et al., "Per-Oral transgastric abdominal surgery," Chinese Journal of Digestive Diseases, 2006; 7: 67-70.
Lafullarde et al., "Laparoscopic Nissen Fundoplication: Five-year Results and Beyond," Arch/Surg, Feb. 2001; 136: 180-184.
Leggett et al. (2002), "Aortic injury during laparoscopic Fundoplication," Surg. Endoscopy 16(2): 362.
Li et al. (2000), "Microvascular Anastomoses Performed in Rats Using a Microsurgical Telemanipulator," Comp. Aid. Surg., 5: 326-332.
Liem et al., "Comparison of Conventional Anterior Surgery and Laparoscopic Surgery for Inguinal-hernia Repair," New England Journal of Medicine, 1997; 336 (22):1541-1547.
Lou Cubrich, "A Four-DOF Laparo-Endoscopic Single Site Platform for Rapidly-Developing Next Generation Surgical Robotics", Journal of Medical Robotics Research, vol. 1, No. 4, 2016, 165006-1-165006-15.
Macfarlane et al., "Force-Feedback Grasper Helps Restore the Sense of Touch in Minimally Invasive Surgery," Journal of Gastrointestinal Surgery, 1999; 3: 278-285.
Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.
Mei et al., "Wireless Drive and Control of a Swimming Microrobot," Proceedings of the 2002 IEEE International Conference on Robotics & Automation, May 2002: 1131-1136.
Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.

(56) References Cited

OTHER PUBLICATIONS

Melvin et al., "Computer-Enhanced vs. Standard Laparoscopic Antireflux Surgery," J Gastrointest Surg 2002; 6: 11-16.
Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Menciassi et al., "Shape memory alloy clamping devices of a capsule for monitoring tasks in the gastrointestinal tract," J. Micromech. Microeng, 2005; 15: 2045-2055.
Meron, "The development of the swallowable video capsule (M2A)," Gastrointestinal Endoscopy 2000; 52 6: 817-819.
Micron, http://www.micron.com, 2006, 1/4-inch VGA NTSC/PAL CMOS Digital Image Sensor, 98 pp.
Midday Jeff et al., "Material Handling System for Robotic natural Orifice Surgery,", Proceedings of the 2011 Design of medical Devices Conference, Apr. 12-14, 2011, Minneapolis, MN 4 pages.
Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 7 pp., 2004.
Munro (2002), "Laparoscopic access: complications, technologies, and techniques," Curro Opin. Obstet. Gynecol., 14 (4): 365-74.
Nio et al., "Efficiency of manual vs robotical (Zeus) assisted laparoscopic surgery in the performance of standardized tasks," Surg Endosc, 2002; 16: 412-415.
Oleynikov et al., "In Vivo Camera Robots Provide Improved Vision for Laparoscopic Surgery," Computer Assisted Radiology and Surgery (CARS), Chicago, IL, Jun. 23-26, 2004b.
Oleynikov et al., "Miniature Robots Can Assist in Laparoscopic Cholecystectomy," Journal of Surgical Endoscopy, 19-4: 473-476, 2005.
Oleynikov et al., "In Vivo Robotic Laparoscopy," Surgical Innovation, Jun. 2005, 12(2): 177-181.
O'Neill, "Surgeon takes new route to gallbladder," The Oregonian, Jun. 2007; 2 pp.
Orlando et al. (2003), "Needle and Trocar Injuries in Diagnostic Laparoscopy under Local Anesthesia: What Is the True Incidence of These Complications?" Journal of Laparoendoscopic & Advanced Surgical Techniques, 13(3): 181-184.
Palm. William. "Rapid Prototyping Primer" May 1998 (revised Jul. 30, 2002) (http://www.me.psu.edu/lamancusa/rapidpro/primer/chapter2.htm), 12 pages.
Tendick et al., "Applications of Micromechatronics in Minimally Invasive Surgery," IEEE/ASME Transactions on Mechatronics, 1998; 3(1): 34-42.
Thomann et al., "The Design of a new type of Micro Robot for the Intestinal Inspection," Proceedings of the 2002 IEEE Intl. Conference on Intelligent Robots and Systems, Oct. 2002: 1385-1390.
U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617, filed Feb. 22, 2008.
Worn et al., "Espirit Project No. 33915: Miniaturised Robot for Micro Manipulation (MINIMAN)," Nov. 1998, http://www.ipr.ira.ujka.de/-microbot/miniman.
Way et al., editors, "Fundamentals of Laparoscopic Surgery," Churchill Livingstone Inc., 1995; 14 pp.
Wolfe et al. (1991), Endoscopic Cholecystectomy: An analysis of Complications, Arch. Surg. 1991; 126: 1192-1196.
Xu et al., "System Design of an Insertable Robotic Effector Platform for Single Access (SPA) Surgery", The 2009 IEEE/RSJ International Conference on Intelligent Robots and Systems, Oct. 11-15, 2009, St. Louis MO USA pp. 5546-5552.
Yu, BSN, RN, "M2ATM Capsule Endoscopy a Breakthrough Diagnostic Tool for Small Intestine Imagining, "vol. 25, No. 1, 2001, Gastroenterology Nursing, pp. 24-27.
Yu et al., "Microrobotic Cell Injection," Proceedings of the 2001 IEEE International Conference on Robotics and Automation, May 2001: 620-625.
Park et l., "Experimental studies of transgastric gallbladder surgery: choecystectomy and cholecystgastric anastomosis (videos)," Gastrointestinal Endoscopy, 2005; 61 (4): 601-606.
Park et al., "Trocar-less Instrumentation for Laparoscopy: Magnetic Positioning of Intra-abdominal Camera and Retractor," Ann Surg, Mar. 2007; 245(3): 379-384.
Patronik et al., "Crawling on the Heart: A Mobile Robotic Device for Minimally Invasive Cardiac Interventions," MICCAI, 2004, pp. 9-16.
Patronik et al., "Development of a Tethered Epicardial Crawler for Minimally Invasive Cardiac Therapies,", IEEE, pp. 239-240, 2004.
Patronik et al., "Preliminary evaluation of a mobile robotic device for navigation and intervention on the beating heart," Computer Aided Surgery, 10(4): 225-232, Jul. 2005.
Peirs et al., "A Miniature manipulator for integration in a self-propelling endoscope," Sensors and Actuators A, 2001, 92: 343-349.
Peters, "Minimally Invasive Colectomy: Are the Potential Benefits Realized?" Dis Colon Rectum 1993; 36: 751-756.
Phee et al., "Development of Microbotic Devices for Locomotion in the Human Gastrointestinal Tract," International Conference on Computational Intelligence, Robotics and Autonomous Systems (CI RAS 2001), Nov. 28-30, (2001), Singapore, 6 pages.
Phee et al., "Analysis and Development of Locmotion Devices for the Gastrointestinal Tract," IEEE Transaction on Biomedical Engineering, vol. 49, No. 6, Jun. 2002: 613-616.
Platt et al., "In Vivo Robotic Cameras can Enhance Imaging Capability During Laparoscopic Surgery," from the Proceedings of the Society of American Gastrointestinal Endoscopic Suregons (SAGES) Science Conference, Ft. Lauderdale, FL, Apr. 13-16, 2005; 1 pg.
Qian Hunan et al., "Multi-joint Single-wound Minimally Invasive Abdominal Surgery Robot Design," Mechanical Design and Manufacturing, May 8, 2014, pp. 134-137.
Rentschler et al., "Theoretical and Experimental Analysis of In Vivo Wheeled," ASME Design Engineering Technical Conferences: 28th Biennial Mechanisms and Robotics Conference, Salt Lake City, Utah, Sep. 28-Oct. 2, 2004; pp. 1-9.
Rentschler et al., "In Vivo Robots for Laparoscopic Surgery," Studies in Health Technology and Infonnatics—Medicine Meets Virtual Reality, ISO Press, Newport Beach, CA, 2004a, 98: 316-322.
Rentschler et al., "Toward In Vivo Mobility," Studies in Health Technology and Infonnatics—Medicine Meets Virtual Reality, ISO Press, Long Beach, CA, 2005a, III: 397-403.
Rentschler et al., "Mobile In Vivo Robots Can Assist in Abdominal Exploration," from the Proceedings of the Society of American Gastrointestinal Endoscopic Suregons (SAGES) Science Conference, Ft. Lauderdale, FL, Apr. 13-16, 2005b.
Rentschler et al., "Modeling, Analysis, and Experimental Study of In Vivo Wheeled Robotic Mobility," IEEE Transaction on Robotics, 22 (2): 308-321, 2005c.
Rentschler et al., "Miniature in vivo robots for remote and harsh enviroments," IEEE Transaction on Information Technology in Biomedicine, Jan. 2006; 12(1): pp. 66-75.
Rentschler et al., "Mechanical Design of Robotic In Vivo Wheeled Mobility," ASME Journal of Mechanical Design, 2006a; pp. 1-11, Accepted.
Rentschler et al., "Mobile in Vivo Camera Robots Provide Sole Visual Feedback for Abdominal Exploration and Cholecystectomy," Journal of Surigical Endoscopy, 20-1: 135-138, 2006b.
Rentschler et al., "Natural Orifice Surgery with an Endoluminal Mobile Robot," The Society of American Gastrointestinal Endoscopic Suregons, Dallas, TX, Apr. 2006d.

(56) References Cited

OTHER PUBLICATIONS

Rentschler et al., "Mobile In Vivo Biopsy and Camera Robot," Studies in Health and Infonnatics Medicine Meets Virtual Reality, vol. 119: 449-454, IOS Press, Long Beach, CA, 2006e.

Rentschler et al., "Mobile In Vivo Biopsy Robot," IEEE International Conference on Robotics and Automation, Orlando, Florida, May 2006; 4155-4160.

Rentschler et al., "In vivo Robotics during the NEEMO 9 Mission," Medicine Meets Virtual Reality, Feb. 2007; 1 pg.

Rentschler et al., "An In Vivo Mobile Robot for Surgical Vision and Task Assistance," Journal of Medical Devices, Mar. 2007; vol. 1: 23-29.

Riviere et al., "Toward Active Tremor Canceling in Handheld Microsurgical Instruments," IEEE Transaction on Robotics and Automation, Oct. 2003, 19(5): 793-800.

Rosen et al., "Force Controlled and Teleoperated Endoscopic, Grasper for Minimally Invasive Surgery-Experimental Performance Evaluation," IEEE Transactions of Biomedical Engineering, Oct. 1999; 46(10): 1212-1221.

Rosen et al., "Task Decomposition of Lapraoscopic Surgery for Objective Evaluation of Surgical Residents' Learning Curve Using Hidden Markov Model," Computer Aided Surgery, vol. 7, pp. 49-61, 2002.

Rosen et al., "The Blue DRAGON—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.

Rosen et al., Objective Evaluation of Laparoscopic Skills Based on Haptic Information and Tool/Tissue Interactions, Computer Aided Surgery, vol. 7, Issue 1, pp. 49-61, Jul. 2002.

Rosen et al., "Spherical Mechanism Analysis of Surgical Robot for Minimally Invasive Surgery—Analytical and Experimental Approaches," Studies in Health Technology and Infonnatics-Medicine Meets Virtual Reality, pp. 442-448, Jan. 2005.

Ruurda et al., "Feasibility or Robot-Assisted Laparoscopic Surgery," Surgical Laparoscoy, Endoscopy & Percutaneous Techniques, 2002; 12(1):41-45.

Ruurda et al, "Robot-Assisted surgical systems: a new era in laparoscopic surgery," Ann R. Coll Surg Engl. 2002; 84: 223-226.

Sackier et al., "Robotically assisted laparoscopic surgery," Surgical Endoscopy, 1994; 8:63-6.

Salky, "What is the penetration of Endoscopic Techniques into Surgical Practice?" Digestive Surgery 2000; 17:422-426.

Satava, "Surgical Robotics: The Early Chronicles," Surgical Laparoscopy, Endoscopy & Percutaneous Techniques, 2002; 12(1):6-16.

Schippers et al. (1996), "Requirements and Possbilities of Computer-Assisted Endoscopic Surgery," In: Computer Integrated Surgery: Technology and Clinical Applications, pp. 561-565.

Schurr et al., "Robotics and Telemanipulation Technologies for Endoscopic Surgery," Surgical Endoscopy, 2000; 14:375-381.

Schwartz, "In the Lab: Robots that Slink and Squirm," The New York Times, Mar. 27, 2007, 4 pp.

Sharp LL-151-3D, http://www.sharp3d.com, 2006, 2 pp.

Slatkin et al., "The Development of a Robotic Endoscope," Proceedings of the 1995 IEEE International Conference on Robotics and Automation, pp. 162-71, 1995.

Smart Pill "Fastastic Voyage: Smart Pill to Expand Testing," http://www.smartpilldiagnostics.com, Apr. 13, 2005, 1 pg.

Sodeyama et al., A shoulder structure of muscle-driven humanoid with shoulder blades, 2005, IEEE, pg. 1-6 (Year: 2005).

Southern Surgeons Club (1991), "A prospective analysis of 1518 laparoscopic cholecystectomies," N. Eng. 1 Med. 324(16): 1073-1078.

Stefanini et al., "Modeling and Experiments on a Legged Microbot Locomoting in a Tubular Compliant and Slippery Environment," Int. Journal of Robotics Research, vol. 25, No. 5-6, pp. 551-560, May-Jun. 2006.

Stiff et al., "Long-term Pain: Less Common After Laparoscopic than Open Cholecystectomy," British Journal of Surgery, 1994; 81: 1368-1370.

Strong et al., "Efficacy of Novel Robotic Camera vs. a Standard Laproscopic Camera," Surgical Innovation vol. 12, No. 4, Dec. 2005, Westminster Publications, Inc., pp. 315-318.

Suzumori et al., "Development of Flexible Microactuator and its Applications to Robotics Mechanisms," Proceedings of the IEEE International Conference on Robotics and Automation, 1991: 1622-1627.

Taylor et al., "A Telerobotic Assistant for Laparoscopic Surgery," IEEE Eng Med Biol, 1995; 279-87.

Tendick et al. (1993), "Sensing and Manipulation Problems in Endoscopic Surgery: Experiment, Analysis, and Observation," Presence 2(1): 66-81.

\* cited by examiner

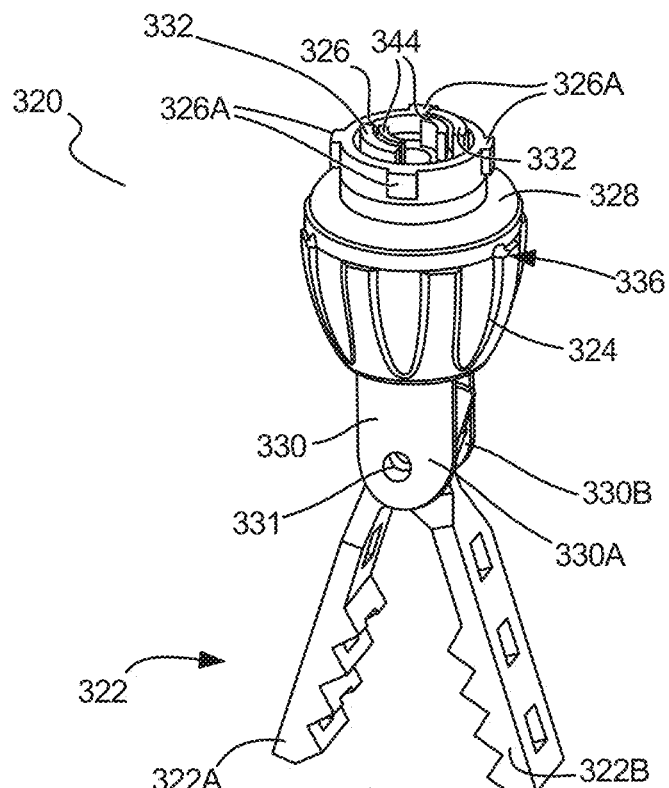
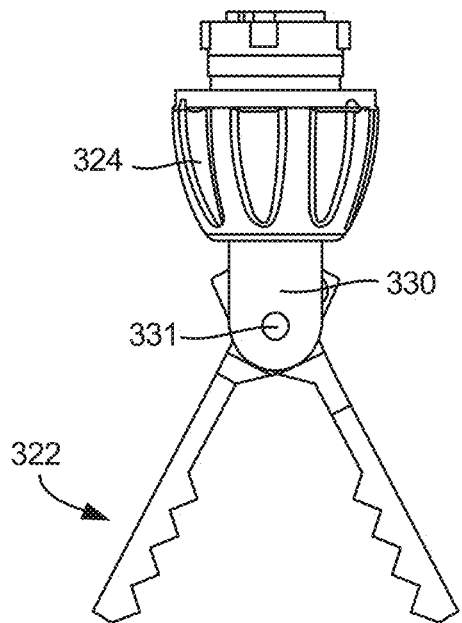
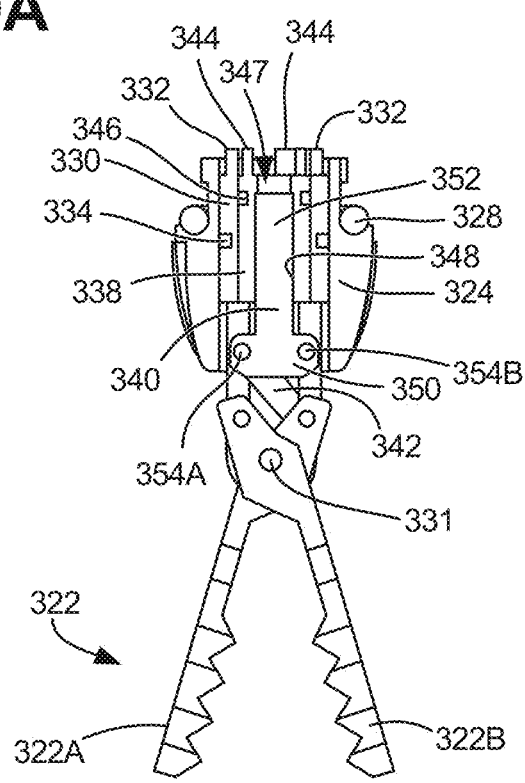
FIG. 9A
FIG. 9B
FIG. 9C

ROBOTIC DEVICE WITH COMPACT JOINT DESIGN AND AN ADDITIONAL DEGREE OF FREEDOM AND RELATED SYSTEMS AND METHODS

CROSS-REFERENCE TO RELATED APPLICATION(S)

This application claims priority as a continuation of U.S. application Ser. No. 15/691,087, filed Aug. 30, 2017, and entitled "Robotic Device with Compact Joint Design and an Additional Degree of Freedom and Related Systems and Methods," which claims the benefit under 35 U.S.C. § 119(e) to U.S. Provisional Application 62/381,299, filed Aug. 30, 2016, and entitled "Robotic Device with Compact Joint Design and an Additional Degree of Freedom and Related Systems and Methods, all of which are hereby incorporated herein by reference in their entireties.

GOVERNMENT SUPPORT

This invention was made with government support under Grant No. W81XWH-14-1-0058, awarded by the U.S. Army Medical Research Acquisition ACT. Grant No. W81XWH-09-2-0185, awarded by the U.S. Army Medical Research and Materiel Command; Grant No. DGE1041000, awarded by the National Science Foundation; Grant No. NNX09A071A, awarded by the National Aeronautics and Space Administration; and Grant No. NNX10AJ26G, awarded by the National Aeronautics and Space Administration. The government has certain rights in the invention.

FIELD OF THE INVENTION

The embodiments disclosed herein relate to various medical devices and related components, including robotic and/or in vivo medical devices and related components, such as arms and end effectors, having a compact joint design. More specifically, certain embodiments include various robotic medical devices, including robotic devices that are disposed within a body cavity and/or disposed through an orifice or opening in the body cavity with such a compact joint design that results in three degrees of freedom. Additional embodiments relate to various robotic device arms and/or medical device operational components, often referred to as "end effectors." Certain arm and/or end effector embodiments disclosed herein relate to forearms having grasper and/or cautery end effectors. Further embodiments relate to methods of operating the above devices and operational components.

BACKGROUND OF THE INVENTION

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, CA) are also restricted by the access ports, as well as having the additional disadvantages of being very large, very expensive, unavailable in most hospitals, and having limited sensory and mobility capabilities.

There is a need in the art for improved surgical methods, systems, and devices, including improved robotic arms and end effectors for use with the devices.

BRIEF SUMMARY OF THE INVENTION

Discussed herein are various robotic devices having a compact joint design that results from the configuration of the internal components and allows for three degrees of freedom in the arm or other component extending from the compact joint. Also discussed herein are various arms and/or end effectors that can be used with the robotic devices disclosed herein or other known robotic devices.

In Example 1, a robotic device comprises an elongate device body, a first shoulder joint, and a first arm operably coupled to the first shoulder joint. The elongate device body comprises a first driveshaft rotatably disposed within the device body (the first driveshaft having a first lumen defined along a length of the first driveshaft), a second driveshaft rotatably disposed within the first lumen (the second driveshaft having a second lumen defined along a length of the second driveshaft), and a third driveshaft rotatably disposed within the second lumen. The first shoulder joint comprises a conversion body operably coupled to at least one of the first, second, or third driveshafts, and a rotation body rotatable in relation to the conversion body.

Example 2 relates to the robotic device according to Example 1, wherein the conversion body is a yoke body comprises a yoke shaft extending from the yoke body, wherein a longitudinal axis of the yoke shaft is transverse to a longitudinal axis of the first driveshaft, and a yoke opening defined in the yoke shaft.

Example 3 relates to the robotic device according to Example 2, wherein the first driveshaft is operably coupled to the first drive gear and wherein the third driveshaft is rotatably disposed through the yoke opening, the third driveshaft being operably coupled to the third drive gear.

Example 4 relates to the robotic device according to Example 3, wherein the first and third drive gears are rotatably coupled to the rotation body.

Example 5 relates to the robotic device according to Example 1, wherein the second driveshaft is operably coupled to the second drive gear, wherein the second drive gear is rotatably coupled to a first shoulder gear, wherein the first shoulder gear is operably coupled to a second shoulder gear through a first opening in the rotation body, wherein the second shoulder gear is rotatably coupled to a third shoulder gear, wherein the third shoulder gear is operably coupled to a fourth shoulder gear through a second opening in the rotation body, wherein the fourth shoulder gear is rotatably coupled to an output gear.

Example 6 relates to the robotic device according to Example 1, wherein the conversion body is a shoulder housing comprising a top opening defined in the shoulder housing, the top opening comprising at least one coupling feature, and a side opening defined in the shoulder housing.

Example 7 relates to the robotic device according to Example 6, wherein the first driveshaft is operably coupled to the at least one coupling feature on the shoulder housing, whereby rotation of the first driveshaft causes rotation of the shoulder housing.

Example 8 relates to the robotic device according to Example 7, wherein the second driveshaft is disposed through the top opening in the shoulder housing and operably coupled to a second drive gear, wherein the second drive gear is disposed within a cavity in the shoulder housing.

Example 9 relates to the robotic device according to Example 8, wherein the second drive gear is rotatably coupled to a first shoulder gear, wherein the first shoulder gear is operably coupled to the rotation body.

Example 10 relates to the robotic device according to Example 6, wherein the third driveshaft is disposed through the top opening in the shoulder housing and operably coupled to a third drive gear, wherein the third drive gear is disposed within a cavity in the shoulder housing.

Example 11 relates to the robotic device according to Example 10, wherein the third drive gear is rotatably coupled to a second shoulder gear, wherein the second shoulder gear is operably coupled to a third shoulder gear through a first opening in the rotation body, wherein the third shoulder gear is rotatably coupled to a fourth shoulder gear, wherein the fourth shoulder gear is operably coupled to a fifth shoulder gear through a second opening in the rotation body, wherein the fifth shoulder gear is rotatably coupled to an output gear.

In Example 12, a robotic device comprises an elongate device body sized and constructed to be disposable through a port or an incision into a cavity of a patient, a first shoulder joint, and a first arm operably coupled to the output gear. The elongate device body comprises a first driveshaft rotatably disposed within the device body, the first driveshaft comprising a first lumen extending along a length of the first driveshaft, a second driveshaft rotatably disposed within the first lumen such that the second driveshaft is disposed within and coaxial with the first driveshaft, the second driveshaft comprising a second lumen extending along a length of the second driveshaft, and a third driveshaft rotatably disposed within the second lumen such that the third driveshaft is disposed within and coaxial with the second driveshaft. The first shoulder joint comprises a conversion body operably coupled to at least one of the first, second, or third driveshafts, a rotation body rotatable in relation to the conversion body, and an output gear operably coupled with the rotation body, wherein the output gear is rotatable around an axis parallel to a longitudinal axis of the first driveshaft.

Example 13 relates to the robotic device according to Example 12, wherein the first driveshaft is operably coupled to a first drive gear and wherein the third driveshaft is rotatably disposed through an opening in the conversion body, the third driveshaft being operably coupled to a third drive gear.

Example 14 relates to the robotic device according to Example 13, wherein the first and third drive gears are rotatably coupled to the rotation body.

Example 15 relates to the robotic device according to Example 12, wherein the second driveshaft is operably coupled to the second drive gear, wherein the second drive gear is operably coupled to an output gear via at least one shoulder gear.

Example 16 relates to the robotic device according to Example 12, wherein the first driveshaft is operably coupled to the conversion body, whereby rotation of the first driveshaft causes rotation of the conversion body.

Example 17 relates to the robotic device according to Example 12, wherein the second driveshaft is operably coupled to a second drive gear, wherein the second drive gear is rotatably coupled to a first shoulder gear, wherein the first shoulder gear is operably coupled to the rotation body.

Example 18 relates to the robotic device according to Example 12, wherein the third driveshaft is operably coupled to a third drive gear, wherein the third drive gear is operably coupled to an output gear via at least one shoulder gear.

In Example 19, a robotic device comprises an elongate device body sized and constructed to be disposable through a port or an incision into a cavity of a patient, a first shoulder joint, and a first arm operably coupled to the first shoulder joint. The elongate device body comprises a first drivetrain, a second drivetrain, and a third drivetrain. The first drivetrain comprises a first motor, and a first driveshaft operably coupled to the first motor, the first driveshaft rotatably disposed within the device body, the first driveshaft comprising a first lumen extending along a length of the first driveshaft. The second drivetrain comprises a second motor, and a second driveshaft operably coupled to the second motor, the second driveshaft rotatably disposed within the first lumen such that the second driveshaft is disposed within and coaxial with the first driveshaft, the second driveshaft comprising a second lumen extending along a length of the second driveshaft. The third drivetrain comprises a third motor, and a third driveshaft operably coupled to the third motor, the third driveshaft rotatably disposed within the second lumen such that the third driveshaft is disposed within and coaxial with the second driveshaft. The first shoulder joint comprises a conversion body operably coupled to at least one of the first, second, or third driveshafts, and a rotation body rotatable in relation to the conversion body.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 9A is a perspective view of an end effector, according to one embodiment.

FIG. 9B is a side view of the end effector of FIG. 9A, according to one embodiment.

FIG. 9C is a cross-sectional side view of the end effector of FIG. 9A, according to one embodiment.

DETAILED DESCRIPTION

Figures 1A, 1B:
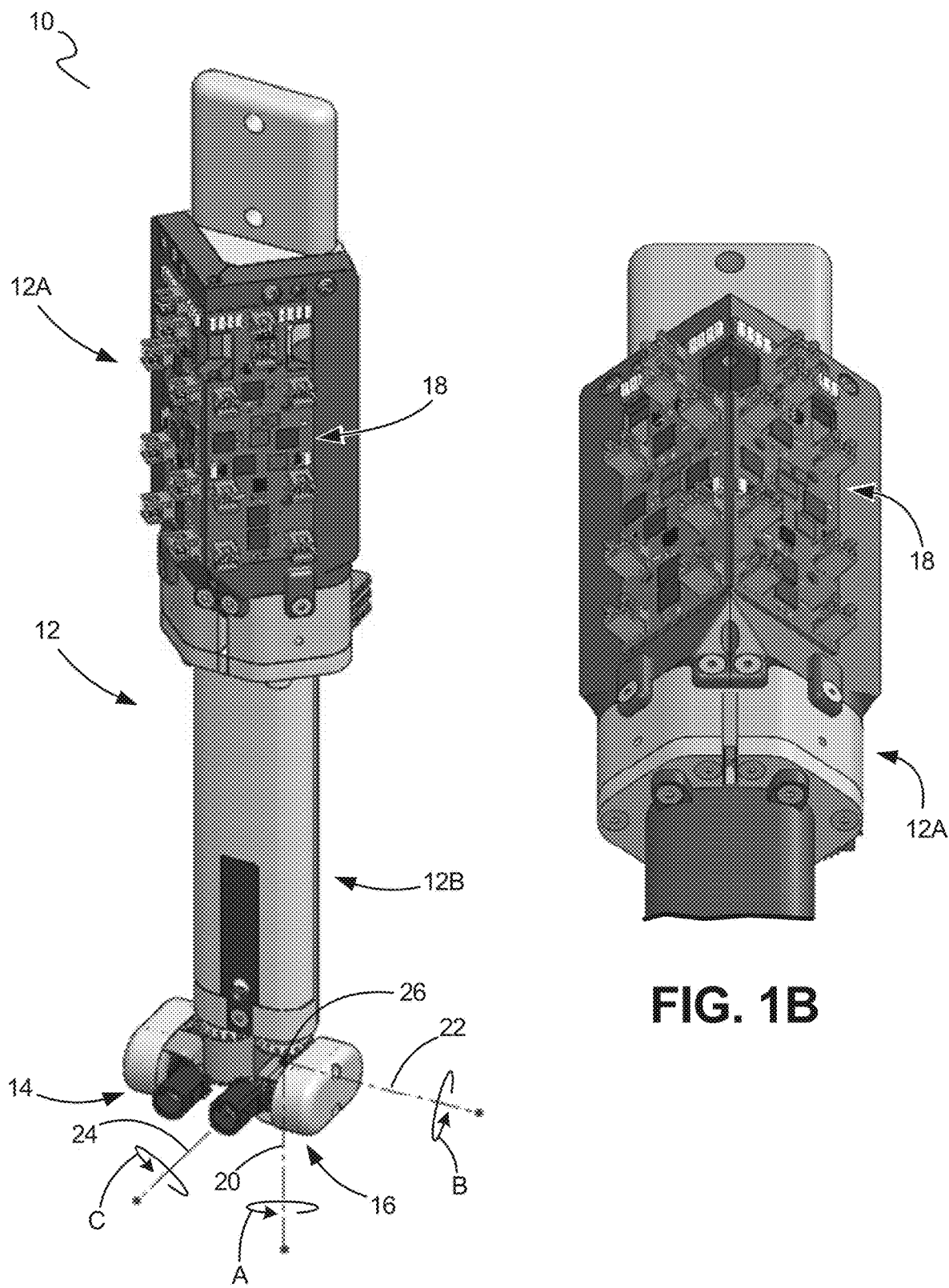
FIG. 1A is a perspective view of a robotic device, according to one embodiment.
FIG. 1B is a perspective view of the motor section of the robotic device of FIG. 1A, according to one embodiment.

The various embodiments disclosed or contemplated herein relate to surgical robotic devices, systems, and methods. More specifically, various embodiments relate to various medical devices, including robotic devices and related methods and systems. Certain implementations relate to such devices for use in laparo-endoscopic single-site (LESS) surgical procedures. Further embodiments relate to certain robotic arms and/or end effectors that can used with the robotic devices, including grasper and/or cautery end effectors.

The robotic devices in these various implementations have a compact joint design as set forth herein, and, in certain embodiments, the arm or other component extending from the joint has at least three degrees of freedom. More specifically, these embodiments have compact shoulder joints with each joint having three nested bevel gear sets that provide three intersecting degrees of freedom, as will be described in additional detail herein. The compact nature of the device results from the three concentric driveshafts that are coupled to and drive the three bevel gear sets at each shoulder. Nesting the three driveshafts of each shoulder within each other as will be described herein enables the three motors that drive the driveshafts (and thus the three bevel gear sets of each shoulder) to be positioned axially along the length of the device body—away from the three gear sets—thereby resulting in a smaller overall circumferential or radial size (width and thickness) of the device body since the motors and driveshafts do not need to be positioned alongside the coupled bevel gear sets.

It is understood that the various embodiments of robotic devices and related methods and systems disclosed herein can be incorporated into or used with any other known medical devices, systems, and methods. For example, the various embodiments disclosed herein may be incorporated into or used with any of the medical devices and systems disclosed in U.S. Pat. No. 8,968,332 (issued on Mar. 3, 2015 and entitled "Magnetically Coupleable Robotic Devices and Related Methods"), U.S. Pat. No. 8,834,488 (issued on Sep. 16, 2014 and entitled "Magnetically Coupleable Surgical Robotic Devices and Related Methods"), U.S. patent application Ser. No. 14/617,232 (filed on Feb. 9, 2015 and entitled "Robotic Surgical Devices and Related Methods"), U.S. Pat. No. 9,579,088 (issued on Feb. 28, 2017 and entitled "Methods, Systems, and Devices for Surgical Visualization and Device Manipulation"), U.S. Pat. No. 8,343,171 (issued on Jan. 1, 2013 and entitled "Methods and Systems of Actuation in Robotic Devices"), U.S. Pat. No. 8,828,024 (issued on Sep. 9, 2014 and entitled "Methods and Systems of Actuation in Robotic Devices"), U.S. patent application Ser. No. 14/454,035 (filed Aug. 7, 2014 and entitled "Methods and Systems of Actuation in Robotic Devices"), U.S. patent application Ser. No. 12/192,663 (filed Aug. 15, 2008 and entitled Medical Inflation, Attachment, and Delivery Devices and Related Methods"), U.S. patent application Ser. No. 15/018,530 (filed Feb. 8, 2016 and entitled "Medical Inflation, Attachment, and Delivery Devices and Related Methods"), U.S. Pat. No. 8,974,440 (issued on Mar. 10, 2015 and entitled "Modular and Cooperative Medical Devices and Related Systems and Methods"), U.S. Pat. No. 8,679,096 (issued on Mar. 25, 2014 and entitled "Multifunctional Operational Component for Robotic Devices"), U.S. Pat. No. 9,179,981 (issued on Nov. 10, 2015 and entitled "Multifunctional Operational Component for Robotic Devices"), U.S. patent application Ser. No. 14/936,234 (filed on Nov. 9, 2015 and entitled "Multifunctional Operational Component for Robotic Devices"), U.S. Pat. No. 8,894,633 (issued on Nov. 25, 2014 and entitled "Modular and Cooperative Medical Devices and Related Systems and Methods"), U.S. Pat. No. 8,968,267 (issued on Mar. 3, 2015 and entitled "Methods and Systems for Handling or Delivering Materials for Natural Orifice Surgery"), U.S. Pat. No. 9,060,781 (issued on Jun. 23, 2015 and entitled "Methods, Systems, and Devices Relating to Surgical End Effectors"), U.S. patent application Ser. No. 14/745,487 (filed on Jun. 22, 2015 and entitled "Methods, Systems, and Devices Relating to Surgical End Effectors"), U.S. Pat. No. 9,089,353 (issued on Jul. 28, 2015 and entitled "Robotic Surgical Devices, Systems, and Related Methods"), U.S. patent application Ser. No. 14/800,423 (filed on Jul. 15, 2015 and entitled "Robotic Surgical Devices, Systems, and Related Methods"), U.S. patent application Ser. No. 13/573,849 (filed Oct. 9, 2012 and entitled "Robotic Surgical Devices, Systems, and Related Methods"), U.S. patent application Ser. No. 13/738,706 (filed Jan. 10, 2013 and entitled "Methods, Systems, and Devices for Surgical Access and Insertion"), U.S. patent application Ser. No. 13/833,605 (filed Mar. 15, 2013 and entitled "Robotic Surgical Devices, Systems, and Related Methods"), U.S. patent application Ser. No. 14/661,465 (filed Mar. 18, 2015 and entitled "Methods, Systems, and Devices for Surgical Access and Insertion"), U.S. Pat. No. 9,498,292 (issued on Nov. 22, 2016 and entitled "Single Site Robotic Devices and Related Systems and Methods"), U.S. patent application Ser. No. 15/357,663 (filed Nov. 21, 2016 and entitled "Single Site Robotic Devices and Related Systems and Methods"), U.S. Pat. No. 9,010,214 (issued on Apr. 21, 2015 and entitled "Local Control Robotic Surgical Devices and Related Methods"), U.S. patent application Ser. No. 14/656,109 (filed on Mar. 12, 2015 and entitled "Local Control Robotic Surgical Devices and Related Methods"), U.S. patent application Ser. No. 14/208,515 (filed Mar. 13, 2014 and entitled "Methods, Systems, and Devices Relating to Robotic Surgical Devices, End Effectors, and Controllers"), U.S. patent application Ser. No. 14/210,934 (filed Mar. 14, 2014 and entitled "Methods, Systems, and Devices Relating to Force Control Surgical Systems), U.S. patent application Ser. No. 14/212,686 (filed Mar. 14, 2014 and entitled "Robotic Surgical Devices, Systems, and Related Methods"), U.S. patent application Ser. No. 14/334,383 (filed Jul. 17, 2014 and entitled "Robotic Surgical Devices, Systems, and Related Methods"), U.S. patent application Ser. No. 14/853,477 (filed Sep. 14, 2015 and entitled "Quick-Release End Effectors and Related Systems and Methods"), U.S. patent application Ser. No. 14/938,667 (filed Nov. 11, 2015 and entitled "Robotic Device with Compact Joint Design and Related Systems and Methods"), U.S. patent application Ser. No. 15/227,813 (filed Aug. 3, 2016 and entitled "Robotic Surgical Devices, Systems, and Related Methods"), U.S. patent application Ser. No. 15/599,231 (filed May 18, 2017 and entitled "Robotic Surgical Devices, Systems, and Related Methods"), U.S. patent application Ser. No. 15/687,113 (filed Aug. 25, 2017 and entitled "Quick-Release End Effector Tool Interface"), U.S. Patent Application 62/425,149 (filed Nov. 22, 2016 and entitled "Improved Gross Positioning Device and Related Systems and Methods"), U.S. Patent Application 62/427,357 (filed Nov. 29, 2016 and entitled "Controller with User Presence Detection and Related Systems and Methods"), U.S. Patent Application 62/433,837 (filed Dec. 14, 2016 and entitled "Releasable Attachment Device for Coupling to Medical Devices and Related Systems and Methods"), and U.S. Pat. No. 7,492,116 (filed on Oct. 31, 2007 and entitled "Robot for Surgical Applications"), U.S. Pat. No. 7,772,796 (filed on Apr. 3, 2007 and entitled "Robot for Surgical Applications"), and U.S. Pat. No. 8,179,073 (issued May 15, 2011, and entitled "Robotic Devices with Agent Delivery Components and Related Methods"), all of which are hereby incorporated herein by reference in their entireties.

Certain device and system implementations disclosed in the applications listed above can be positioned within a body cavity of a patient in combination with the robotic arms and/or end effectors disclosed herein. An "in vivo device" as used herein means any device that can be positioned, operated, or controlled at least in part by a user while being positioned within a body cavity of a patient, including any device that is coupled to a support component such as a rod or other such component that is disposed through an opening or orifice of the body cavity, also including any device positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain embodiments provide for insertion of the present invention into the cavity while maintaining sufficient insufflation of the cavity. Further embodiments minimize the physical contact of the surgeon or surgical users with the present invention during the insertion process. Other implementations enhance the safety of the insertion process for the patient and the present invention. For example, some embodiments provide visualization of the present invention as it is being inserted into the patient's cavity to ensure that no damaging contact occurs between the system/device and the patient. In addition, certain embodiments allow for minimization of the incision size/length. Further implementations reduce the complexity of the access/insertion procedure and/or the steps required for the procedure. Other embodiments relate to devices that have minimal profiles, minimal size, or are generally minimal in function and appearance to enhance ease of handling and use.

Certain implementations disclosed herein relate to "combination" or "modular" medical devices that can be assembled in a variety of configurations. For purposes of this application, both "combination device" and "modular device" shall mean any medical device having modular or interchangeable components that can be arranged in a variety of different configurations. The modular components and combination devices disclosed herein also include segmented triangular or quadrangular-shaped combination devices. These devices, which are made up of modular components (also referred to herein as "segments") that are connected to create the triangular or quadrangular configuration, can provide leverage and/or stability during use while also providing for substantial payload space within the device that can be used for larger components or more operational components. As with the various combination devices disclosed and discussed above, according to one embodiment these triangular or quadrangular devices can be positioned inside the body cavity of a patient in the same fashion as those devices discussed and disclosed above.

An exemplary embodiment of a robotic device 10 is depicted in FIGS. 1A and 1B. As best shown in FIG. 1A, the device 10 has an elongate device body 12, a right shoulder joint 14, and a left shoulder joint 16. While no arms are depicted in FIG. 1A, it is understood that a robotic arm or other component can be coupled to each of the right and left shoulder joints 14, 16. The main body 12 has a motor section 12A and a shaft section 12B, wherein the motors (discussed below) are disposed in the motor section 12A and the elongate driveshafts (discussed below) are disposed in the shaft section 12B. In one embodiment, the control electronics 18 (circuit boards, processors, etc.) are disposed on an outer surface of the motor section 12A as best shown in both FIG. 1A and FIG. 1B. It is understood that, according to some implementations, a cover (not shown) will be positioned over the top of the control electronics 18.

As will be discussed in additional detail below, each of the nested or compact shoulder joints 14, 16 provides three intersecting degrees of freedom. As an example, the left shoulder joint 16 has three intersecting degrees of freedom as shown in FIG. 1A. The first degree of freedom is depicted at arrow A, which represents rotation around the axis 20 parallel to the longitudinal axis of the device body 12, which causes any arm (not shown) coupled to the shoulder 16 to rotate about that axis 20, thereby moving left and right in relation to the device body 12 ("yaw"). The second degree of freedom is depicted at arrow B, which represents rotation around the axis 22 perpendicular to the longitudinal axis of the device body 12, which causes any arm (not shown) coupled to the shoulder 16 to rotate about that axis 22, thereby moving "up and down" in relation to the device body 12 ("pitch"). More specifically, if the device body 12 were laid on a flat plane along its longitudinal axis, the arm (not shown) would move into and out of the flat plane. The third degree of freedom is depicted at arrow C, which represents rotation around the axis 24 that causes any arm (not shown) coupled to the shoulder 16 to rotate around it's own longitudinal axis (or "roll"). These three degrees of freedom are intersecting because all three axes of rotation intersect at a single point 26, as shown in FIG. 1A. While this description above relates to the left shoulder joint 16, it is understood that the right shoulder joint 14 also has substantially the same three intersecting degrees of freedom.

It should be noted that the third degree of freedom is not limited to actuating an arm to rotate on its own longitudinal axis. Instead, the form of actuation is determined based on the configuration of the arm that is coupled to the shoulder. In certain embodiments, the arm coupled to the shoulder is configured such that the rotation around the axis 24 causes the arm to roll (rotate on its own axis). According to other embodiments as will be described in further detail below, the arm coupled to the shoulder is configured such that the rotation around the axis 24 actuates the elbow of the arm to rotate. In further embodiments, it is understood that the type of actuation that occurs as a result of the rotation around the axis 24 is limited only by the configuration of the arm coupled thereto.

Figure 2:
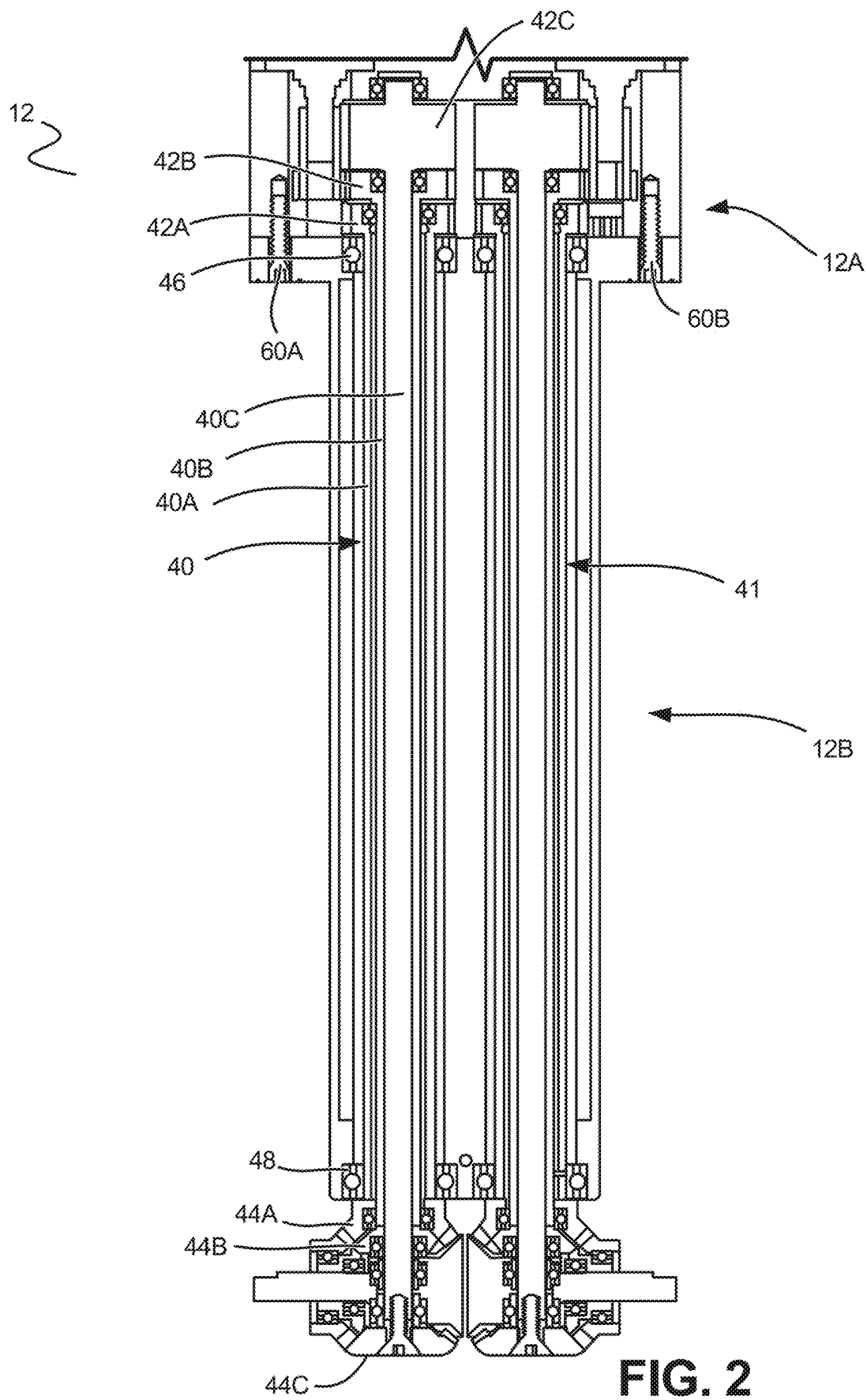
FIG. 2 is a cross-sectional front view of the device body of the robotic device of FIG. 1A, according to one embodiment.

FIG. 2 depicts a cross-sectional front view of the body 12 in which certain internal components of the body 12 are visible, according to one exemplary embodiment. The body 12 has a right set of nested driveshafts 40 and a left set of nested driveshafts 41, wherein both sets are rotatably disposed within the body 12. As set forth herein, the word "nested" is intended to describe components that are concentric such that at least one of the components is positioned inside another of those components and each of the components have a common axis of rotation. In the remainder of this description of the body 12 and its components, the description will focus on the right side of the body 12, the right set of nested driveshafts 40, and components coupled thereto. It is understood that the components of the left side of the body 12, the left set of nested driveshafts 41, the components coupled thereto, the relationship of those components to each other, and their functionality is substantially similar to those components of the right side of the body 12.

With respect to FIG. 2, the right set of nested driveshafts 40 is made up of a first or outer driveshaft 40A, a second or middle driveshaft 40B, and a third or inner driveshaft 40C. The right set of nested driveshafts 40 extend from the motor section 12A into and through the shaft section 12B as shown. The inner driveshaft 40C is rotatably disposed within the middle driveshaft 40B as shown, and has a driven gear 42C fixedly or integrally attached at its proximal end. At its distal end, the inner driveshaft 40C is coupled to a third or lower drive bevel gear 44C. The middle driveshaft 40B is rotatably disposed within the outer driveshaft 40A as shown, and has a driven gear 42B fixedly or integrally attached at its proximal end. At its distal end, the middle driveshaft 40B is coupled to a second or middle drive bevel gear 44B. The outer driveshaft 40A is rotatably disposed on the right side of the body 12 and has a driven gear 42A fixedly or integrally attached at its proximal end. At its distal end, the outer driveshaft 40A is coupled to a first or upper drive bevel gear 44A. The right set of nested driveshafts 40 is supported at its proximal end by first set bearing 46 and at its distal end by second set bearing 48.

In accordance with one embodiment, the shaft section 12B is coupled to the motor section 12A via two or more screws 60A, 60B or other known attachment components or devices. In one embodiment, five screws like screws 60A, 60B are used to couple the shaft 12B and motor 12A sections.

Figure 3A:
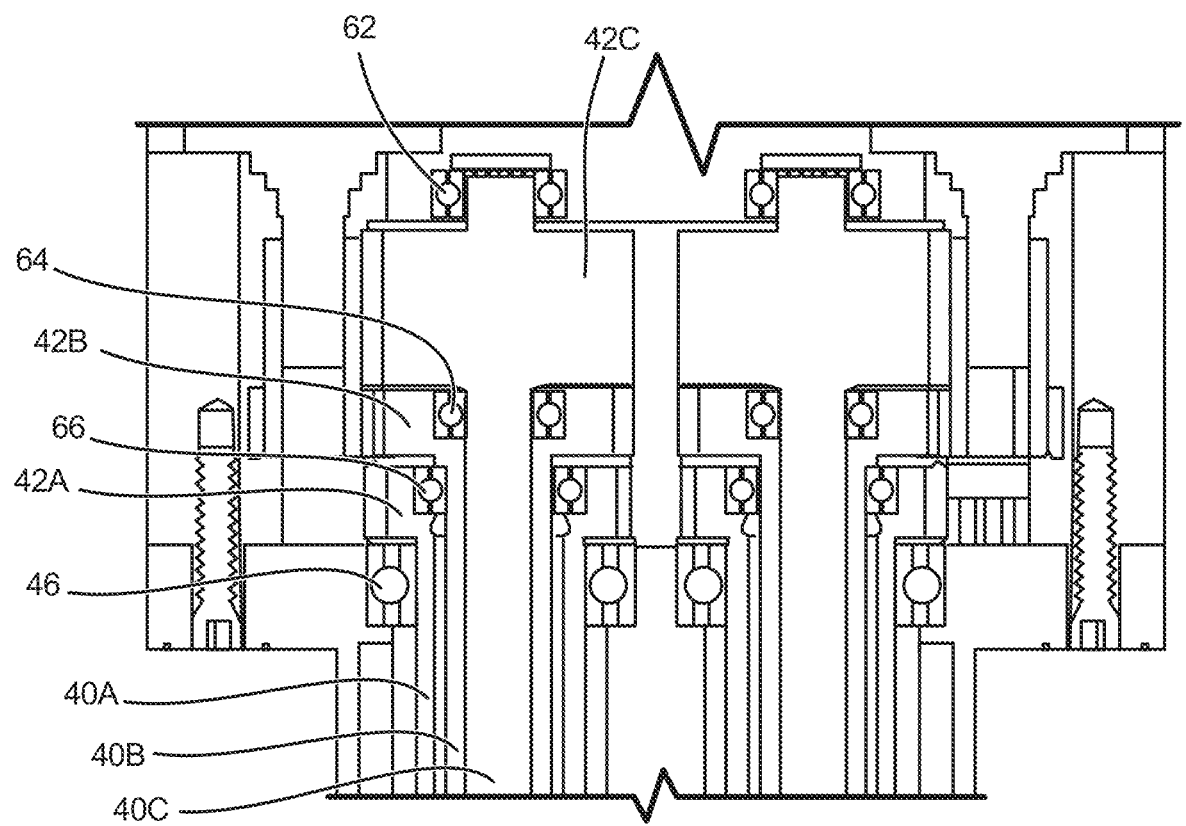
FIG. 3A is a cross-sectional front view of a portion of the device body of the robotic device of FIG. 1, according to one embodiment.
Figure 3B:
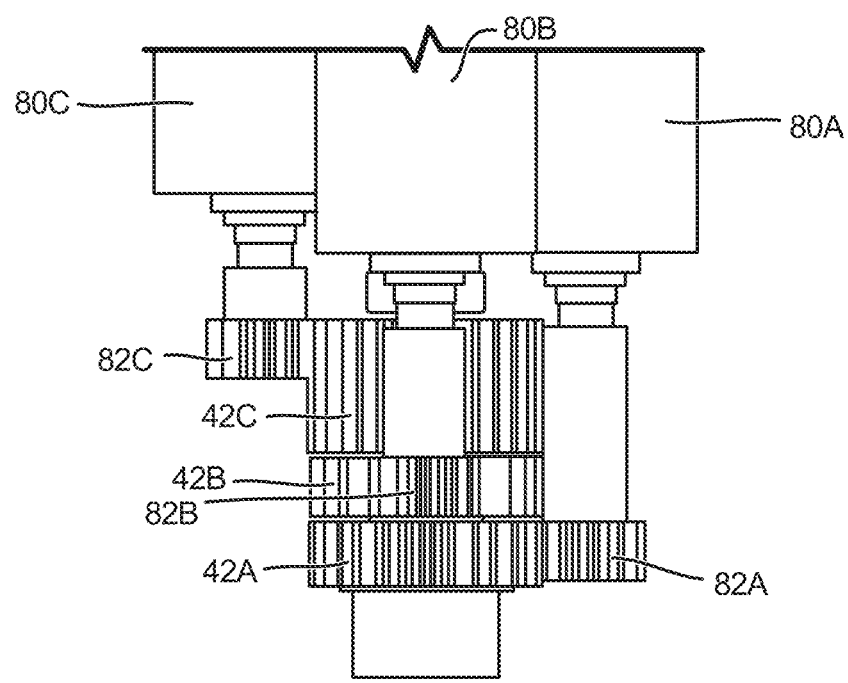
FIG. 3B is a perspective view of certain internal components of the device body of the robotic device of FIG. 1, according to one embodiment.

Expanded views of various internal components at the proximal end of the body 12, including the proximal end of the driveshafts 40A, 40B, 40C and related gears and motors that drive those driveshafts 40A, 40B, 40C, are depicted in FIGS. 3A-3E, according to one embodiment. As best shown in FIG. 3A, the proximal end of the inner driveshaft 40C, including the driven gear 42C, is rotatably supported in the body 12 via a first shaft bearing 62 and a second shaft bearing 64. Further, the proximal end of the middle driveshaft 40B, including driven gear 42B, is rotatably supported in the body 12 via the second shaft bearing 64 and a third shaft bearing 66. In addition, the proximal end of the outer driveshaft 40A, including driven gear 42A, is rotatably supported in the body 12 via the third shaft bearing 66 and the first set bearing 46.

As best shown in FIGS. 3B-3E, each of the sets of nested driveshafts 40, 41 have three motors operably coupled thereto. More specifically, as best shown in the side view of FIG. 3B, motor 80A has a motor drive gear 82A that is coupled to the driven gear 42A (which is coupled to the outer driveshaft 40A). Further, motor 80B has a motor drive gear 82B that is coupled to the driven gear 42B (which is coupled to the middle driveshaft 40B). In addition, motor 80C has a motor drive gear 82C that is coupled to the driven gear 42C (which is coupled to the inner driveshaft 40C). Thus, in operation, the motor 80A can be actuated to drive rotation of the outer driveshaft 40A by driving rotation of motor drive gear 82A, which drives rotation of the driven gear 42A. Similarly, the motor 80B can be actuated to drive rotation of the middle driveshaft 40B by driving rotation of motor drive gear 82B, which drives rotation of the driven gear 42B. In a similar fashion, the motor 80C can be actuated to drive rotation of the inner driveshaft 40C by driving rotation of motor drive gear 82C, which drives rotation of the driven gear 42C.

Figure 3C:
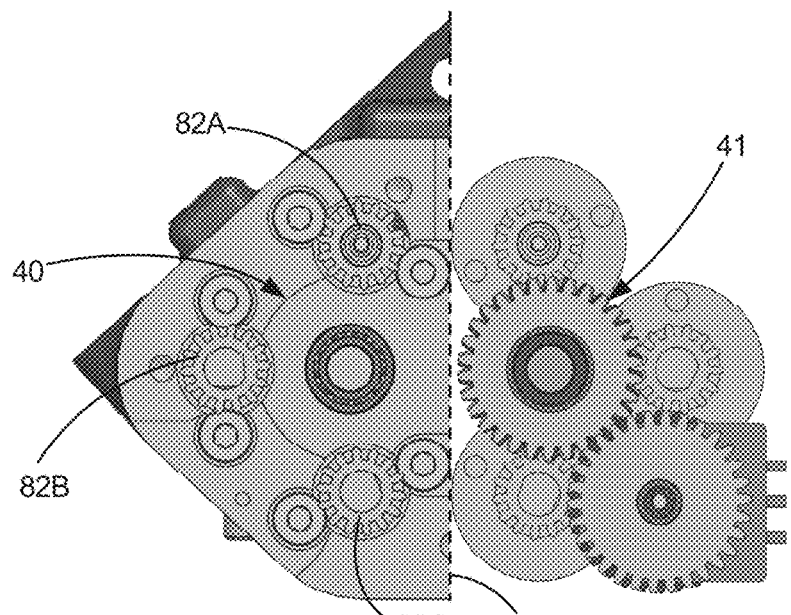
FIG. 3C is a cross-sectional bottom view of certain internal components of the device body of the robotic device of FIG. 1, according to one embodiment.
Figure 3D:
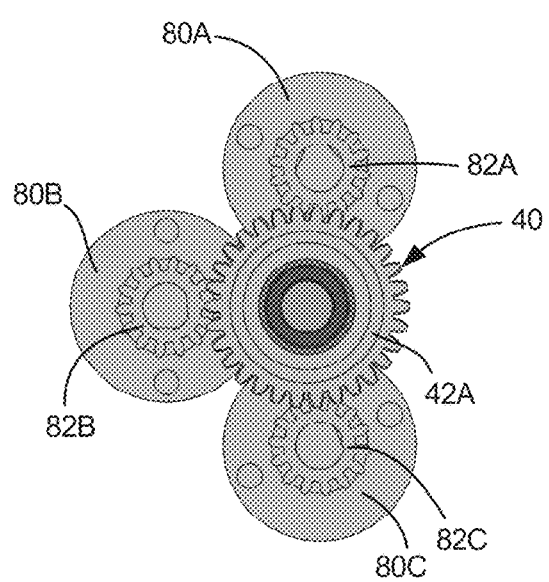
FIG. 3D is a bottom view of certain internal components of the device body of the robotic device of FIG. 1, according to one embodiment.

FIGS. 3C and 3D provide a bottom view of the motors and driveshafts, according to one embodiment. More specifically, FIG. 3C depicts a partial cutaway bottom view of the motor section 12A, in which the outer body of the motor section 12A has been removed on the right half of the section 12A such that the left nested driveshaft shaft set 41 and coupled motors are shown in the cutaway portion of the figure. As can be seen in this figure, the motor section 12A is configured such that the entire section 12A is mirrored across its centerline D as shown in this embodiment. That is, the left side of the motor section 12A and the internal components therein are a mirror image of the right side of the section 12A and its components.

Further, FIG. 3D depicts a bottom view of the right nested driveshaft set 40 and coupled motors, 80A, 80B, 80C, thereby showing the arrangement of the motors 80A, 80B, 80C around the driveshaft set 40.

Figure 3E:
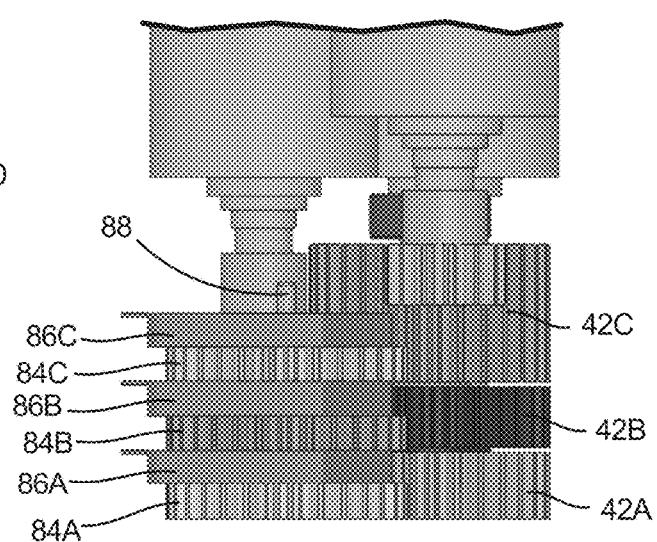
FIG. 3E is a side view of certain internal components of the device body of the robotic device of FIG. 1, according to one embodiment.

In one implementation as shown in FIG. 3E, the driveshafts 40A, 40B, 40C are coupled to potentiometers 86A, 86B, 86C that provide absolute position feedback relating to each driveshaft 40A, 40B, 40C. As shown, the driven gear 42A (of the outer driveshaft 40A) is coupled to potentiometer gear 84A, which is coupled to potentiometer 86A, while driven gear 42B (of the middle driveshaft 40B) is coupled to potentiometer gear 84B, which is coupled to potentiometer 86B. Similarly, driven gear 42C (of the inner driveshaft 40C) is coupled to potentiometer gear 84C, which is coupled to potentiometer 86C. The potentiometer gears 84A, 84B, 84C and potentiometers 86A, 86B, 86C are coupled to a pin 88. In one embodiment, each of the potentiometers 86A, 86B, 86C are single-turn potentiometers. Alternatively, these components 86A, 86B, 86C can be any known sensors or meters for detecting or monitoring position information.

Figure 4A:
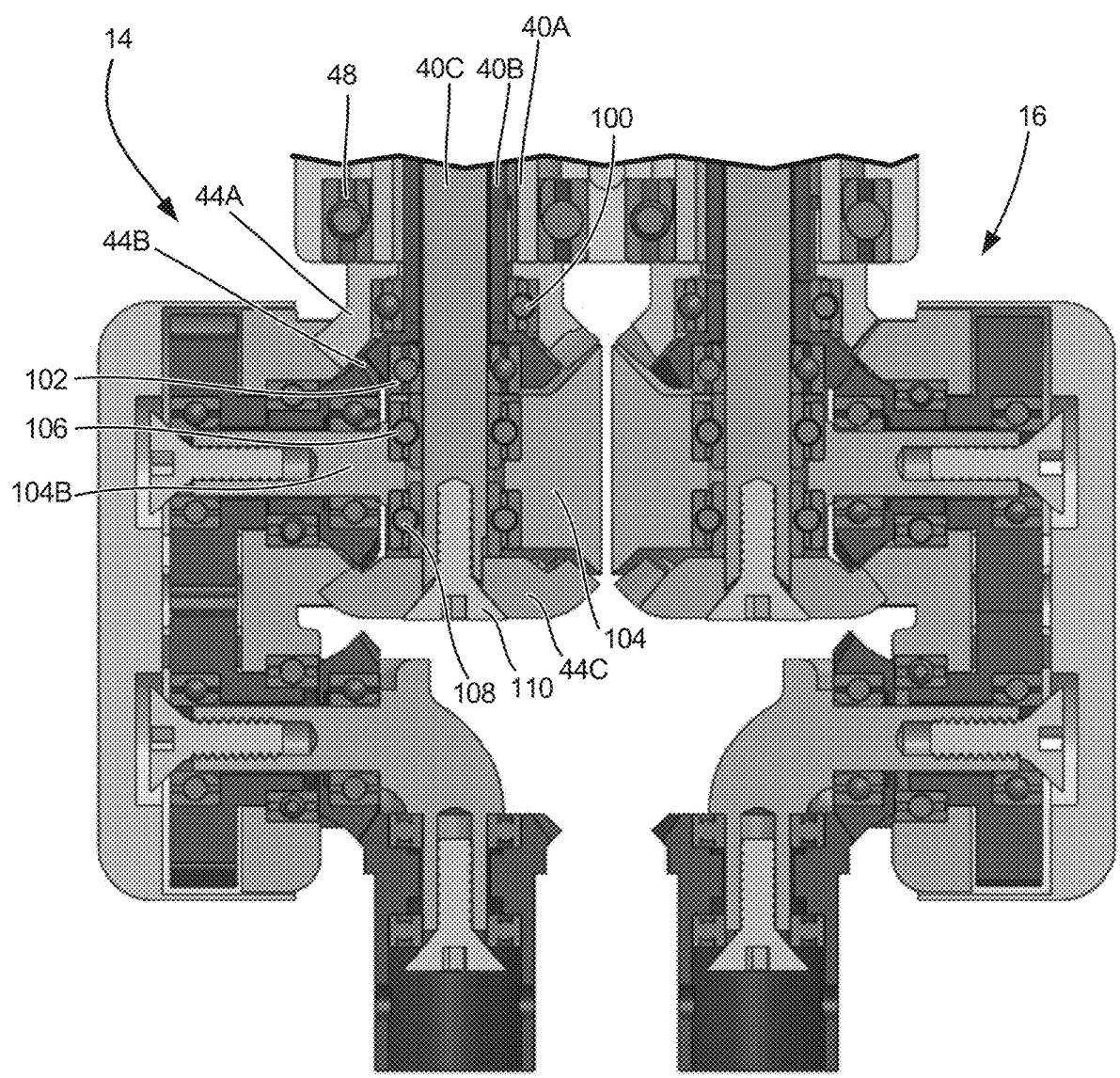
FIG. 4A is a cross-sectional front view of a portion of the device body of the robotic device of FIG. 1, according to one embodiment.
Figure 4B:
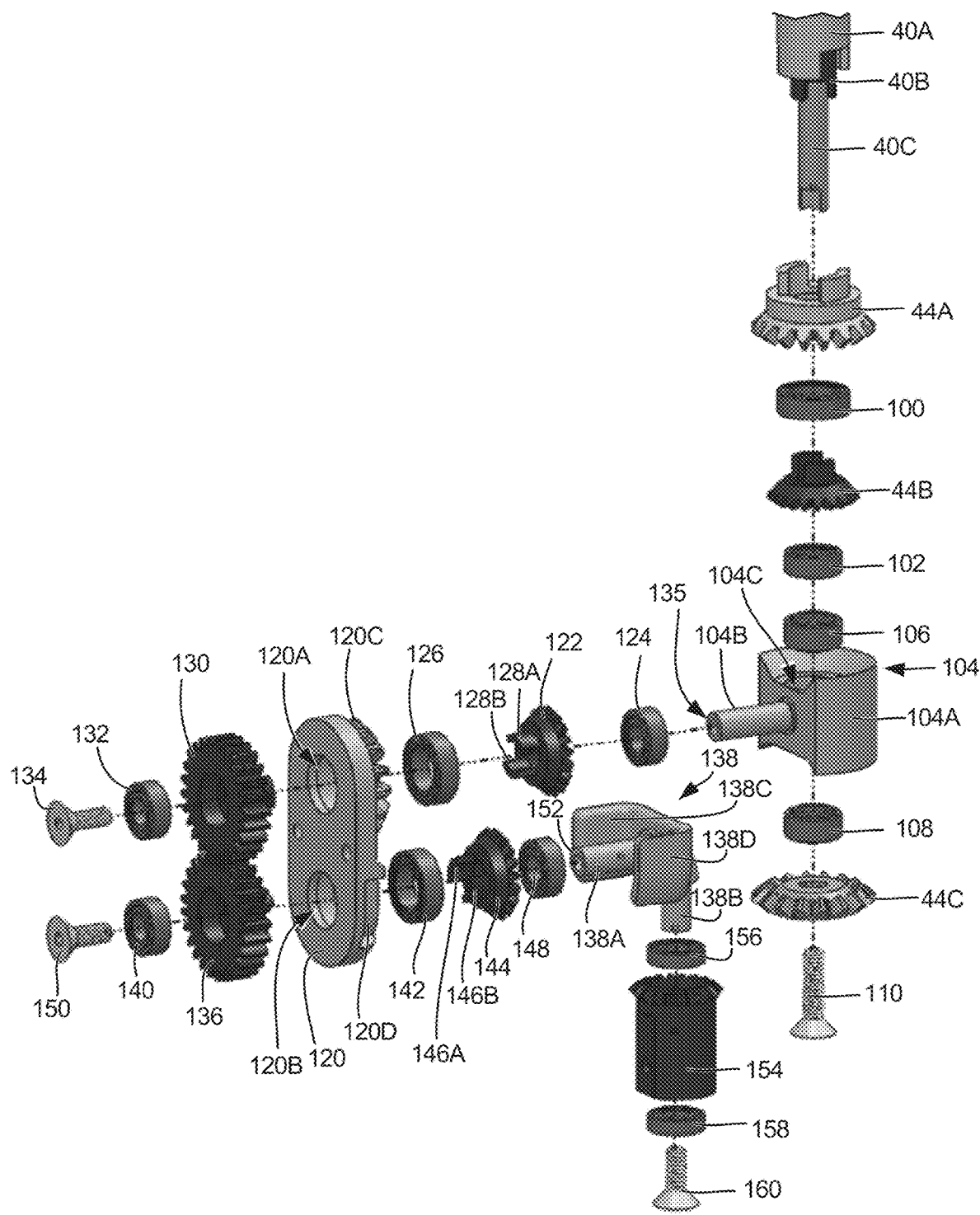
FIG. 4B is a perspective view of various components of the right shoulder joint of the robotic device of FIG. 1, according to one embodiment.

FIGS. 4A and 4B depict the right shoulder joint 14 and its various components, according to one implementation. More specifically, FIG. 4A depicts a cross-sectional front view of the internal components of both the right 14 and 16 shoulder joints, while FIG. 4B depicts an exploded view of the internal components of the right shoulder joint 14. As discussed above, and as shown in both FIGS. 4A and 4B, the outer driveshaft 40A is coupled (or rotationally constrained) to the upper drive bevel gear 44A, while the middle driveshaft 40B is coupled to the middle drive bevel gear 44B, and the inner driveshaft 40C is coupled to the lower drive bevel gear 44C. The outer driveshaft 40A and upper drive bevel gear 44A are supported by the second set bearing 48 and the first shoulder bearing 100, wherein the first shoulder bearing 100 is positioned within the distal end of the bevel gear 44A as best shown in FIG. 4A. The middle driveshaft 40B and the middle drive bevel gear 44B are supported by the first shoulder bearing 100 and the second shoulder bearing 102, wherein the second shoulder bearing 102 is positioned within the distal end of the bevel gear 44B as best shown in FIG. 4A.

The right shoulder 14 also has a differential yoke (also referred to as a "shoulder housing" or "conversion body") 104 (as does the left shoulder 16). As best shown in FIG. 4B, the yoke 104 has a body 104A and a yoke shaft 104B, wherein the body 104A defines a yoke opening 104C. The yoke 104 as shown is configured to be positioned over the inner driveshaft 40C such that the driveshaft 40C is positioned through the yoke opening 104C. The driveshaft 40C is rotatably supported within the yoke opening 104C by the third 106 and fourth 108 shoulder bearings, which are disposed within the opening 104C. As mentioned above, the inner driveshaft 40C is coupled to the lower drive bevel gear 44C. The bevel gears 44A, 44B, 44C, the driveshafts 40A, 40B, 40C, and the bearings 100, 102, 106, 108 are coupled together and "preloaded" by the screw 110 that is coupled to the inner driveshaft 40C. Alternatively, any known attachment component can be used to couple together and preload these components.

Continuing with FIGS. 4A and 4B, the yoke shaft 104B is rotatably coupled to a bevel gear body (also referred to as a "rotatable arm," "rotatable body," "rotation arm," "rotation body," "pitch arm," or "pitch body") 120. The bevel gear body 120 has two openings 120A, 120B defined therein, with a body bevel gear 120C disposed around one side of the opening 120A such that rotation of the bevel gear 120C causes rotation of the bevel gear body 120. The opening 120A is configured to receive the yoke shaft 104B such that the yoke shaft 104B is positioned through the opening 120A. When the bevel gear body 120 is coupled to the yoke shaft 104B, an first inner bevel gear 122 is also positioned over the yoke shaft 104B and is supported by a fifth shoulder bearing 124 and a sixth shoulder bearing 126, wherein the fifth shoulder bearing 124 is disposed within the distal end of the bevel gear 122 and the sixth shoulder bearing 126 is disposed within the body bevel gear 120C.

It is understood that the rotation body 120 can be any component that has two openings as described herein and can be coupled to the various components as described.

The first inner bevel gear 122 is operably coupled to a first spur gear 130 such that rotation of the first inner bevel gear 122 causes rotation of the spur gear 130. The first spur gear 130 is also positioned over the yoke shaft 104B, and the two gears 122, 130 are coupled together through the opening 120A in the bevel gear body 120. In one embodiment, the first inner bevel gear 122 has two projections 128A, 128B that mate with the spur gear 130 to couple the two gears 122, 130 together. Alternatively, any coupling component or mechanism can be used to couple the two gears 122, 130 together. The first spur gear 130 is supported in part by the sixth bearing 126 discussed above and further in part by a seventh shoulder bearing 132, which is disposed within the distal end of the spur gear 130. The bearings 124, 126, 132 all help to support the first inner bevel gear 122, the bevel gear body 120, and the first spur gear 130 such that all three (the bevel gear 122, body 120, and spur gear 130) are rotatable around the yoke shaft 104B. The bearings 124, 126, 132 are preloaded by the countersunk screw 134, which is threaded into a threaded lumen 135 at the end of the yoke shaft 104B.

The first spur gear 130 is rotatably coupled to a second spur gear 136 such that rotation of the first spur gear 130 causes rotation of the second spur gear 136. The second spur gear 136 is positioned over a horizontal shaft 138A of a gear linkage 138 (also referred to herein as an "L-shaft" 138) and is supported in part by an eighth shoulder bearing 140 and a ninth shoulder bearing 142. The eighth shoulder bearing 140 is positioned within the distal end of the second spur gear 136. The second spur gear 136 is operably coupled to a second inner bevel gear 144 such that rotation of the spur gear 136 causes rotation of the bevel gear 144. The second inner bevel gear 144 is also positioned over the horizontal shaft 138A, and the two gears 136, 144 are coupled together through the opening 120B in the bevel gear body 120. As such, the horizontal shaft 138A is also positioned through the opening 120B in the gear body 120.

In one embodiment, the second inner bevel gear 144 has two projections 146A, 146B that mate with the spur gear 136 to couple the two gears 136, 144 together. Alternatively, any coupling component or mechanism can be used to couple the two gears 136, 144 together. The second inner bevel gear 144 is supported in part by the ninth shoulder bearing 142 discussed above and further in part by a tenth shoulder bearing 148, which is disposed within the distal end of the bevel gear 144. The bearings 140, 142, 148 all help to support the second inner bevel gear 144, the bevel gear body 120, and the second spur gear 136 such that all three (the bevel gear 144, body 120, and spur gear 136) are rotatable around the horizontal shaft 138A. The bearings 140, 142, 148 are preloaded by the countersunk screw 150, which is threaded into a threaded lumen 152 at the end of the horizontal shaft 138A.

According to one embodiment, the L-shaft 138 has both the horizontal shaft 138A, as discussed above, and a vertical shaft 138B. As also discussed above, the horizontal shaft 138A receives the second inner bevel gear 144, the bevel gear body 120, and the second spur gear 136, along with the bearings 140, 142, 148, such that all three of the bevel gear 144, gear body 120, and spur gear 136 are disposed on the shaft 183A, with the bevel gear 144 and the spur gear 136 being rotatably disposed on the shaft 138A and the gear body 120 being non-rotatably disposed on the shaft 138A as discussed in further detail below. The vertical shaft 138B receives an output bevel gear 154 that is supported by the eleventh bearing 156 and the twelfth bearing 158 such that the bevel gear 154 is rotatably disposed around the shaft 138B. The bearings 156, 158 are preloaded by the countersunk screw 160, which is threaded into a threaded lumen (not shown) at the end of the shaft 138B.

The L-shaft 138 is coupled to the gear body 120 via two wings 138C, 138D that couple to slots 120D defined in the gear body 120 such that the L-shaft moves when the gear body 120 moves. Alternatively, the L-shaft 138 can be coupled to the body 120 by any known component or mechanism.

In use, the upper drive bevel gear 44A is rotatably coupled to the bevel gear 120C (on the bevel gear body 120) such that rotation of the upper drive bevel gear 44A causes rotation of the bevel gear 120C. Further, the lower drive bevel gear 44C is also rotatably coupled to the bevel gear 120C on bevel gear body 120 such that rotation of the lower drive bevel gear 44C also causes rotation of the bevel gear 120C. As such, the two bevel gears 44A, 44C work together to drive the rotation of the yoke 104 about the driveshaft 40C and the rotation of the bevel gear body 120 about the yoke shaft 104B. In other words, if the two bevel gears 44A, 44C are actuated to rotate in opposite directions, that causes the bevel gear body 120 to rotate about the yoke shaft 104B, and if the two bevel gears 44A, 44C are actuated to rotate in the same direction, that causes the yoke 104 to rotate about the driveshaft 40C. Further, the two gears 44A, 44C can be actuated to do both at the same time.

In addition, the middle drive bevel gear 44B is rotatably coupled to the first inner bevel gear 122 such that rotation of the middle drive bevel gear 44B causes rotation of the first inner bevel gear 122, which causes rotation of the first spur gear 130. Rotation of the first spur gear 130 causes rotation of the second spur gear 136, which causes rotation of the second inner bevel gear 144. The second inner bevel gear 144 is rotatably coupled to the output bevel gear 154 such that rotation of the second inner bevel gear 144 causes rotation of the output bevel gear 154. According to certain implementations, the output bevel gear 154 can be coupled to a robotic arm (not shown) or other component of a robotic device, such that rotation of the output bevel gear 154 causes rotation of the component.

As such, according to certain embodiments, the right shoulder 14 as best shown in FIGS. 2, 4A, and 4B (and the left shoulder 16 as shown in FIG. 1A) has a compact joint design with three degrees of freedom based on three concentric driveshafts (made up of driveshafts 40A, 40B, 40C, as best shown in FIG. 2) and three nested bevel gear sets (made up of bevel gears 44A, 44B, 44C, as best shown in FIGS. 2 and 4A) coupled to those driveshafts. As discussed above and as best shown in FIG. 1A, the three degrees of freedom are intersecting degrees of freedom in certain embodiments. The nested driveshafts 40A, 40B, 40C allow for the motors coupled thereto (motors 80A, 80B, 80C) to be positioned axially at a proximal position along the length of the device body 12 at a distance from the shoulders 14, 16 (and thus the gear sets associated with gears 44A, 44B, 44C), thereby resulting in smaller overall circumferential or radial size (width and thickness) of the device body 12. More specifically, the configuration according to these embodiments results in the motors and driveshafts not having to be positioned axially alongside the bevel gear sets, thereby allowing for a device body 12 having a smaller overall circumferential or radial size (smaller circumference or radius) in relation to any device in which the motors and driveshafts are positioned alongside (at the same length as) the shoulders along the length of the device.

As discussed above in the context of FIG. 1A, each shoulder joint 14, 16 provides three degrees of freedom. In this implementation as best shown in FIGS. 4A and 4B, two of the degrees of freedom—the pitch and yaw of the arms coupled to the shoulders 14, 16—are accomplished via the bevel gears 44A and 44C being coupled to the output bevel gear 120C as described above. Further, the third degree of freedom is accomplished via the bevel gear 44B driving bevel gear 122, which ultimately drives output bevel gear 154 as described above. As discussed in further detail above in relation to FIG. 1A, the actuation resulting from the rotation of output bevel gear 154 depends on the configuration of the arm coupled thereto. In certain embodiments, the rotation of the bevel gear 154 causes roll: rotation of the arm on its longitudinal axis. In some alternative embodiments, including the embodiment discussed below in relation to FIGS. 5A-8B, the rotation of the bevel gear 154 is passed through the shoulder and causes the elbow of the arm to rotate. In further implementations, the rotation of the output bevel gear 154 can actuate the arm in other ways, depending on the arm configuration.

Figure 5A:
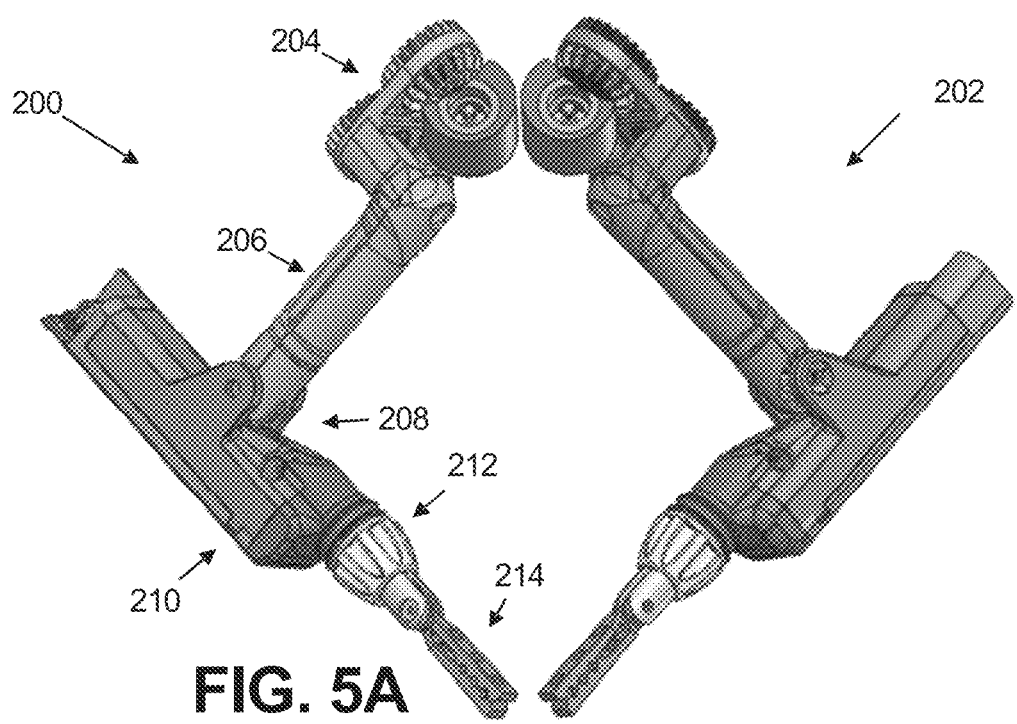
FIG. 5A is a perspective view of an arm of a robotic device, according to one embodiment.
Figure 5B:
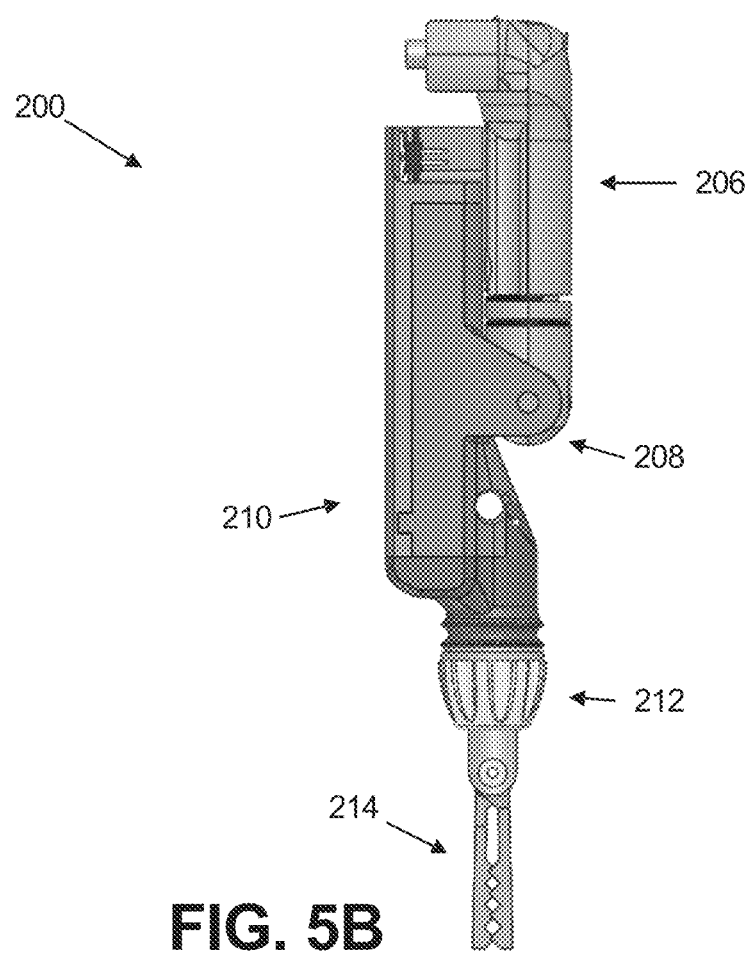
FIG. 5B is a side view of one of the arms of FIG. 5A, according to one embodiment.

In accordance with one implementation as shown in FIGS. 5A and 5B, a robotic arm 200 (or, alternatively, two such arms) is provided that can be coupled to a shoulder of the device 10 embodiment discussed above. Alternatively, this arm 200 can be coupled to any known robotic surgical device. In this specific implementation, the arm 200 is a right arm 200. Note that FIG. 5A depicts both the right arm 200 and a left arm 202. In the remainder of this discussion, the description will focus on the right arm 200. It is understood that the components of the left arm 202, the relationship of those components to each other, and their functionality is substantially similar to those components of the right arm 200.

Continuing with reference to FIGS. 5A and 5B, the right arm 200 has a shoulder joint (also referred to herein as a "shoulder" or "first joint") 204, an upper arm (also referred to as a "first arm link" or "first arm component") 206, an elbow joint (also referred to herein as an "elbow" or "second joint") 208, a forearm (also referred to herein as a "second arm link" or "second arm component") 210, a wrist joint (also referred to herein as a "wrist" or "third joint") 212, and an end effector 214.

In one implementation, the arm 200 (and arm 202) is configured to couple to a shoulder having 3 degrees of freedom ("DOF"), such as the device 10 described herein above. Alternatively, the arm 200 can be coupled with any known robotic device with a shoulder having 3 DOF. In a further alternative, the arm 200 can couple with any known robotic device.

Figure 6A:
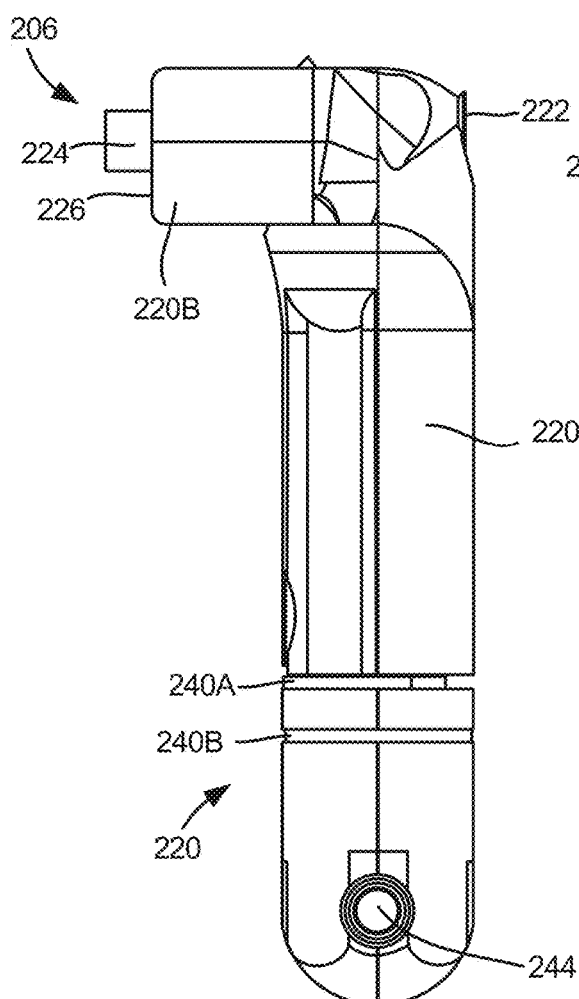
FIG. 6A is a side view of an upper arm of a robotic device, according to one embodiment.
Figure 6B:
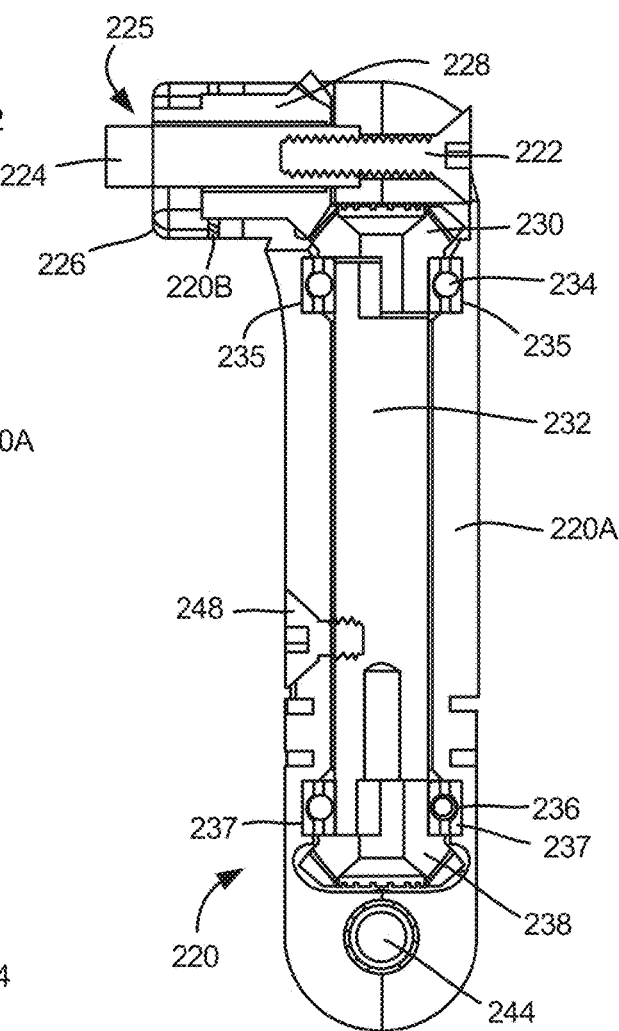
FIG. 6B is a cross-sectional side view of the upper arm of FIG. 6A, according to one embodiment.

The upper arm 206, according to one embodiment, is shown in further detail in FIGS. 6A-6D. The upper arm 206 has a body (also referred to as a "casing," "outer structure," or "shell") 220. In this particular implementation, the body 220 is made up of a first body component 220A and a second body component 220B that are coupled together via the countersunk screw 222 that is coupled to a distal end of a coupling shaft (also referred to as a "cylindrical shaft" or "coupling shaft") 224 (as best shown in FIG. 6B). More specifically, the two body components 220A, 220B are constrained together via the coupling of the screw 222 and the distal end of the shaft 224 such that tightening the screw 222 into the shaft 224 produces clamping forces between the two body components 220A, 220B. The tightening of the coupling between the screw 222 and shaft 224 also causes the shaft 224 to be pulled into a corresponding cylindrical lumen 225 defined in the body component 220B as best shown in FIG. 6B. More specifically, the shaft 224 is positioned within the cylindrical lumen 225 and is urged distally as the screw 222 is tightened into the shaft 224. Alternatively, the body 220 is a single, unitary component. In further alternatives, the body 220 can be made up of three or more different components.

Figure 6C:
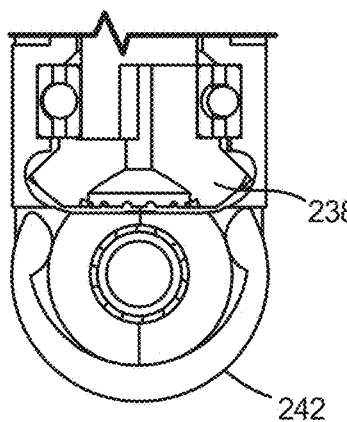
FIG. 6C is a cross-sectional side view of a portion of the upper arm of FIG. 6A, according to one embodiment.
Figure 6D:
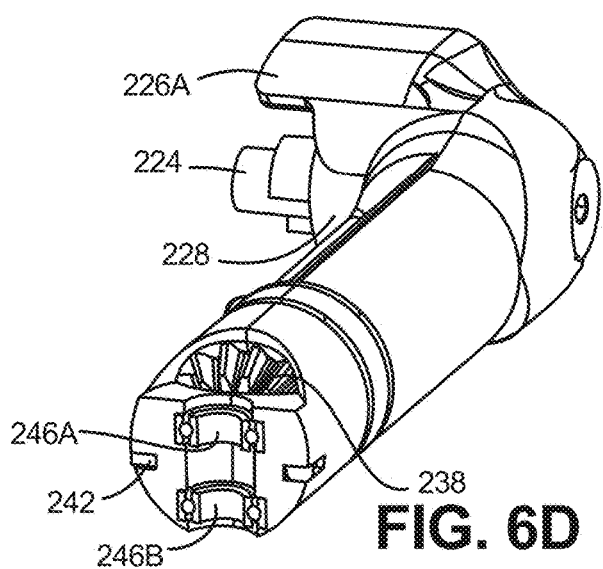
FIG. 6D is a perspective view of the upper arm of FIG. 6A, according to one embodiment.

In this particular embodiment as depicted in which the upper arm 206 is coupled to the shoulder 14 described above, the upper arm 206 is coupled to the shoulder 14 by removing/replacing some of the components of shoulder 14 described above. More specifically, in this particular example, the following components as best shown in FIG. 4B are removed and replaced with components of the upper arm 206: the second inner bevel gear 144, the tenth shoulder bearing 148, the L-shaft gear linkage 138, the eleventh bearing 156, the output bevel gear 154, the twelfth bearing 158, and the countersunk screw 160. Thus, the proximal end 226 of the upper arm 206 is configured to couple with the bevel gear body 120 (as best shown in FIG. 4B) such that the distal end of the coupling shaft 224 extends through the opening 120B in the gear body 120. More specifically, the proximal end 226 has projections 226A as best shown in FIG. 6D that geometrically match with the slots 120D defined in the gear body 120 (as best shown in FIG. 4B) such that the proximal end 226 is coupled to the gear body 120. Alternatively, the proximal end 226 and the gear body 120 can have any feature or configuration that results in geometric matching and thus coupling of the two components. In one embodiment, the coupling shaft 224 and thus the entire upper arm 206 are attached to the gear body 120 via the countersunk screw 150 (as best shown in FIG. 4B), which threadably couples to the distal end of the shaft 224. Further, the upper arm 206 has a first upper arm bevel gear 228 disposed in the proximal end 226 that is rotationally coupled at its proximal end to the second spur gear 136 (as best shown in FIG. 4B) such that rotation of the spur gear 136 causes the bevel gear 228 to rotate. In one embodiment, as best shown in FIG. 6D, the first gear 228 has projections 228A at its proximal end that geometrically match with a feature or component on the spur gear 136, thereby allowing the two gears 228, 136 to couple. Alternatively, the gears 228, 136 can have any configurations that allow them to couple together. While this specific exemplary embodiment relates to the upper arm 206 being coupled to the device 10 described above, it is understood that, according to various alternative embodiments, the first bevel gear 228 can be rotationally coupled to a gear or shaft or other rotational component of any robotic device to which the upper arm 206 is coupled.

Continuing with FIGS. 6A and 6B, the first upper arm bevel gear 228 is constrained and supported by the coupling shaft 224 (which is positioned through the gear 228 such that the gear 228 rotates around the shaft 224) and is mateably coupled to (and further constrained and supported by) a second upper arm bevel gear 230 such that rotation of the first bevel gear 228 causes rotation of the second bevel gear 230. The second bevel gear 230 is rotationally coupled to a driveshaft 232 such that rotation of the bevel gear 230 causes rotation of the driveshaft 232. In one implementation, the gear 230 and driveshaft 232 have geometrical features that allow for the two components to mateably couple in a similar fashion to the gear 228 and spur gear 136, as described above. Alternatively, the gear 230 and driveshaft 232 can be coupled in any known fashion such that rotation of one causes rotation of the other. The driveshaft 232 is supported by first upper arm bearing 234 and second upper arm bearing 236. These bearings 234, 236, according to one embodiment, also function as alignment features to help with alignment and constraint of the first and second body components 220A, 220B. That is, each of the first and second body components 220A, 220B have bearing receiving openings 235, 237 defined within the components 220A, 220B such that the bearings 234, 236 can be positioned therein when the components 220A, 220B are coupled to each other as shown. Thus, assembly and coupling of the two components 220A, 220B are facilitated and aligned by the positioning of the bearings 234, 236 in the bearing receiving openings 235, 237. At its distal end, the driveshaft 232 is rotationally coupled to a third upper arm bevel gear 238 such that rotation of the driveshaft 232 causes rotation of the gear 238. The driveshaft 232 and gear 238 have geometrical features that allow for the two components to mateably couple in a similar fashion to the gear 230 and driveshaft 232 or are coupled in any known fashion such that rotation of one causes rotation of the other, as described above.

The upper arm 206 has a distal opening 244 defined at or near the distal end of the arm 206. As described in further detail below, the distal opening 244 is configured to receive a component of any forearm (such as forearm 210, for example) or other component that is coupled to the upper arm 206 such that the forearm or other component can rotate in relation to upper arm 206. As best shown in FIG. 6D, the opening 244 has two bearings 246A, 246B disposed therein that provide support to the component disposed therethrough, as described below.

According to some implementations, the upper arm 206 has at least one retaining ring that functions to help hold together the distal end of the upper arm 206. That is, the retaining ring can help to maintain the coupling of the first and second body components 220A, 220B. In this specific implementation, the upper arm 206 has two retaining rings 240A, 240B as best shown in FIG. 6A. Alternatively, any upper arm embodiment disclosed or contemplated herein can have one, three, or any number of retaining rings to help hold the distal end of the upper arm together. Further, it is understood that any known mechanism or component for helping to maintain the coupling of the two body components 220A, 220B can be used. In a further embodiment, the upper arm 206 can also have an end-mounted retaining ring 242, as best shown in FIG. 6C. As with the retaining rings 240A, 240B, the end-mounted retaining ring 242 helps to hold the distal end of the upper arm 206 together.

In certain embodiments, the upper arm 206 can also have an anchor point 248 disposed on the second body component 220B as best shown in FIG. 6B. The anchor point 248 is configured to act as an anchor or attachment point for one or more elongate elastic components (also referred to herein as "elastic tendons" or "elastic bands") (not shown) that extend over the elbow joint 208 and couple to the forearm attached thereto (such as forearm 210) such that the elastic band (not shown) can apply a restraining force to the upper arm 206 and forearm (such as forearm 210) when the forearm is actuated to bend at the elbow joint 208. That is, the elastic band is intended to reduce any loose couplings or "sloppiness" of the various components at the joint 208, thereby enhancing the coupling of those components. Thus, as the forearm (such as forearm 210) is actuated to bend at the elbow joint 208, the elastic band is stretched, thereby resulting in force being applied at the elbow joint 208 that urges the forearm to return to the "straight" position as best shown in FIG. 5B. In the embodiment as shown, the anchor point 248 is a countersunk bolt 248 threadably coupled to the second body component 220B. Alternatively, instead of the bolt 248, any component or mechanism that can serve as an anchor point 248 can be incorporated into the arm 206.

In one embodiment, the third upper arm bevel gear 238 is configured to be coupleable to a matching bevel gear fixed to a forearm (such as forearm 210, for example) that is coupled to the upper arm 206. Hence, in one embodiment, the drivetrain in the upper arm 206 can be used to cause rotation of the forearm (such as forearm 210) in relation to the upper arm 206. The drivetrain is made up of the first upper arm bevel gear 228, the second upper arm bevel gear 230, the driveshaft 232, and the third upper arm bevel gear 238. In use, the first upper arm bevel gear 228 can be actuated to rotate (by rotation of the spur gear 136, according to some implementations), thereby causing the second upper arm bevel gear 230 to rotate, thereby causing the driveshaft 232 to rotate. Rotation of the driveshaft 232 causes the third upper arm bevel gear 238 to rotate, thereby causing any forearm component coupled thereto to rotate in relation to the upper arm 206. As a result, rotation of the bevel gear 238 causes the forearm (such as forearm 210) to move in relation to the upper arm 206 at the elbow joint (such as elbow joint 208).

According to one embodiment, the coupling of the upper arm 206 to the device 10 described above results in an arm with five degrees of freedom. That is, as discussed above with respect to FIGS. 4A and 4B, each shoulder (such as shoulders 14, 16 discussed above in relation to FIG. 1A) provides three degrees of freedom in the form of pitch, yaw, and rotation of the elbow. In this embodiment, the fourth degree of freedom is the rotation of the end effector around an axis parallel to the longitudinal axis of the forearm, and the fifth degree of freedom is the rotation of each of the graspers that cause the graspers to open and close. In this implementation, the third degree of freedom—the rotation of the output bevel gear 154 as discussed above—is utilized to actuate the elbow joint 208 instead of causing roll of the upper arm 206. Thus, in this particular embodiment, the upper arm 206 does not rotate around its own longitudinal axis.

Figure 7:
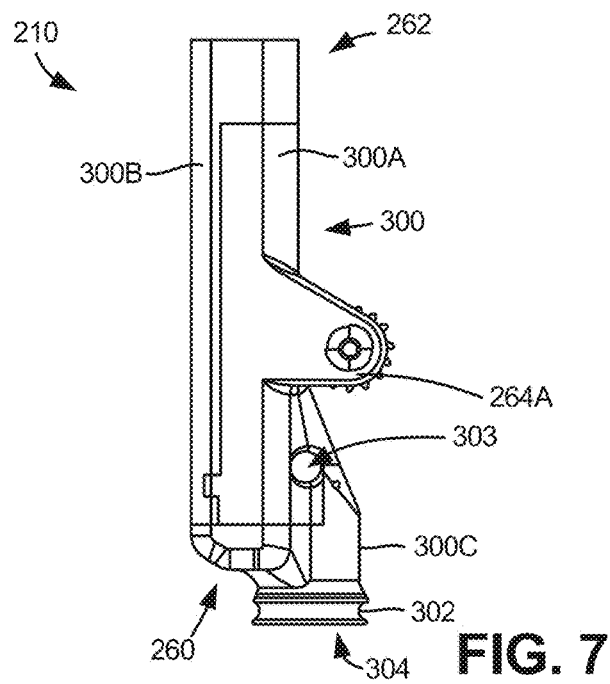
FIG. 7 is a side view of a forearm of a robotic device, according to one embodiment.
Figure 8A:
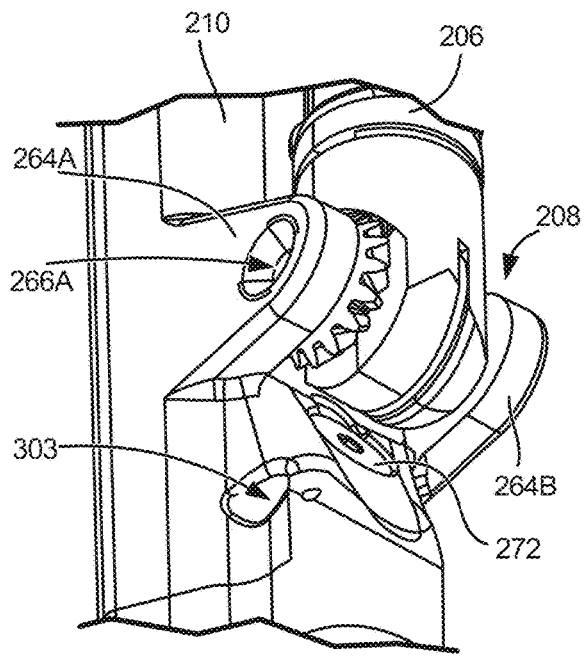
FIG. 8A is a perspective view of an elbow joint, according to one embodiment.
Figure 8B:
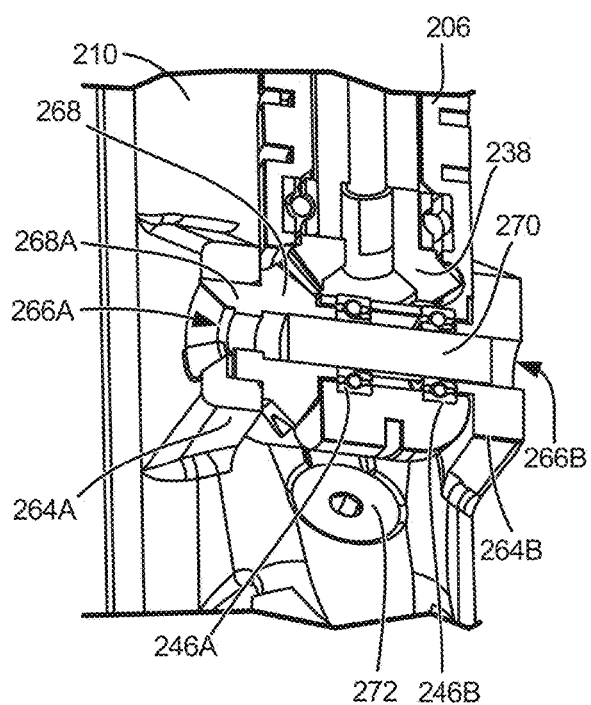
FIG. 8B is a cross-sectional view of the elbow joint of FIG. 8A, according to one embodiment.

FIGS. 7, 8A, and 8B depict the forearm 210 that is coupled with the upper arm 206, according to one embodiment. The forearm 210 has a forearm body 300 (also referred to as a "casing" or "shell") that contains and constrains the one or more motors (discussed below). The body 300 can have, in certain embodiments, a cautery connection (not shown) disposed in the body 300 and a cautery wire opening 303 defined therein. In one implementation as shown, the body 300 is made up of three components: a main body 300A, a electronics cover 300B, and a distal cover 300C. The electronics cover 300B contains a controller (not shown)—which can include a printed circuit board ("PCB")—that is coupled to the motors (discussed below) such that the controller can operate to control the motors. Further, the electronics cover 300B can sealably and fluidically protect the controller and any other electronics (not shown) contained within the body 300 from the external environment. The distal cover 300C is positioned at or on a distal end of the body 300 and has a lip 302 defined therein that is configured to receive and help to retain any elastic constraint that is used to couple and fluidically seal a sterile cover (not shown) to the forearm 210 such that the cover can be retained in its appropriate position during use. Alternatively, the distal cover 300C can have any known component or mechanism for receiving, retaining, or coupling to a sterile cover. Further, the distal cover 300C defines an opening 304 at its distal end that is configured to receive an interchangeable end effector, as discussed in further detail below.

The forearm 210 also has two protrusions 264A, 264B as best shown in FIGS. 8A and 8B that form a portion of the joint 208 at which the upper arm 206 is coupled to the forearm 210. In this implementation, the two protrusions 264A, 264B (and thus the elbow joint 208) are positioned at a point along the length of the forearm 210 between the distal end 260 and the proximal end 262 of the forearm 210. That is, the protrusions 264A, 264B are spaced from both the distal end 260 and proximal end 262 of the forearm 210. In this particular embodiment, the protrusions 264A, 264B (and thus the joint 208) are positioned at or substantially adjacent to a midpoint along the length of the forearm 210 as shown. Alternatively, the protrusions 264A, 264B (and thus the joint 208) are positioned anywhere along the length of the forearm 210 such that the protrusions 264A, 264B are spaced from both the proximal 262 and distal 260 ends. As such, rotation of the forearm 210 does not occur at the proximal end 262 of the forearm 210 but instead occurs at some other point along the length of the forearm 210 as determined by the position of the protrusions 264A, 264B.

Each protrusion 264A, 264B has an opening 266A, 266B, respectively, defined therein as shown. As best shown in FIG. 8B, a joint gear 268 is disposed within the joint 208 between the two protrusions 264A, 264B such that the shaft 268A of the gear 268 is rotatably disposed within the opening 264A. Further, a joint shaft 270 is also disposed within the joint 208 between the two protrusions 264A, 264B such that the shaft 270 is rotatably disposed within the opening 264B at one end and disposed within the gear 268 at the other end.

When the upper arm 206 is coupled to the forearm 210 as shown in FIG. 8B, the distal end of the upper arm 206 is disposed between the two protrusions 264A, 264B such that the opening 244 (as best shown above in FIGS. 6A, 6B, and 6D) is disposed between and axially aligned with the two openings 266A, 266B. The distal end of the upper arm 206 is coupled to the forearm 210 by the joint shaft 270, which is disposed through opening 264B, opening 244 (and supported by bearings 246A, 246B in opening 244 as discussed above), and into the gear 268 such that the distal end of the upper arm 206 is rotatably retained in the joint 210 between the two protrusions 264A, 266B as shown.

The joint gear 268 is rotationally coupled to the third upper arm bevel gear 238 of the upper arm 206 as shown in FIG. 8B such that rotation of the third upper arm bevel gear 238 causes rotation of the joint gear 268.

While the joint 208 in this specific implementation is made up of the two protrusions 264A, 264B, the joint shaft 270, and the joint bevel gear 268, it is understood that any known joint or rotational coupling configuration or mechanism can be incorporated into these various arm embodiments.

In certain embodiments, the forearm 210 can also have an anchor point 272 as best shown in FIGS. 8A and 8B. Like the anchor point 248 discussed above, the anchor point 272 is configured to act as the other anchor or attachment point (in combination with the anchor point 248) for any elastic tendons (not shown) as discussed above that extend over the elbow joint 208. In the embodiment as shown, the anchor point 272 is a countersunk bolt 272 threadably coupled to the forearm 210. Alternatively, instead of the bolt 272, any component or mechanism that can serve as an anchor point 272 can be incorporated into the forearm 210.

One exemplary interchangeable end effector 320 that can be coupled to the forearm 210 discussed above is depicted in FIGS. 9A-9C. Alternatively, it is understood that the end effector 320 can be coupled with any known robotic arm or robotic surgical device. It is further understood that any interchangeable end effector can be coupled to the forearm 210 or removed and replaced with any other known interchangeable end effector.

The end effector 320 in this exemplary embodiment is a graspers end effector 320 with a graspers component 322 having first and second grasper arms 322A, 322B. The end effector 320 has a twistable knob 324 that can be grasped by a user to couple the end effector 320 to and uncouple the end effector 320 from an arm (such as the forearm 210). The knob 324 is coupled to the locking collar 326 having locking protrusions 326A that mateably couple to the four notches 382 defined in the cover 300C as described in further detail below. Rotation of the knob 324 causes rotation of the locking collar 326, thereby allowing for positioning the protrusions 326A into the notches 382 and thereby coupling the end effector 320 to the forearm 210. In certain embodiments, a sealing ring (also referred to herein as an "o-ring") 328 is disposed around the end effector 320 at a proximal end or portion of the knob 324 such that the ring 328 can provide for a fluidically sealed coupling of the end effector 320 to the forearm 210 when the end effector 320 is coupled thereto as described above. Further, according to some implementations, the ring 328 can also provide outward pressure or force against both the end effector 320 and the forearm 210 such that counter-rotation of the knob 324 that might cause the end effector 320 to uncouple during use is reduced or eliminated.

The end effector 320 has both a rotational drive system and a grasper arm actuation drive system. The rotational drive system is made up of a rotatable yoke 330 that is coupled to the graspers 322 such that rotation of the yoke 330 causes rotation of the graspers 322. That is, the yoke 330 has two flanges 330A, 330B as best shown in FIG. 9A such that the graspers 322 are disposed between the two flanges 330A, 330B and coupled thereto via the pin 331. At its proximal end, the yoke 330 has mateable coupling components 332 that are configured to couple to the rotational drive component 370 in the distal end of the forearm 210, as described in further detail below. More specifically, in this exemplary embodiment, the mateable coupling components 332 are two protrusions 332 as best shown in FIGS. 9A and 9C. The rotatable yoke 330 is axially restrained (such that the yoke 330 does not move distally or proximally in relation to the length of the end effector 320) by a groove 334 defined around an outer surface of the yoke 330 such that a pin (not shown) can be inserted through an opening 336 in the knob 324 (as best shown in FIG. 9A) and positioned in the groove 334, thereby allowing the yoke 330 to rotate but preventing it from moving in an axial direction. Thus, rotation of the rotational drive component 370 in the forearm causes rotation of the rotatable yoke 330, which causes rotation of the graspers 322.

The grasper arm actuation drive system is made up of an internally-threaded rotatable cylinder 338, an externally threaded drive pin 340 threadably coupled to the cylinder 338, and two linkages (including linkage 342) coupled to the pin 340. The rotatable cylinder 338 has mateable coupling components 344 at its proximal end that are configured to couple to the actuation drive component 372 in the distal end of the forearm 210, as described in further detail below. More specifically, in this exemplary embodiment, the mateable coupling components 344 are two protrusions 344 as best shown in FIGS. 9A and 9C. The rotatable cylinder 338 is axially restrained by a groove 346 defined around an outer surface of the cylinder 338 such that a pin (not shown) can be inserted through an opening (not shown) in the knob 324 (similar to opening 336 discussed above) and positioned in the groove 346, thereby allowing the cylinder 338 to rotate but preventing it from moving in an axial direction.

The rotatable cylinder 338 has a lumen 347 with a lumen inner surface 348 that is threaded. The drive pin 340 has a distal head (also referred to as a "coupling component") 350 and an externally-threaded proximal body 352 that is sized to be disposed within the lumen 347 of the cylinder 338 such that the proximal body 352 is threadably coupled to the lumen inner surface 348. The distal head 350 has two openings 354A, 354B defined therein that are coupleable to the two linkages. More specifically, the linkage 342 is coupled to the distal head 350 at opening 354A with a pin or similar coupling component (not shown). Further, a second linkage (not shown) is coupled to the distal head 350 at opening 354B in the same fashion. The linkages (342 and the linkage that is not shown) are coupled to the proximal ends of the grasper arms 322A, 322B. As such, rotation of the actuation drive component 372 in the forearm 210 causes rotation of the rotatable cylinder 338, which causes axial movement of the drive pin 340 (through the threadable coupling of the cylinder 338 and the pin 34), which causes movement of the linkages (342 and the linkage that is not shown), which causes the grasper arms 322A, 322B to rotate around the axis at pin 331 in the yoke 330 such that the arms 322A, 322B move between an open position and a closed position.

Figure 10A:
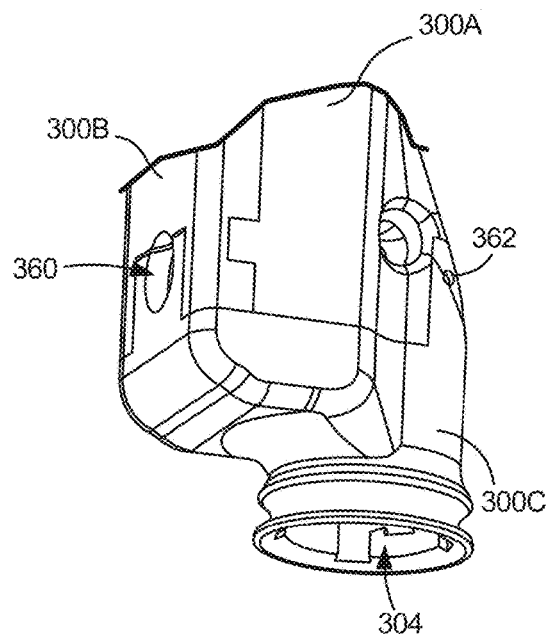
FIG. 10A is a perspective view of a distal portion of the forearm of FIG. 7, according to one embodiment.
Figure 10B:
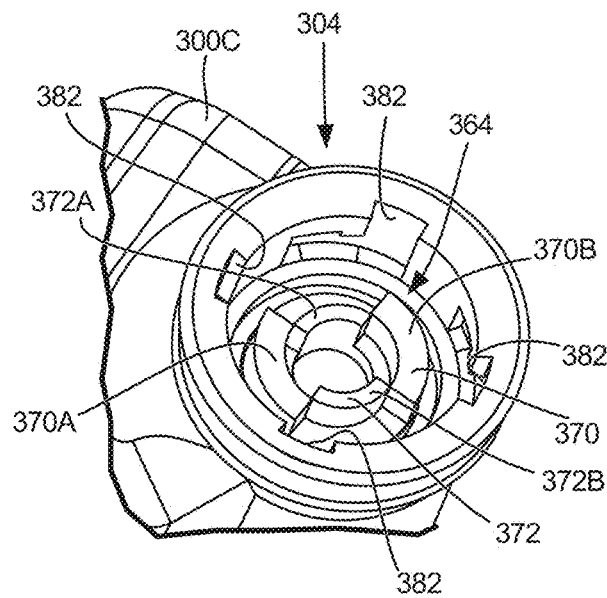
FIG. 10B is a different perspective view of a distal portion of the forearm of FIG. 10A, according to one embodiment.
Figure 10C:
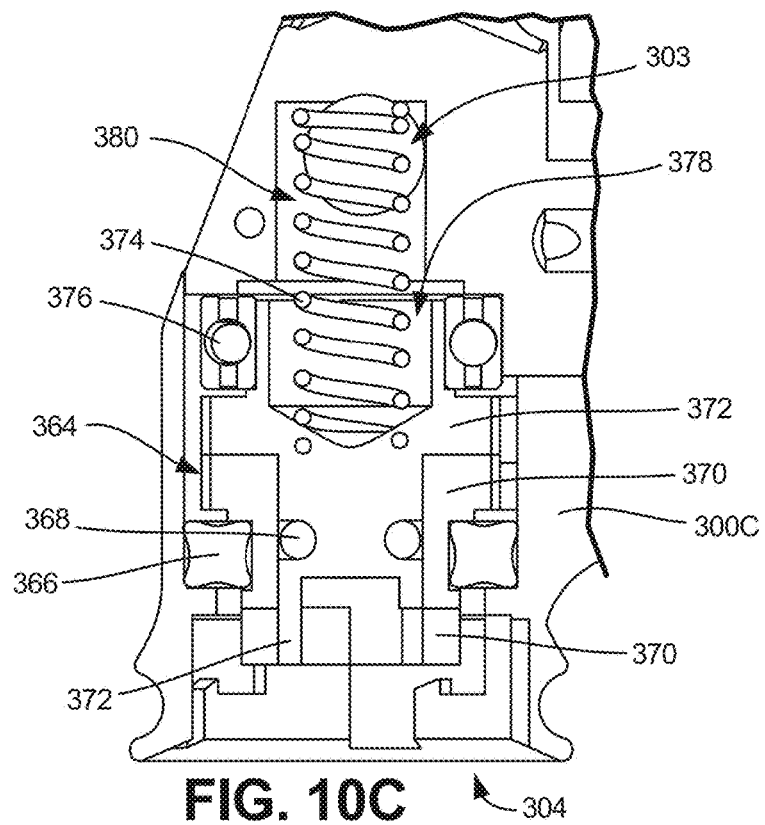
FIG. 10O is a cross-sectional side view of the distal portion of the forearm of FIG. 10A, according to one embodiment.

FIGS. 10A-10C depict the distal cover 300C of the body 300, along with the end effector interface 364, according to one embodiment.

As best shown in FIG. 10A, according to one implementation, the distal cover 300C discussed above can be coupled to the main body 300A and electronics cover 300B by a fastener 360 positioned through the distal cover 300C and the electronics cover 300B, thereby coupling both the distal cover 300C and electronics cover 300B to the main body 300A. In one embodiment, the fastener 360 is a bolt 360. Alternatively, any known fastener or attachment mechanism can be used.

According to another embodiment, a further fastener 362 is provided to further couple the distal cover 300C to the main body 300A. The fastener 362 is a pin 362. Alternatively, the fastener 362 can be any known fastener or attachment mechanism.

As best shown in FIGS. 10B and 10C, the distal cover 300C, in accordance with certain implementations, houses the end effector interface 364. The end effector interface 364 is configured to couple to the actuation components of an end effector (such as end effector 320 discussed above). More specifically, in those exemplary embodiments in which the end effector interface 364 is coupling to the end effector 320, the interface 364 is configured to couple to both the rotational drive system and the graspers drive system as discussed above. The interface 364 has first and second sealing rings 366, 368, a rotatable rotational drive component 370, a rotatable graspers actuation drive component 372, and an electrical contact spring 374.

It is understood that this interface 364 can be coupled with various end effectors. While the description below will specifically reference the end effector 320 and how the components of the interface 364 relate to and couple with that end effector 320, that is not intended to limit the use of this end effector interface 364 to solely the end effector 320. Instead, the interface 364 can be coupled to any end effector having the appropriate components to couple thereto.

The rotatable rotational drive component 370, in this specific implementation, is a rotatable drive cylinder 370 with mateable coupling components 370A, 370B (as best shown in FIG. 10B) that are configured to mate with the mateable coupling components 332 of the rotatable yoke 330 in the end effector 320, as discussed above. More specifically, the mateable coupling components 370A, 370B in this embodiment are projections 370A, 370B that are mateable or coupleable with the mateable coupling components 332 of the rotatable yoke 330 in the end effector 320.

The rotatable graspers actuation drive component 372, in this specific implementation, is a rotatable drive cylinder 372 with mateable coupling components 372A, 372B (as best shown in FIG. 10B) that are configured to mate with the mateable coupling components 344 of the rotatable cylinder 338 in the end effector 320, as discussed above. More specifically, the mateable coupling components 372A, 372B in this embodiment are projections 372A, 372B that are mateable or coupleable with the mateable coupling components 344 of the rotatable cylinder 338 in the end effector 320.

In one implementation, the rotatable graspers actuation drive component 372 can transfer electrical energy to the graspers of an end effector (such as the graspers 322 of end effector 320) for cauterization. That is, the rotatable cylinder 372 has a proximal lumen 378 defined in a proximal end of the cylinder 372 that is configured to receive the electrical contact spring 374. The spring 374 extends proximally into a lumen 380 defined in the body 300 such that the spring 374 is positioned adjacent to the cautery wire opening 303 discussed above such that a cautery wire (or cautery cable) positioned through the opening 303 can be coupled to the spring 374. Alternatively, the spring 374 can be any electrical contact component. It is understood that, according to certain embodiments, the cautery wire opening 303 is defined on both sides of the body 300 so that the same body 300 configuration can be used in both the left and right arms of the device.

The rotatable drive cylinder 372 is positioned or nested within the rotatable drive cylinder 370 as shown. The first sealing ring 366 is an o-ring 366 that is disposed between the distal cover 300C and the rotatable drive cylinder 370. The second sealing ring 368 is an o-ring 368 that is disposed between the rotatable drive cylinder 370 and the rotatable drive cylinder 372. The two rotatable drive cylinders 370, 372 are supported and rotatably retained in place by a first bearing 376, along with the first sealing ring 366.

As best shown in FIG. 10B, the distal cover 300C, according to a further embodiment, has at least two notches defined in the distal cover opening 304 that can be mateable or coupleable with the locking protrusions 326A on the end effector 320 as discussed above. In this specific implementation, the cover 300C has four notches 382 that are mateable with the four protrusions 326A discussed above such that the end effector 320 can be coupled to the distal cover 300C with a single rotation or "twist" of the know 324 of the end effector 320. Alternatively, any known locking mechanism or feature can be used.

Figure 11A:
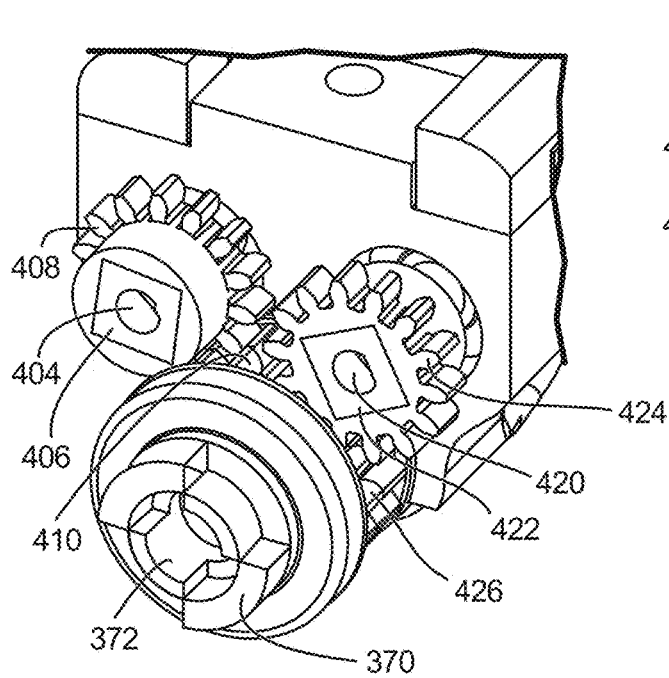
FIG. 11A is a perspective view of certain internal components of the distal portion of the forearm of FIG. 10, including certain motors and gears therein, according to one embodiment.
Figure 11B:
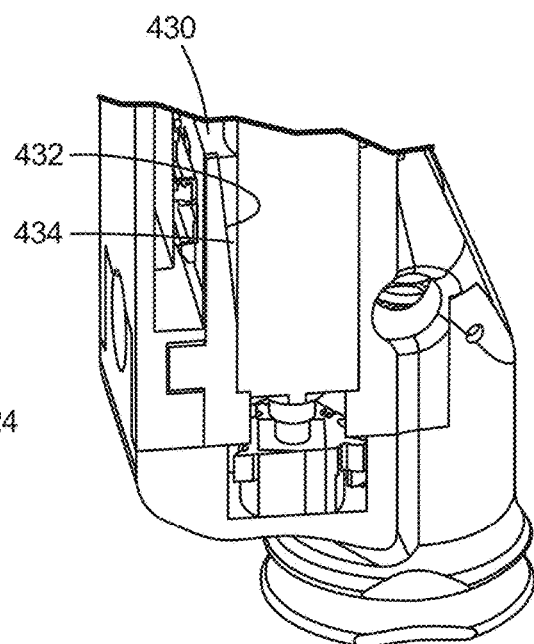
FIG. 11B is a perspective cross-sectional view of certain internal components of the distal portion of the forearm of FIG. 10, according to one embodiment.
Figure 11C:
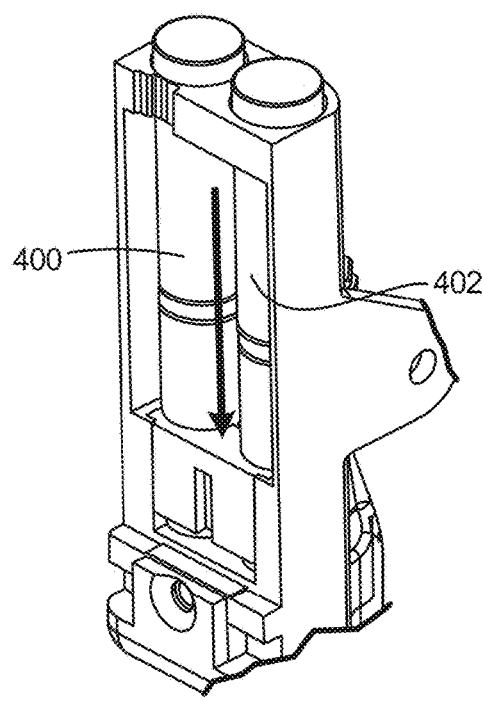
FIG. 11C is a perspective view of certain internal components of the distal portion of the forearm of FIG. 10, including certain motors therein, according to one embodiment.

According to one embodiment, FIGS. 11A-11C depict the motors within the body 300 that power the rotatable rotational drive component 370 and the rotatable graspers actuation drive component 372 discussed above. More specifically, in accordance with one implementation, the forearm 210 has two motors 400, 402 disposed therein, as best shown in FIG. 11C. In one embodiment, the motors 400, 402 are 6 mm brushless motors. Alternatively, the motors 400, 402 can be any known type of motors for use in robotic arms.

As best shown in FIG. 11A, the motor 400 is coupled to a shaft 404, which is coupled to a bushing 406, which in turn is coupled to the drive gear (also referred to as a "spur gear") 408. Alternatively, the shaft 404 can be coupled directly to the drive gear 408. The drive gear 408 is rotatably coupled to gear teeth 410 that are attached to or otherwise coupled to the rotatable graspers actuation drive component 372. Thus, actuation of the motor 400 causes rotation of shaft 404, which causes rotation of drive gear 408, which causes rotation of the rotatable graspers actuation drive component 372, which ultimately causes the grasper arms 322A, 322B to move between an open position and a closed position, as described above.

As also shown in FIG. 11A, the motor 402 is coupled to a shaft 420, which is coupled to a bushing 422, which in turn is coupled to the drive gear (also referred to as a "spur gear") 424. Alternatively, the shaft 420 can be coupled directly to the drive gear 424. The drive gear 424 is rotatably coupled to gear teeth 426 that are attached to or otherwise coupled to the rotatable rotational drive component 370. Thus, actuation of the motor 402 causes rotation of shaft 420, which causes rotation of drive gear 424, which causes rotation of the rotatable rotational drive component 370, which ultimately causes the graspers end effector to rotate, as described above.

According to one implementation, the motors 400, 402 are retained or held in place in the forearm 210 by a locking wedge 430. In use according to one embodiment, the locking wedge 430 can be urged toward the distal end of the forearm 210 along the two motors 400, 402 such that the angled or wedge portion 434 is positioned in the wedge-shaped opening 432 defined in the body 300 to help to retain or "lock" the two motors 400, 402 in place. This positioning of the wedge portion 434 in the wedge-shaped opening 432 urges the wedge portion 434 against the motors 400, 402, thereby creating a friction-based contact between the wedge portion 434 and motors 400, 402, thereby helping to retain the motors 400, 402 in place via the frictional force. According to one embodiment, the locking wedge 430 can be positioned manually to lock the motors 400, 402 in position.

Figure 12A:
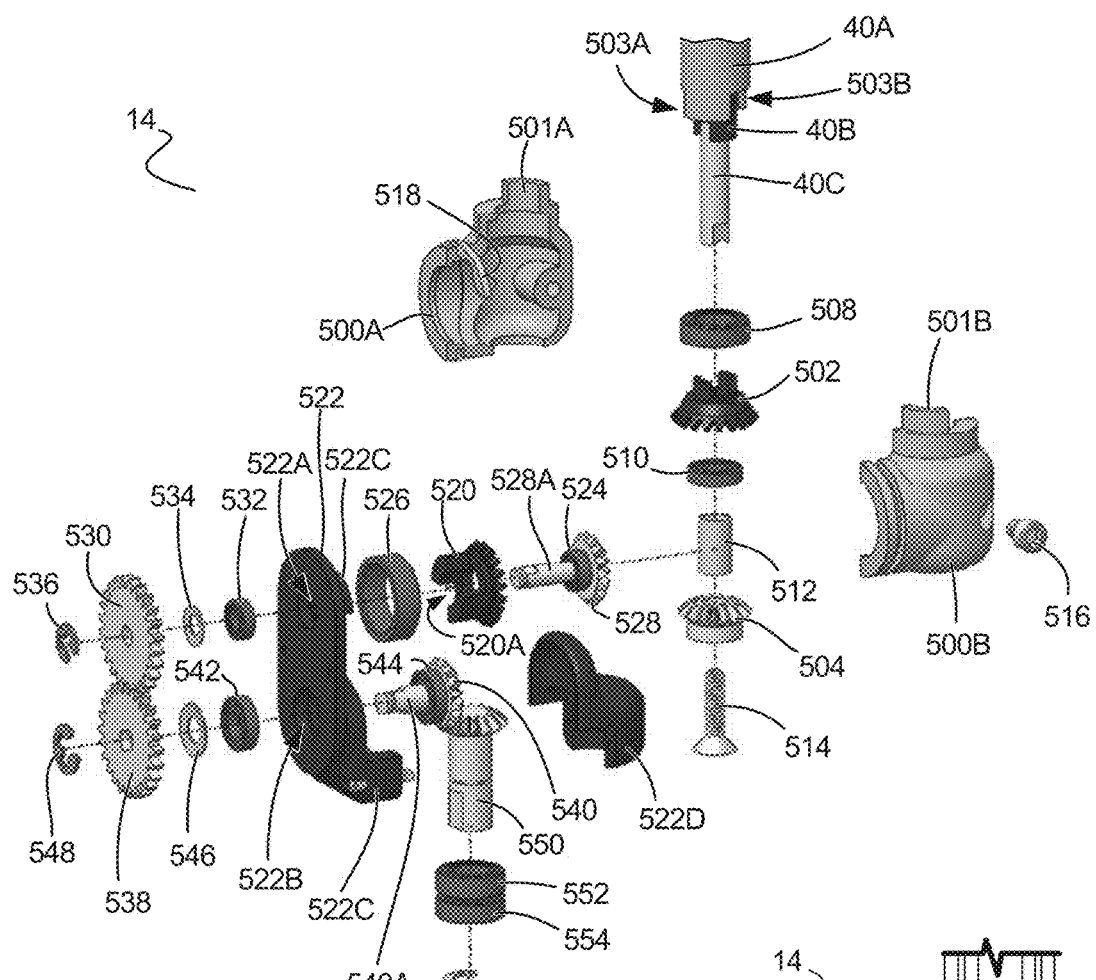
FIG. 12A is a perspective view of various components of another embodiment of a right shoulder joint, according to one embodiment.
Figure 12B:
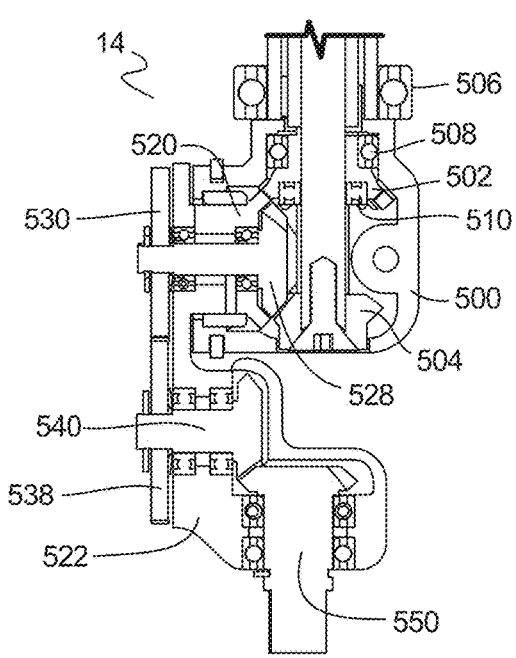
FIG. 12B is a cross-sectional side view of various components of the right shoulder joint of FIG. 12A, according to one embodiment.

FIGS. 12A and 12B depict another embodiment of the right shoulder joint 14 and its various components. More specifically, FIG. 12A depicts an exploded view of the internal components of the right shoulder joint 14, while FIG. 12B depicts a cross-sectional front view of the internal components of the right shoulder joint 14. As shown in both FIGS. 12A and 12B, and as will be explained in further detail below, the outer driveshaft 40A (discussed above in relation to FIGS. 2-3E) is coupled (or rotationally constrained) to the shoulder roll housing (also referred to herein as the "shoulder housing" or "conversion body") 500, while the middle driveshaft 40B (discussed above in relation to FIGS. 2-3E) is coupled to the upper drive bevel gear 502, and the inner driveshaft 40C (discussed above in relation to FIGS. 2-3E) extends through the spacer 512 and is coupled to the lower drive bevel gear 504.

While the remainder of this description will focus on the right shoulder joint 14 and its components, it is understood that the components of the left shoulder joint 16, the components coupled thereto, the relationship of those components to each other, and their functionality can be substantially similar to the right shoulder joint 14.

As best shown in FIG. 12B, the outer driveshaft 40A and shoulder housing 500 are supported by the first bearing 506, which is disposed on an outer portion of the housing 500. In addition, as best shown in both FIGS. 12A and 12B, the outer driveshaft 40A and shoulder housing 500 are further supported by the second bearing 508, which is disposed within the housing 500. The middle driveshaft 40B and the upper drive bevel gear 502 are supported by the second bearing 508 and the third bearing 510, which is positioned within the distal end of the upper drive bevel gear 502 as best shown in FIG. 12B. The bearings 506, 508, 510 are preloaded using a single countersunk screw 514 threaded into the distal end of the inner driveshaft 40C. Alternatively, any attachment components can be used to preload the bearings 506, 508, 510.

According to one embodiment, as best shown in FIG. 12A, the shoulder housing 500 is made up of two housing components: the first housing component (or "first housing shell") 500A and the second housing component (or "second housing shell") 500B. In this implementation, the two shells 500A, 500B are coupled together with a screw 516 and a retaining ring 518. Alternatively, any known attachment components or mechanisms can be used to couple the two shells 500A, 500B together. In a further alternative, the housing 500 is single unitary housing.

As mentioned above, the outer driveshaft 40A is coupled (or rotationally constrained) to the shoulder roll housing 500. More specifically, projections 501A, 501B extending from a top portion of the housing 500 (more specifically, from each of the two housing shells 500A, 500B, according to this embodiment) are mateable with two notches 503A, 503B in the outer driveshaft 40A. Alternatively, any mechanism(s) or feature(s) for coupling the driveshaft 40A and the housing 500 can be used. Thus, rotation of the outer driveshaft 40A causes the shoulder housing 500 to rotate around the longitudinal axis of the driveshaft 40A, thereby causing any arm coupled to the shoulder (at output bevel gear 550 discussed below) to rotate around the same axis, resulting in the arm moving from left to right ("yaw") in relation to the device body (such as body 12 discussed above).

The upper drive bevel gear 502 is mateably coupled to the first driven bevel gear 520 such that rotation of the upper drive bevel gear 502 causes rotation of the first driven bevel gear 520 around the longitudinal axis of the shaft 528A of the second driven bevel gear 528 discussed below. The first driven bevel gear 520 drives the pitch of the shoulder 14 by causing rotation of the bevel gear body 522 around the same longitudinal axis of the shaft 528A, thereby causing the arm to move "up and down" in relation to the device body. That is, at its distal end, the first driven bevel gear 520 is coupled to the bevel gear body (also referred to as "rotatable arm," "rotatable body," "rotation arm," "rotation body," "pitch arm," or "pitch body") 522 such that rotation of the first driven bevel gear 520 causes rotation of the bevel gear body 522. More specifically, the bevel gear body 522 has two openings 522A, 522B defined therein (as best shown in FIG. 12A), with a mateable coupling 522C disposed around one side of the opening 522A that is coupled to the first driven bevel gear 520 such that rotation of the bevel gear 520 causes rotation of the bevel gear body 522. In this exemplary embodiment, the first driven bevel gear 520 has an opening 520A defined therethrough such that the bevel gear 520 is rotatably disposed over the second driven bevel gear 528, which is discussed in further detail below. The first driven bevel gear 520 is constrained by fourth bearing 524 and fifth bearing 526.

It is understood that the rotation body 522 can be any component that has two openings as described herein and can be coupled to the various components as described.

The lower drive bevel gear 504 is mateably coupled to the second driven bevel gear 528 such that rotation of the lower drive bevel gear 504 causes rotation of the second driven bevel gear 528. As mentioned above, the second driven bevel gear 528 is rotatably disposed through the opening 520A in the first driven bevel gear 520 such that the second driven bevel gear 528 is at least partially disposed within the first driven bevel gear 520. The second driven bevel gear 528 is coupled to the first spur gear 530 such that rotation of the second driven bevel gear 528 causes rotation of the first spur gear 530. That is, the shaft 528A of the second driven bevel gear 528 extends through the opening 522A in the bevel gear body 522 and is coupled to the first spur gear 530. In one specific embodiment, the second driven bevel gear 528 is mateably coupled to the first spur gear 530 via a geometric coupling. The second driven bevel gear 528 is constrained by the fourth bearing 524 and a sixth bearing 532. It is understood that the bearings 524, 526, 532 are preloaded using a spring 534 and translationally constrained by a retaining ring 536. In one embodiment, the spring 534 is a Belleville spring 534.

The first spur gear 530 discussed above is mateably coupled to the second spur gear 538 such that rotation of the first spur gear 530 causes rotation of the second spur gear 538. The second spur gear 538 is coupled to the third driven bevel gear 540 such that rotation of the second spur gear 538 causes rotation of the third driven bevel gear 540. That is, the shaft 540A of the third driven bevel gear 540 extends through the opening 522B in the bevel gear body 522 and is coupled to the second spur gear 538. In one specific embodiment, the second spur gear 538 is mateably coupled to the shaft 540A of the third driven bevel gear 540 via a geometric coupling. The third driven bevel gear 540 is constrained by a seventh bearing 542 and an eighth bearing 544. According to one implementation, both bearings 542, 544 are disposed within or press fit within the bevel gear body 522. It is understood that the bearings 542, 544 are preloaded using a spring 546 and translationally constrained by a retaining ring 548. In one embodiment, the spring 546 is a Belleville spring 546.

The third driven bevel gear 540 is mateably coupled to a fourth driven bevel gear (also referred to herein as a "yaw output gear" or "output gear") 550 such that rotation of the third driven bevel gear 540 causes rotation of the output gear 550. The output gear 550 is constrained by a ninth bearing 552 and a tenth bearing 554. In accordance with one embodiment, the bearings 552, 554 are retained in place by the bevel gear body 522. Further, the gear 550 is translationally constrained by a retaining ring 556.

In this embodiment as shown in FIGS. 12A and 12B, the pitch, yaw, and roll rotations are coupled. That is, the actuation of one of the rotations will cause actuation of at least one of the other rotations as a result of their coupled nature such that some counteraction must occur if the secondary actuation is undesirable. For example, when it is desirable to cause the device arm coupled to the shoulder to move "up and down" (pitch), the bevel gear 502 is actuated to rotate, thereby causing gear 520 to rotate as described above. However, that is not the only motion that is caused by the actuation of bevel gear 502. That is, the coupled nature of these drive components results in the output gear 550 rotating as well. If that secondary rotation is undesirable, it must be nullified by a counteracting actuation of bevel gear 504 to prevent the rotation of output gear 550. Similarly, actuation of the drive components to cause yaw (rotation of the shoulder housing 500 around the longitudinal axis of the driveshaft 40A) can also cause some pitch and roll. Thus, the coupled nature of these three rotations requires a counteracting actuation if the secondary actuations are undesirable.

In accordance with one implementation, the bevel gear body 522 is made up of two components 522C, 522D coupled together as best shown in FIG. 12A. Alternatively, the bevel gear body 522 can be a single, unitary component 522.

Further embodiments as best shown in FIGS. 13-17D relate to joint implementations that can be incorporated into shoulder joints, elbow joints, wrist joints, or other joints of a robotic arm. These joint embodiments have four degrees of freedom while—in some instances—requiring only three motors. In certain implementations, the joint embodiments below can be incorporated into a wrist joint, thereby resulting in a wrist joint with four degrees of freedom, which is two more degrees of freedom than known robotic grasper drivetrains. Hence, the wrist joint embodiments are nimble wrist joints providing more dexterity to the surgeon in comparison to known wrist joints. In other implementations, the joint embodiments below can be incorporated into a shoulder joint, thereby allowing for four degrees of freedom to pass through the shoulder joint and into the robotic arm coupled thereto. As a result of this embodiment, larger motors can be used to actuate the joints of the robotic arm coupled thereto and also allow for the lengths of the arm components to be determined based on factors other than solely motor size.

As mentioned above, these embodiments can utilize only three motors to control four degrees of freedom. As will be described in detail below, these configurations that have only three motors are possible because all three motors are coupled together in a shared state in which a fourth degree of freedom is realized. As detailed below, the coupling of the three motors can be accomplished in several ways, including by providing a braking force condition on one of the outputs such that only deliberate commands will cause a robotic joint to actuate.

It is understood that there are at least two embodiments described below having four degrees of freedom. The first embodiment, as depicted in FIGS. 13-14B, utilizes four motors, while the second embodiment, as depicted in FIGS. 15A-17D, requires only three motors.

Figure 13:
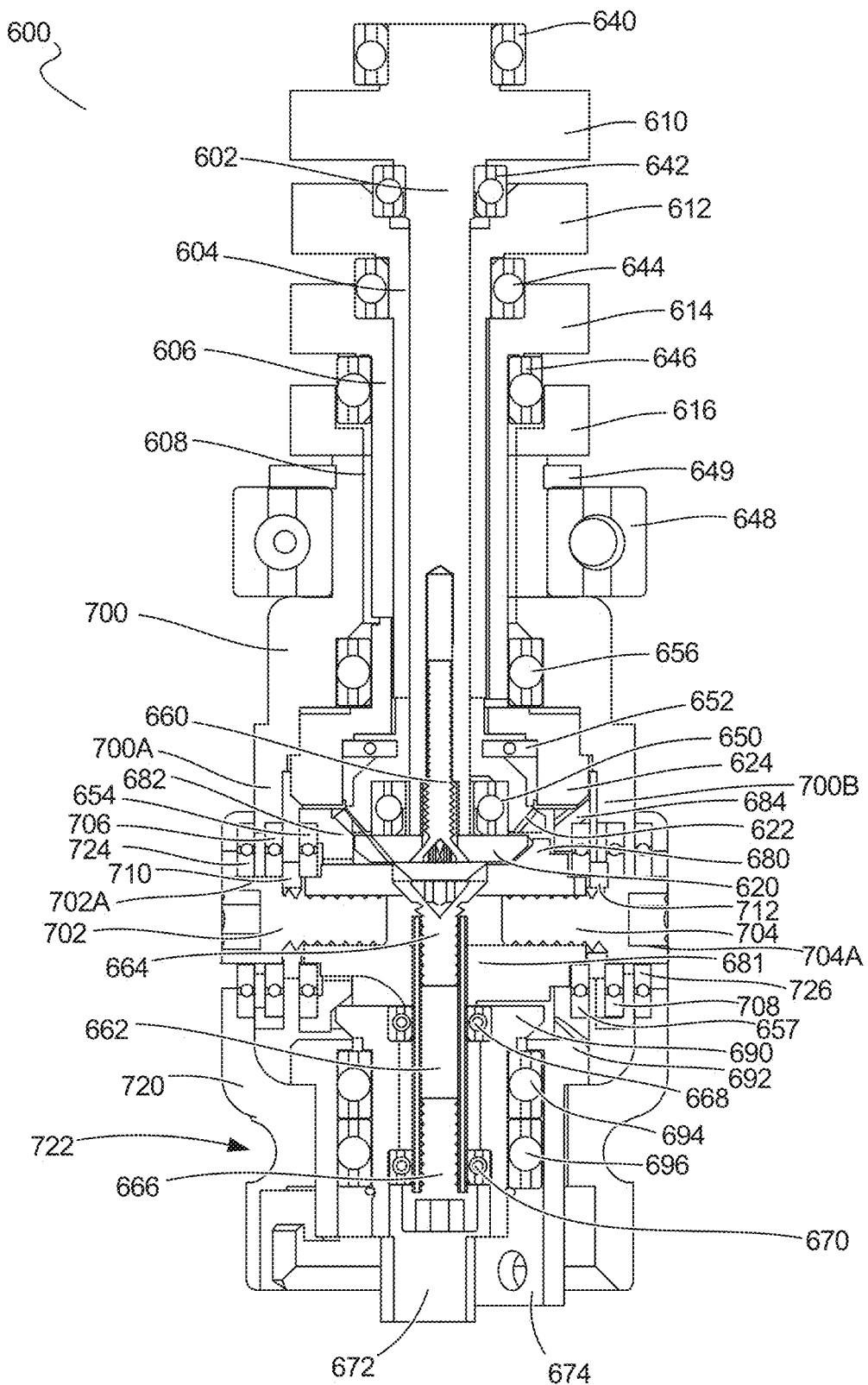
FIG. 13 is a cross-sectional side view of a joint for a robotic device, according to a further embodiment.

FIG. 13 depicts a cross-sectional front view of a joint 600 having a set of nested driveshafts 602, 604, 606, 608. More specifically, the set of four nested driveshafts 602, 604, 606, 608 includes a first (also referred to herein as "inner") driveshaft 602, a second (also referred to as "first middle") driveshaft 604, a third (also referred to as "second middle") driveshaft 606, and a fourth (also referred to as "outer") driveshaft 608. It is understood that the specific length of these driveshafts 602, 604, 606, 608 as shown in FIG. 13 is merely exemplary, and that the length can vary depending on various circumstances, including whether the joint 600 is a shoulder joint, elbow joint, wrist joint, or some other kind of joint.

Figure 14A:
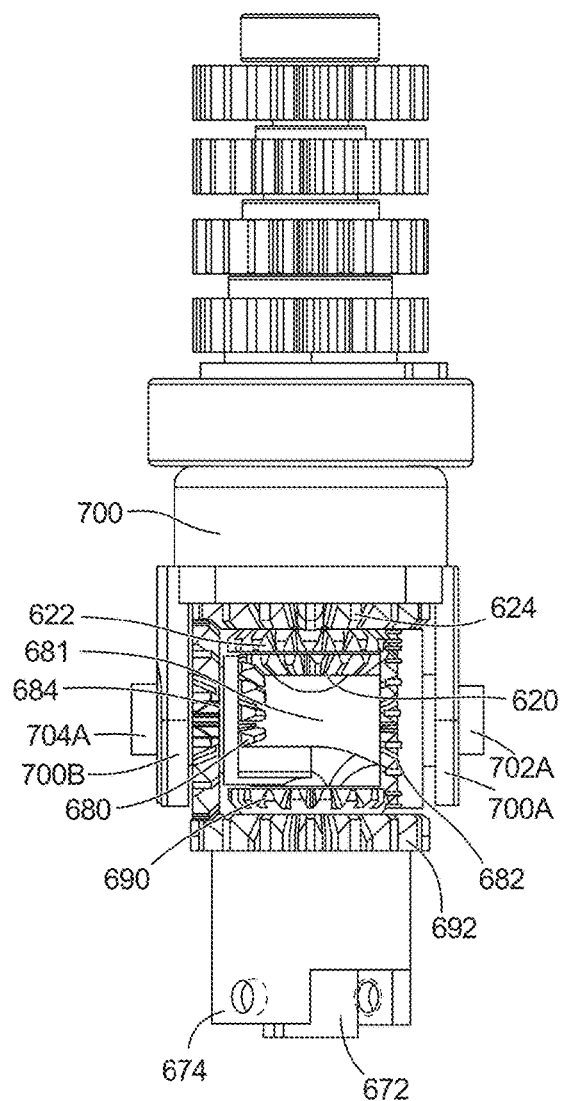
FIG. 14A is a side view of various components of the joint of FIG. 13, according to one embodiment.

The first driveshaft 602 is rotatably disposed within the second driveshaft 604 as shown, and has a first driven gear 610 fixedly or integrally attached at its proximal end as shown. The first driveshaft 602 is supported at its proximal end by first proximal bearing 640 and second proximal bearing 642, with the first bearing 640 being supported by the enclosure (not shown) of the joint 600 and the second bearing 642 being supported by the second driven gear 612. At its distal end, the first driveshaft 602 is rotationally coupled to a first bevel gear 620, as best shown in FIGS. 13, 14A, and 14B. According to one embodiment, the driveshaft 602 is coupled to the gear 620 via a geometric coupling, and the gear 620 is retained axially in relation to the driveshaft 602 by bolt 660. The driveshaft 602 and gear 620 are radially constrained in a first distal bearing 650.

Figure 14B:
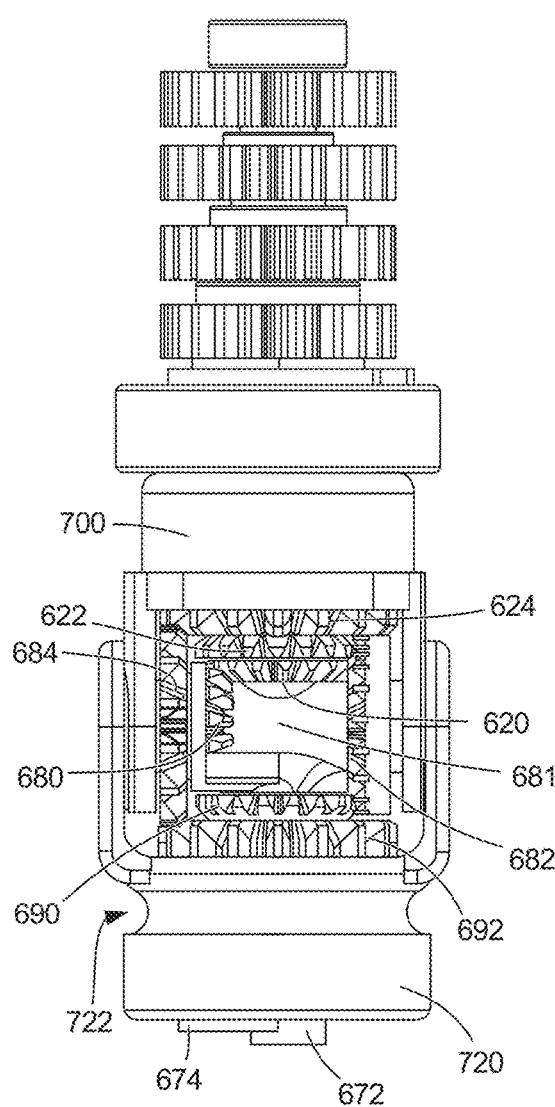
FIG. 14B is a side view of various components of the joint of FIG. 13, according to one embodiment.

The first bevel gear 620 is rotatably coupled to a first intermediate bevel gear 680, as best shown in FIGS. 13, 14A, and 14B. The bevel gear 680 is fixedly coupled or integral with a rotatable cylinder 681, which is fixedly coupled to a drive post 662, which extends distally toward a distal end of the joint 600 from the rotatable cylinder 681. The drive post 662 is retained in position by a first post bolt 664 and a second post bolt 666 and constrained by first post bearing 668 and second post bearing 670. Rotation of the first intermediate bevel gear 680 causes rotation of the cylinder 681 around the axis of the bevel gear 680, which causes the drive post 662 to rotate around the axis of the bevel gear 680, which is perpendicular to the rotational axis of the driveshafts 602, 604, 606, 608. As a result, the portion of the joint 600 distal to the rotatable cylinder 681 rotates with the drive post 662. Thus, actuation of the motor (not shown) coupled to the first driven gear 610 causes rotation of the first driven gear 610, which causes rotation of the first driveshaft 602. Rotation of the first driveshaft 602 causes rotation of the first bevel gear 620, which causes rotation of the first intermediate bevel gear 680 around an axis perpendicular to the axis of rotation of the driveshafts 602, 604, 606, 608. And rotation of the first intermediate bevel gear 680 causes rotation of the rotatable cylinder 681, which causes rotation of the drive post 662, which causes rotation of the portion of the joint 600 distal to the first intermediate bevel gear 680 around the same axis of rotation as the first intermediate bevel gear 680.

The second driveshaft 604 is rotatably disposed within the third driveshaft 606 as shown, and has a second driven gear 612 fixedly or integrally attached at its proximal end. The second driveshaft 604 is supported at its proximal end by second proximal bearing 642 and third proximal bearing 644, with the second bearing 642 being supported by the second driven gear 612 and the third bearing 644 being supported by the third driven gear 614. At its distal end, the second driveshaft 604 is rotationally coupled to a second bevel gear 622, as best shown in FIGS. 13, 14A, and 14B. According to one embodiment, the driveshaft 604 is coupled to the gear 622 via a geometric coupling, and the driveshaft 604 and gear 622 are constrained by a second distal bearing 652.

The second bevel gear 622 is rotatably coupled to a second intermediate bevel gear 682, as best shown in FIGS. 13, 14A, and 14B. Further, the bevel gear 682 is rotatably coupled to a first output bevel gear 690, which is rotationally coupled with or integral with the first (or "inner") rotatable output member 672. The second intermediate bevel gear 682 is supported by a third distal bearing 654, which is supported by a portion of the first intermediate bevel gear 680. Thus, actuation of the motor (not shown) coupled to the second driven gear 612 causes rotation of the second driven gear 612, which causes rotation of the second driveshaft 604. Rotation of the second driveshaft 604 causes rotation of the second bevel gear 622, which causes rotation of the second intermediate bevel gear 682 around an axis perpendicular to the axis of rotation of the driveshafts 602, 604, 606, 608. And rotation of the second intermediate bevel gear 682 causes rotation of the first output bevel gear 690 around an axis parallel to the axis of rotation of the driveshafts 602, 604, 606, 608, which causes rotation of the first rotatable output member 672 around the same axis of rotation. It is understood that the first rotatable output member 672 is configured to be coupled to an actuatable component, such as a portion of a robotic arm wrist, an end effector, or a robotic upper arm, depending on the location of the joint 600 on the robotic device.

The third driveshaft 606 is rotatably disposed within the fourth driveshaft 608 as shown and has a third driven gear 614 fixedly or integrally attached at its proximal end. The third driveshaft 606 is supported at its proximal end by third proximal bearing 644 and fourth proximal bearing 646, with the third bearing 644 being supported by the third driven gear 614 and the fourth bearing 646 being supported by the fourth driven gear 616. At its distal end, the third driveshaft 606 is rotationally coupled to a third bevel gear 624, as best shown in FIGS. 13, 14A, and 14B. According to one embodiment, the driveshaft 606 is coupled to the gear 624 via a geometric coupling, and the driveshaft 606 and gear 624 are constrained by a fourth distal bearing 656.

The third bevel gear 624 is rotatably coupled to a third intermediate bevel gear 684, as best shown in FIGS. 13, 14A, and 14B. Further, the bevel gear 684 is rotatably coupled to a second output bevel gear 692, which is rotationally coupled with or integral with the second (or "outer") rotatable output member 674. The third intermediate bevel gear 684 is supported by a fifth distal bearing 657. The second output bevel gear 692 is supported by a first output bearing 694 and a second output bearing 696 in relation to the first output bevel gear 690. Thus, actuation of the motor (not shown) coupled to the third driven gear 614 causes rotation of the third driven gear 614, which causes rotation of the third driveshaft 606. Rotation of the third driveshaft 606 causes rotation of the third bevel gear 624, which causes rotation of the third intermediate bevel gear 684 around an axis perpendicular to the axis of rotation of the driveshafts 602, 604, 606, 608. And rotation of the third intermediate bevel gear 684 causes rotation of the second output bevel gear 692 around an axis parallel to the axis of rotation of the driveshafts 602, 604, 606, 608, which causes rotation of the second rotatable output member 674 around the same axis of rotation. It is understood that the second rotatable output member 674 is configured to be coupled to an actuatable component, such as a portion of a robotic arm wrist, an end effector, or a robotic upper arm, depending on the location of the joint 600 on the robotic device.

The fourth driveshaft 608 is rotatably disposed around the third driveshaft 606 (and thus around the first and second driveshafts 602, 604 as well) and has a fourth driven gear 616 fixedly or integrally attached at its proximal end. The fourth driveshaft 608 is supported at its proximal end by the fourth proximal bearing 646 and a fifth proximal bearing 648 and, with the fourth bearing 646 being supported by the fourth driven gear 616 and the fifth bearing 648 being supported by an enclosure (not shown) of the joint 600. In addition, the fifth bearing 648 is retained in place by a retaining ring 649. At its distal end, the fourth driveshaft 608 is rotationally coupled to or integral with a first retaining member 700, as best shown in FIGS. 13, 14A, and 14B. The first retaining member 700 has two arms 700A, 700B, as best shown in FIGS. 13 and 14A, wherein the rotatable cylinder 681 and attached first intermediate bevel gear 680 are disposed between the two arms 700A, 700B. Further, two bolts 702, 704 are positioned through the arms 700A, 700B, respectively, and threaded into the rotatable cylinder 681. The two bolts 702, 704 are radially supported by first and second bolt bearings 706, 708, as best shown in FIG. 13. More specifically, the two bolts have heads 702A, 704A (as best shown in FIG. 13) sized to fit within the bearings 706, 708. The heads 702A, 704A are positioned in contact with (or "rest on") washers 710, 712, respectively.

Thus, actuation of the motor (not shown) coupled to the fourth driven gear 616 causes rotation of the fourth driven gear 616, which causes rotation of the fourth driveshaft 608. Rotation of the fourth driveshaft 608 causes rotation of the first retaining member 700 around an axis that is parallel to the axis of rotation of the driveshafts 602, 604, 606, 608. The rotation of the retaining member 700 causes rotation of the two arms 700A, 700B, which causes rotation of the two bolts 702, 704, which causes rotation of the rotatable cylinder 681 and the entire distal end of the joint 600 (distal to the bearing 648).

It is understood that the driven gears 610, 612, 614, 616 at the proximal end of the driveshafts 602, 604, 606, 608, respectively, are configured to be coupled to gears (not shown) that are driven by motors (not shown). In this specific exemplary figure, the motors and associated gears have been omitted. According to one embodiment, the motors and associated gears could be configured in a fashion similar to those depicted in FIG. 3B. Alternatively, any configuration of motors can be used.

In this implementation, it is understood that the joint 600 provides four degrees of freedom. For example, one degree of freedom is accomplished via the coupling of the first driveshaft 602 to the rotatable cylinder 681 and drive post 662 that results in rotation of the portion of the joint 600 distal to the first intermediate bevel gear 680 around an axis of rotation perpendicular to that of the driveshafts 602, 604, 606, 608. Another degree of freedom is accomplished via the coupling of the second driveshaft 604 to the first (or "inner") rotatable output member 672 that results in rotation of the output member 672 around an axis parallel to the axis of rotation of the driveshafts 602, 604, 606, 608. A further degree of freedom is achieved by the coupling of the third driveshaft 606 to the second (or "outer") rotatable output member 674 that results in rotation of the output member 674 around an axis parallel to the axis of rotation of the driveshafts 602, 604, 606, 608. Finally, another degree of freedom is accomplished via the coupling or integration of the fourth driveshaft 608 to the first retaining member 700 that results in rotation of the entire distal end of the joint 600 (distal to the bearing 648) around an axis that is parallel to the axis of rotation of the driveshafts 602, 604, 606, 608.

In certain alternative embodiments, the joint 600 can also have an optional passive retaining member (also referred to as a "second retaining member") 720. The passive retaining member 720 is typically incorporated in those embodiments in which the joint 600 is a wrist joint 600, but it can be incorporated into other types of joints as well. In one specific example, the passive retaining member 720 could be used to couple the joint 600 to the end effector 320 depicted in FIGS. 9A-9C. In accordance with one implementation, the passive retaining member 720 provides a stationary foundation for the first and second rotatable output members 672, 674. The retaining member 720 has a channel 722 defined on an outer surface of the member 720 that can be used to help with securing any flexible outer protection sleeves (not shown) thereto. The retaining member 720 is positioned over the bolt heads 702A, 704A such that the bolt heads 702A, 704A help to retain the member 720 in its coupling with the joint 600, with first retaining member bearing 724 and second retaining member bearing 726 serving as the interface between the member 720 and the heads 702A, 704A.

In other embodiments, the joint 600 has no passive retaining member, as best shown in FIG. 14A. In certain implementations, this is the configuration that is utilized when the joint 600 is a shoulder joint 600, rather than a wrist joint.

Alternative joint implementations are best shown in FIGS. 15A-17D, in which the joints have four degrees of freedom while requiring only three motors, as mentioned above. In certain implementations, the joint embodiments below can be incorporated into a wrist joint, while in other implementations, the joint embodiments below can be incorporated into a shoulder joint. As mentioned above, these three motor configurations are possible because all three motors are coupled together in a shared state in which a fourth degree of freedom is realized. More specifically, the coupling of the three motors can be accomplished in several ways, including by providing a braking force condition on one of the outputs such that only deliberate commands will cause a robotic joint to actuate.

Figure 15A:
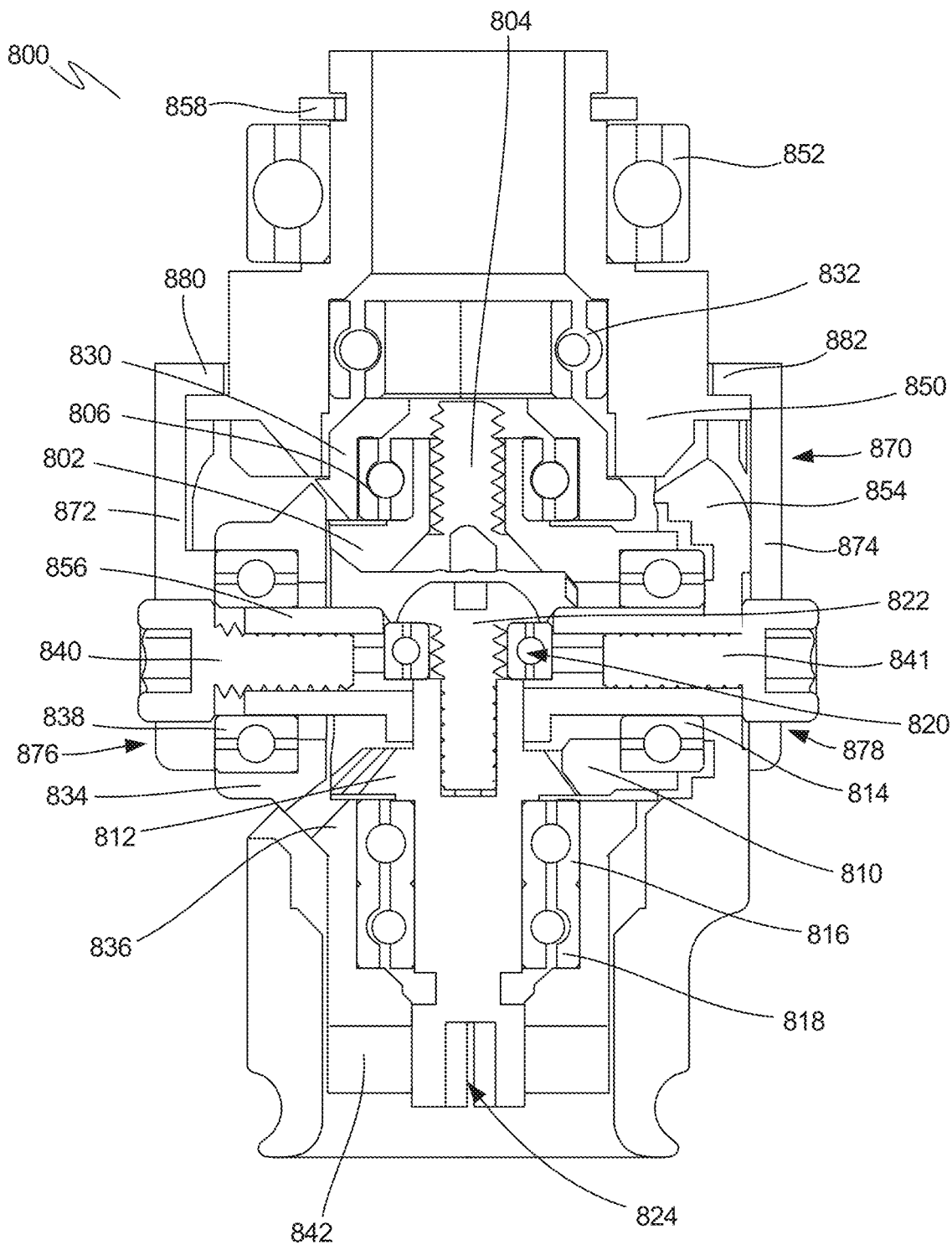
FIG. 15A is a cross-sectional side view of a joint for a robotic device, according to another embodiment.
Figure 15B:
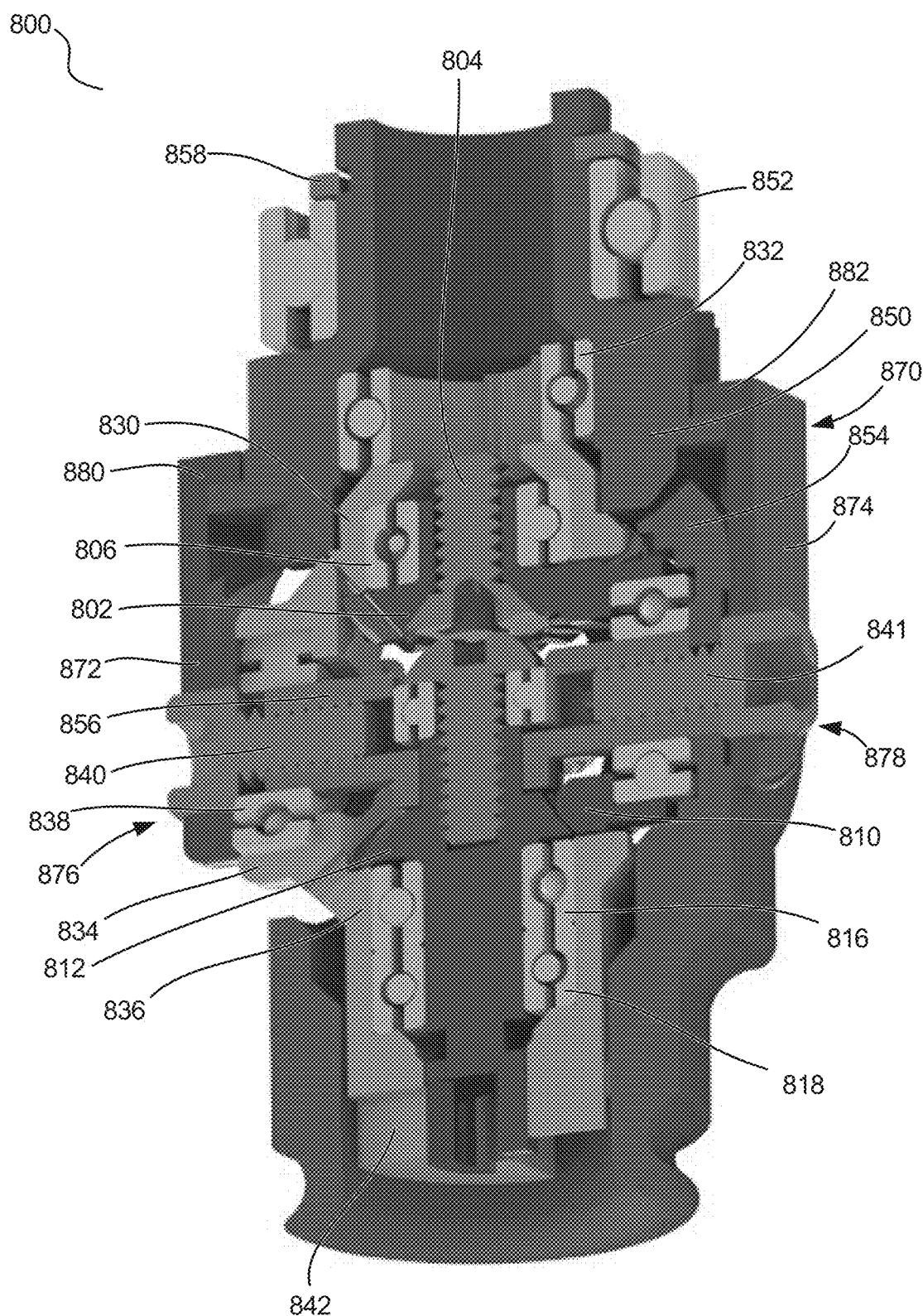
FIG. 15B is a cross-sectional perspective view of the joint of FIG. 15A, according to another embodiment.
Figure 16A:
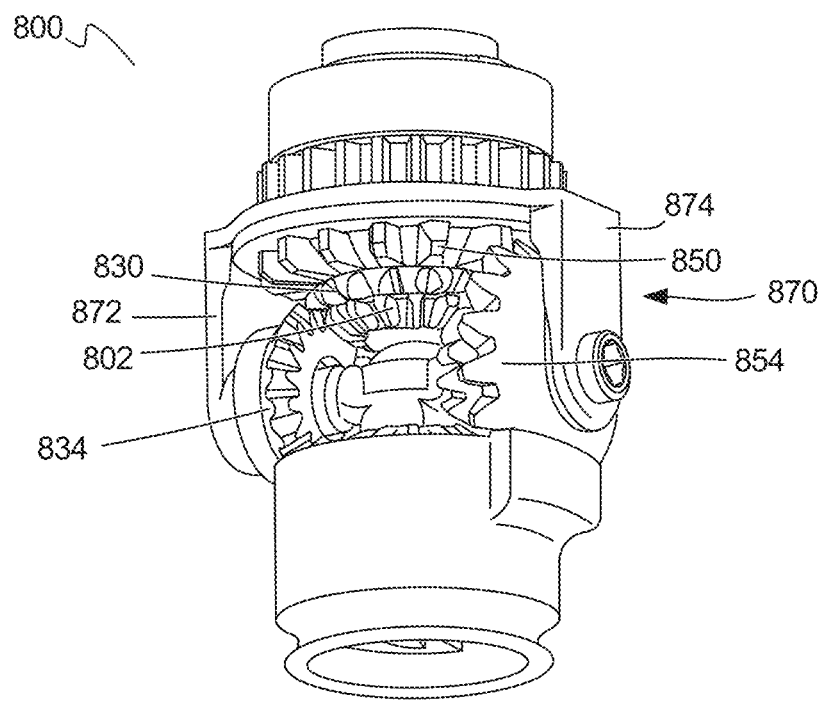
FIG. 16A is a perspective view of the joint of FIG. 15A, according to another embodiment.
Figure 16B:
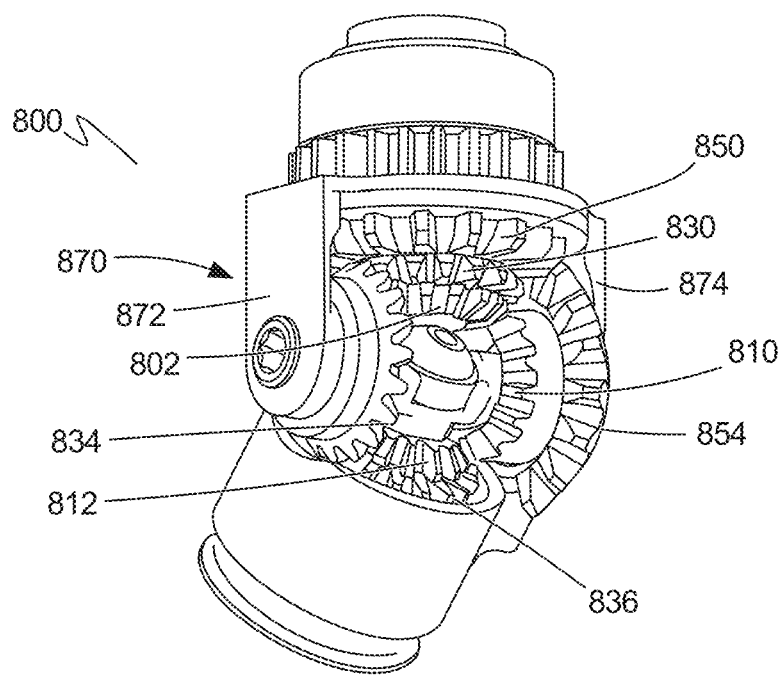
FIG. 16B is a perspective view of the joint of FIG. 15A, according to another embodiment.
Figure 17A:
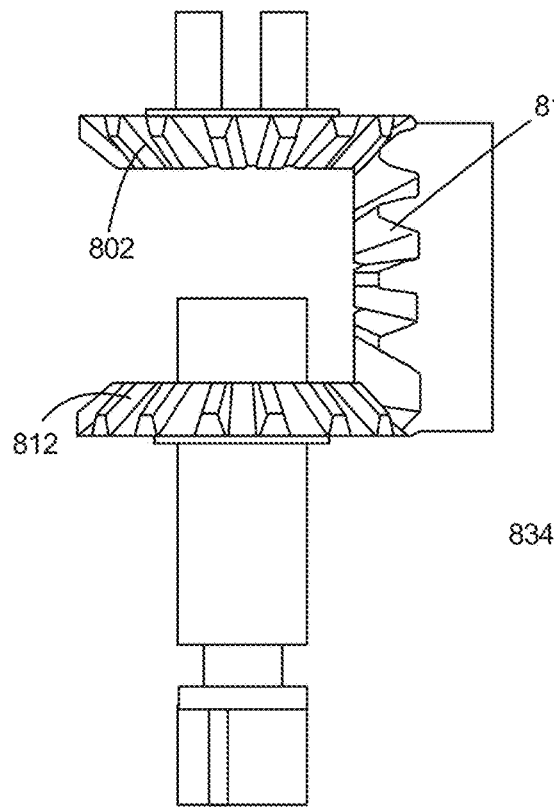
FIG. 17A is a side view of certain components of the joint of FIG. 15A, according to another embodiment.
Figure 17B:
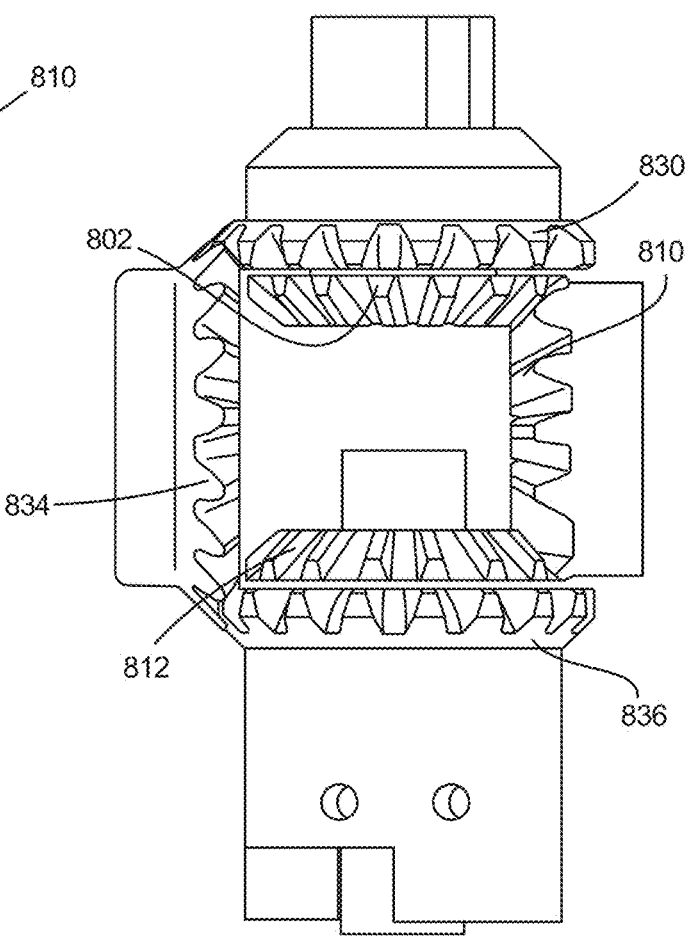
FIG. 17B is a side view of certain components of the joint of FIG. 15A, according to another embodiment.
Figure 17C:
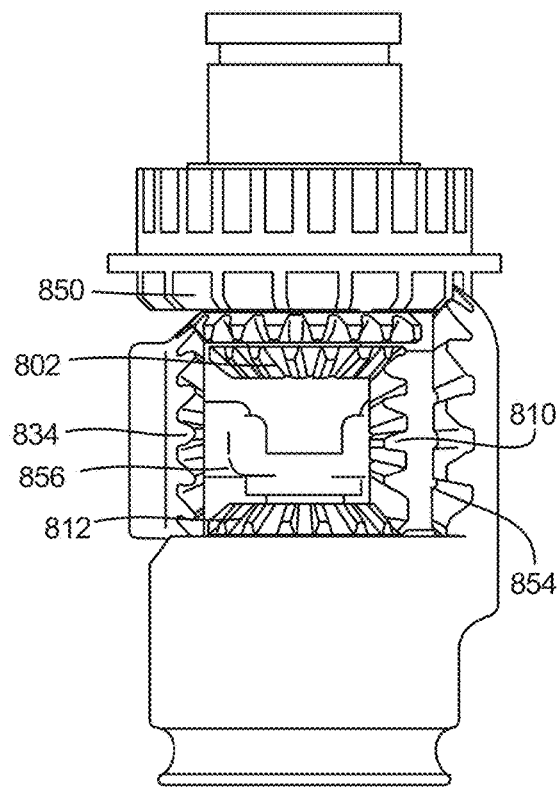
FIG. 17C is a side view of certain components of the joint of FIG. 15A, according to another embodiment.
Figure 17D:
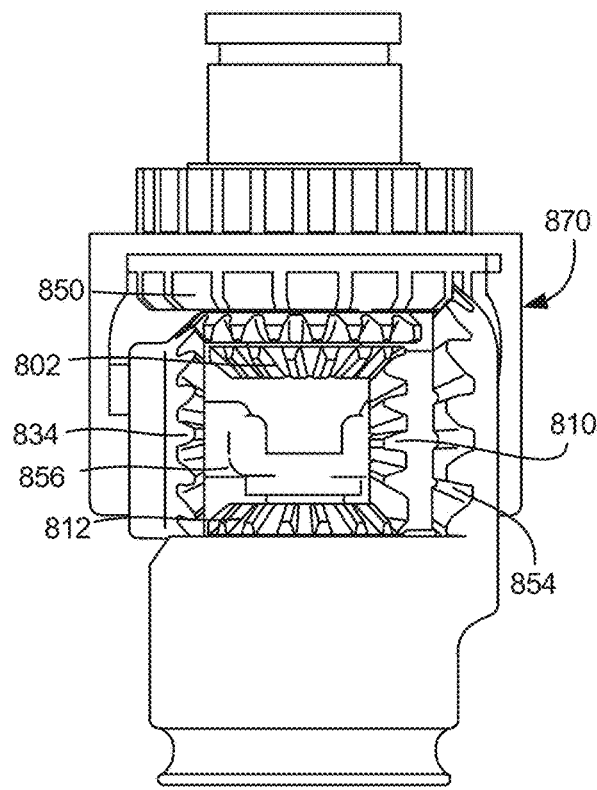
FIG. 17D is a side view of certain components of the joint of FIG. 15A, according to another embodiment.

FIGS. 15A and 15B depict a cross-sectional front view of a joint 800 according to one embodiment having a set of nested driveshafts (not shown) that are coupled to separate bevel gears as discussed below in a configuration similar to that described above with respect to FIGS. 13-14B. While the actual nested driveshafts are not depicted in this particular implementation, it is understood that the driveshafts (not shown) are substantially similar to those described above with respect to FIGS. 13-14B. More specifically, in this embodiment, the joint 800 has a set of three nested driveshafts, including a first (also referred to herein as "inner") driveshaft (not shown), a second (also referred to as "middle") driveshaft (not shown), and a third (also referred to as "outer") driveshaft (not shown).

The first driveshaft (not shown) is rotationally coupled to a first bevel gear 802, as best shown in FIGS. 15A, 15B, 16A, 16B, and 17A, such that rotation of the driveshaft (not shown) causes rotation of the first bevel gear 802. According to one embodiment, the driveshaft (not shown) is coupled to the gear 802 via a geometric coupling, and the gear 802 is retained axially in relation to the driveshaft (not shown) by bolt 804 which is threaded into the driveshaft (not shown). The driveshaft (not shown) and gear 802 are constrained in a first bearing 806, which is inset in second bevel gear 830, which is discussed below.

The first bevel gear 802 is rotatably coupled to a first intermediate bevel gear 810, as best shown in FIGS. 15A, 15B, 16A, 16B, and 17A, such that rotation of the first bevel gear 802 causes rotation of the first intermediate bevel gear 810. The intermediate bevel gear 810 is rotatably coupled to first output bevel gear 812 such that rotation of the first intermediate bevel gear 810 causes rotation of the first output bevel gear 812. The first intermediate bevel gear 810 is axially constrained by second bearing 814, which is inset in third intermediate bevel gear 854. The first output bevel gear 812 is constrained by third and fourth bearings 816, 818, which are inset in the second output bevel gear 836. In addition, the first output bevel gear 812 is further constrained where the gear 812 interfaces with the crossbar 856, which is discussed in detail below, along with the fifth bearing 820 and the axial bolt 822. The fifth bearing 820 rotationally separates (provides a rotational interface between) first output bevel gear 812 from the crossbar 856. The output bevel gear 812 is rotationally coupled to or integral with a first generic output interface 824, which can couple to any component intended to be actuated. Alternatively, any type of known coupling component or interface can be coupled to or integral with the bevel gear 812.

Thus, actuation of the motor (not shown) coupled to the first driveshaft (not shown) causes rotation of the first driveshaft (not shown). Rotation of the first driveshaft (not shown) causes rotation of the first bevel gear 802, which causes rotation of the first intermediate bevel gear 810 around an axis perpendicular to the axis of rotation of the first bevel gear 802. And rotation of the first intermediate bevel gear 810 causes rotation of the first output bevel gear 812, which causes rotation of the first generic output interface 824 around the same axis of rotation as the first bevel gear 802.

The second driveshaft (not shown) is rotationally coupled to a second bevel gear 830, as best shown in FIGS. 15A, 15B, 16A, 16B, and 17B, such that rotation of the driveshaft (not shown) causes rotation of the second bevel gear 830. According to one embodiment, the driveshaft (not shown) is coupled to the gear 830 via a geometric coupling, and the gear 830 is retained axially in relation to the driveshaft (not shown) in part by the bolt 804 discussed above, which is threaded into the first driveshaft (not shown). According to one embodiment, the bolt 804 compresses the first and second bevel gears 802, 830 such that axial movement is minimized or prevented. The second driveshaft (not shown) and gear 830 are constrained in a sixth bearing 832, which is inset in third bevel gear 850, which is discussed below.

The second bevel gear 830 is rotatably coupled to a second intermediate bevel gear 834, as best shown in FIGS. 15A, 15B, 16A, 16B, and 17B, such that rotation of the second bevel gear 830 causes rotation of the second intermediate bevel gear 834. The intermediate bevel gear 834 is rotatably coupled to second output bevel gear 836 such that rotation of the second intermediate bevel gear 834 causes rotation of the second output bevel gear 836. The second intermediate bevel gear 834 is axially constrained by seventh bearing 838, which is disposed on the crossbar 856, along with the threaded coupling of the bolt 840 with the crossbar 856. The second output bevel gear 836 is constrained by the third and fourth bearings 816, 818, which are discussed above. The output bevel gear 836 is rotationally coupled to or integral with a second generic output interface 842, which can couple to any component intended to be actuated. Alternatively, any type of known coupling component or interface can be coupled to or integral with the bevel gear 836.

Thus, actuation of the motor (not shown) coupled to the second driveshaft (not shown) causes rotation of the second driveshaft (not shown). Rotation of the second driveshaft (not shown) causes rotation of the second bevel gear 830, which causes rotation of the second intermediate bevel gear 834 around an axis perpendicular to the axis of rotation of the second bevel gear 830. And rotation of the second intermediate bevel gear 834 causes rotation of the second output bevel gear 836, which causes rotation of the second generic output interface 842 around the same axis of rotation as the second bevel gear 830.

The third driveshaft (not shown) is rotationally coupled to a third bevel gear 850, as best shown in FIGS. 15A, 15B, 16A, 16B, and 17C, such that rotation of the driveshaft (not shown) causes rotation of the third bevel gear 850. According to one embodiment, the driveshaft (not shown) is coupled to the gear 850 via a geometric coupling, and the gear 850 is retained axially in relation to the driveshaft (not shown) in part by the bolt 804 discussed above, which is threaded into the first driveshaft (not shown). The third driveshaft (not shown) and gear 850 are constrained in an eighth bearing 852, which is inset in the enclosure (not shown) of the joint 800, which is discussed below. In one implementation, a retaining ring 858 is disposed on the shaft of the third bevel gear 850 such that the third bevel gear 850 cannot be moved axially in relation to the eighth bearing 852.

The third bevel gear 850 is rotatably coupled to a third intermediate bevel gear 854, as best shown in FIGS. 15A, 15B, 16A, 16B, and 17C, such that rotation of the third bevel gear 850 causes rotation of the third intermediate bevel gear 854. The intermediate bevel gear 854 is rotationally coupled to or integral with a rotatable cylinder (also referred to herein as a "crossbar") 856 such that rotation of the third intermediate bevel gear 854 causes rotation of the rotatable cylinder 856. The second intermediate bevel gear 834 is axially constrained by the second 814 and seventh 838 bearings, which are both disposed on the crossbar 856, along with the threaded coupling of the bolt 840 with the crossbar 856. The crossbar 856 is rotationally coupled to the distal portion of the joint 800, which is the portion distal from the crossbar 856, such that rotatable crossbar 856 causes rotation of the distal portion of the joint 800 around an axis perpendicular to the axis of the third bevel gear 850. A distal enclosure 860, according to one embodiment, is disposed over the distal portion of the joint 800. In one implementation, the distal enclosure 860 provides a sealing surface for any external sealing bag system such as those systems discussed elsewhere herein.

Thus, actuation of the motor (not shown) coupled to the third driveshaft (not shown) causes rotation of the third driveshaft (not shown). Rotation of the third driveshaft (not shown) causes rotation of the third bevel gear 850, which causes rotation of the third intermediate bevel gear 854 around an axis perpendicular to the axis of rotation of the third bevel gear 850. And rotation of the third intermediate bevel gear 854 causes rotation of the crossbar 856, which causes rotation of the distal portion of the joint 800 around an axis of rotation that is perpendicular to the third bevel gear 850.

In addition to the three different degrees of freedom described above with respect to the first and second output bevel gears 812, 836 and the rotatable crossbar 856, a fourth degree of freedom can be provided by a support member (also referred to herein as a "spacing member") 870 which is positioned over a portion of the joint 800, as best shown in FIGS. 15A, 15B, 16A, 16B, and 17D. More specifically, the support member 870 has a first arm 872 and a second arm 874, with both arms having openings 876, 878 configured to receive the heads of the bolts 840, 841 such that the retainer 870 constrains the heads of the bolts 840, 841, thereby maintaining the coupling and the spacing of the bevel sets (the coupling of the first bevel gear 802 and the first intermediate bevel gear 810, the coupling of the second bevel gear 830 and the second intermediate bevel gear 834, and the coupling of the third bevel gear 850 and the third intermediate bevel gear 854). The arms 872, 874 have interfaces 880, 882 that contact the third bevel gear 850 such that the retainer 870 is rotatable in relation to the third bevel gear 850.

In certain implementations, the support member 870 makes it possible for the joint 800 to use only three complex motors (typically very expensive components) instead of four to allow for movement around four degrees of freedom. That is, the three expensive motors are coupled together in a shared state such that a fourth degree of freedom is realized. For example, the coupling can be accomplished by providing a braking system (in the form of a smaller, less complex, and inexpensive motor) on one of the outputs such that only deliberate commands will cause the joint to actuate. In other words, the use of the simple motor for braking makes it possible to take advantage of the coupled nature of the bevel gear differential system.

In use, the various device embodiments disclosed or contemplated herein are utilized to perform minimally invasive surgery in a target cavity of a patient, such as, for example, the peritoneal cavity. In certain implementations, with reference to FIG. 1A, the device body 12 is positioned through an incision into the target cavity such that the shoulders 14, 16 and the arms attached thereto are positioned within the target cavity, with the shaft section 12B disposed through the incision and the motor section 12A positioned outside the patient's body. In those implementations, the device body 12 is attached to some type of support component outside the patient's body to provide stability and ensure that the body 12 remains stationary when desired.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Although the present invention has been described with reference to preferred embodiments, persons skilled in the art will recognize that changes may be made in form and detail without departing from the spirit and scope of the invention.

What is claimed is:

1. A robotic device comprising:
   (a) an elongate device body comprising:
   a first driveshaft rotatably disposed within the device body, the first driveshaft comprising:
   (A) a first lumen defined along a length of the first driveshaft; and
   (B) a first drive gear operably coupled to the first driveshaft;
   a second driveshaft rotatably disposed within the first lumen, the second driveshaft comprising:
   (A) a second lumen defined along a length of the second driveshaft; and (B) a second drive gear operably coupled to the second driveshaft; and
(iii) a third driveshaft rotatably disposed within the second lumen;
(b) a first shoulder joint comprising:
(i) a conversion body operably coupled to at least one of the first, second, or third driveshafts, wherein the conversion body is a yoke body comprising a yoke shaft extending from the yoke body, wherein a longitudinal axis of the yoke shaft is transverse to a longitudinal axis of the first driveshaft;
(ii) a rotation body rotatable in relation to the conversion body, the rotation body comprising first and second co-planar openings;
(iii) an output gear; and
(iv) a plurality of intermediate gears operably coupling the second drive gear to the output gear through the first and second openings in the rotation body; and
(c) a first arm operably coupled to the first shoulder joint.

2. The robotic device of claim 1, wherein the yoke body further comprises a yoke opening defined in the yoke shaft.

3. The robotic device of claim 2, wherein the third driveshaft is rotatably disposed through the yoke opening, the third driveshaft being operably coupled to a third drive gear.

4. The robotic device of claim 3, wherein the first and third drive gears are rotatably coupled to the rotation body.

5. The robotic device of claim 1, wherein at least one of the first drive gear and the second drive gear comprises a bevel gear.

* * * * *